US012092645B2

(12) United States Patent
Tamura et al.

(10) Patent No.: US 12,092,645 B2
(45) **Date of Patent: *Sep. 17, 2024**

(54) METHOD FOR DISCRIMINATING A MICROORGANISM

(71) Applicants: SHIMADZU CORPORATION, Kyoto (JP); MEIJO UNIVERSITY, Nagoya (JP)

(72) Inventors: Hiroto Tamura, Nagoya (JP); Naomi Yamamoto, Nagoya (JP); Teruyo Kato, Toyota (JP); Keisuke Shima, Kyoto (JP); Shinji Funatsu, Kyoto (JP)

(73) Assignees: SHIMADZU CORPORATION, Kyoto (JP); MEIJO UNIVERSITY, Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/059,404

(22) Filed: Nov. 28, 2022

(65) Prior Publication Data

US 2023/0213528 A1 Jul. 6, 2023

Related U.S. Application Data

(63) Continuation of application No. 16/089,922, filed as application No. PCT/JP2016/060868 on Mar. 31, 2016, now Pat. No. 11,561,228.

(51) Int. Cl.

| | |
|---|---|
| ***G01N 33/68*** | (2006.01) |
| ***C12Q 1/04*** | (2006.01) |
| *C12N 15/09* | (2006.01) |

(52) U.S. Cl.

CPC ........... *G01N 33/6848* (2013.01); *C12Q 1/04* (2013.01); *C12N 15/09* (2013.01); *G01N 2333/195* (2013.01); *G01N 2560/00* (2013.01)

(58) Field of Classification Search

USPC ........................................................ 436/173

See application file for complete search history.

(56) References Cited

U.S. PATENT DOCUMENTS

2014/0288852 A1 9/2014 Ojima et al.

FOREIGN PATENT DOCUMENTS

JP 2006-191922 A 7/2006
JP 2007-316063 A 12/2007

(Continued)

OTHER PUBLICATIONS

Communication dated Mar. 31, 2023 from the European Patent Office in Application No. 16896960.8.

(Continued)

*Primary Examiner* — Xiaoyun R Xu
(74) *Attorney, Agent, or Firm* — Sughrue Mion, PLLC

(57) ABSTRACT

To provide a method for discriminating a microorganism by selecting and using a marker protein capable of reproducibly and quickly discriminating a bacterial species of the genus *Listeria*. The method for discriminating a microorganism according to the present invention includes: a step of subjecting a sample containing a microorganism to mass spectrometry to obtain a mass spectrum; a reading step of reading a mass-to-charge ratio m/z of a peak derived from a marker protein from the mass spectrum; and a discrimination step of discriminating which bacterial species of *Listeria* bacteria the microorganism contained in the sample contains based on the mass-to-charge ratio m/z, in which at least one of 17 ribosomal proteins L3, L4, L23, L2, L24, L6, L18, S5, L15, S13, S11, L10, L21, L13, S9, L31, S16 is used as the marker protein and particularly at least one of 8 ribosomal proteins L24, L6, L18, L15, S9, L31, S16 among the 17 ribosomal proteins is used.

2 Claims, 18 Drawing Sheets

Specification includes a Sequence Listing.

(56) References Cited

FOREIGN PATENT DOCUMENTS

| | | | |
|---|---|---|---|
| JP | 2013-85517 | A | 5/2013 |
| JP | 2015-184020 | A | 10/2015 |

OTHER PUBLICATIONS

Communication dated Apr. 28, 2023 from the European Patent Office in Application No. 16896960.8.

Testimony of Séverine François, Engineer, EU System Engineering & Support and Global Assets, bioMérieux, Jan. 27, 2023, (8 total pages).

Testimony of Olivier Lafrique, Senior Global Customer Service Manager, Expert Microbiology & IT France, bioMérieux, Jan. 26, 2023, (1 total page).

Proofs of sales to two clients (AU MED CTR and Real Hospital Portugues), (25 total pages).

Serigraphy of client DVD, Ruo Saramis KB4. 13.0, Vitek MS, bioMérieux, 2014, (1 total page).

Content of client DVD, Vitekms-Ruo-Saramis-KB 4.13.0KB4.13.0, pp. 1-2 (2 total page).

"Product Definition for a Digital Medium (Software and/or Documentation)", Saramis KB4.13.0, product 417388, bioMérieux, DFP/417388 Issue: 01, pp. 1-9 (19 total pages).

Christian Barras et al., "Industrialization of Digital Media and Paper Documentation", bioMérieux, Issue 03.A, Jan. 27, 2014, Doc No. 018698, (25 total pages).

"Check-List and Launch Sheet for Software / Documentation Products in DVD Format", BioMérieux, Doc No. 018940, pp. 1-4 (9 total pages).

"System Impact Study Form, Reference: Vitek MS Ruo Saramnis KB V4.13.0, FGM/RDS/M00094", bioMerieux, 008714—Rev 02.B—Attachment 1, pp. 1-19 (85 total pages).

"Bailiff Report, Certified Report", Adrastee SELARL d'Huissiers de Justice, Mar. 17, 2023, pp. 1-38 (38 total pages).

VITEK® MS Plus, VITEK R MS IVD and VITEK® MS Research Use Only software combination, Website bioMerieux, Sep. 29, 2015 (5 pages total).

"SARAMIS™ Softwareupdate V.4.0 and Mycobacteria Database Update V.4.12.0 for VITEK MS RUO", bioMerieux Germany GmbH, Oct. 8, 2013 (3 pages total).

"SARAMIS™ database update containing *Nocardia* and *Aspergillus* species (V.4.13.0) for the VITEK® MS Plus and the VITEK® MS RUO System", Mar. 2014 (1 page total).

"SARAMIS update KB V.4.13.0, VITEK® MS Plus & VITEK® MS RUO", Apr. 4, 2014 (5 pages total).

"VITEK® MS Plus—Saramis KB 4.14 Update", Jul. 18, 2016 (2 pages total).

"Bailiff report on SARAMIS Database V4.13", Apr. 2014 (34 pages total).

Gulsen Hascilek et al., "Identification of Viridans Streptococks Isolated From Clinical Samples with BD Phoenix, Vitek MS, Maldi Biotyper and Comparison with 16S RDNA Gene Sequence", Cover, summary and p. 167 of the Leaflet of a Microbiology congress in Turkish language https://www.klimud.ord/public/up!oads/content/files/2015%20ko ngre%20kitab%C4%BI.PDF, Nov. 18-22, 2015 (5 pages total).

Snehal Jadhav, "Detection, subtyping and control of Listeria monocytogenes in food processing environments", A thesis submitted for the degree of Doctor of Philosophy, Department of Chemistry and Biotechnology, Swinburne University of Technology, Nov. 2015 (248 pages total).

Tamura et al., "Novel Accurate Bacterial Discrimination by MALDI-Time-of-Flight MS Based on Ribosomal Proteins coding in S10-spc-alpha Operon at Strain Level S10-GERMS", J. Am. Soc. Mass Spectrom, vol. 24, pp. 1185-1193, 2013 (9 Pages total).

Sato et al."Characterization of the *Lactobacillus casei* group based on the profiling of ribosomal proteins coded in S10-spc-alpha operons as observed by Aug. 2012 MALDI-TOF MS", Systematic and Applied Microbiology, vol. 35, pp. 447-454, 2012 (8 pages total).

Teramoto et al. "Phylogenetic classification of *Pseudomonas putida* strains by MALDI-MS using ribosomal subunit proteins as biomarkers", Analytical Chemistry, vol. 79, No. 22, Nov. 15, 2007 (8 pages total).

Notice of Opposition dated Feb. 23, 2022 from European Patent Office in European Patent No. 3438276.

Communication dated Apr. 26, 2022 from The State Intellectual Property Office of P R. of China in Application No. 201680084038.9.

Office Action issued Dec. 2021 in Chinese Application No. 201680084038.9.

Yang et al., "Two-dimensional electrophoresis map of Listeria monocytogenes proteome and proteomic analysis of stationary growth phase cells", Chinese Journal of Health Laboratory Technology, 2009, vol. 19, No. 3 (12 pages total).

Promadel, N. et al. Cell Wall Teichoic Acid Glycosylation in Listeria monocytogenes Serotype 4b Requires gtcA, a Novel Serogroup-Specific Gene, Journal of Bacteriology, 181(2), p. 418-425 (Year: 1999).

Hanna, S.E. et al. Assessment of Environmental Factors on Listeria monocytogenes Scott A inlA Gene Expression by Relative Quantitative Taqman Real-Time Reverse Transcriptase PCR, Journal of Food Protection, vol. 69, No. 11, 2006, pp. 2754-2757 (Year: 2006).

Zhu, X., et al. Phenotypic, Proteomic, and Genomic Characterization of a Putative ABC-Transporter Permease Involved in Listeria monocytogenes Biofilm Formation, Foodborne Pathogens and Disease vol. 8, No. 4, 2011 (Year: 2011).

Ojima-Kato, T. et al. Discrimination of *Escherichia coli* 0157, 026 and 0111 from Other Serovars by MALDI-TOF MS Based on the S10-GERMS Method, PLOS One, vol. 9(11), e113458 (Year: 2014).

List of prokaryotic names with standing in nomenclature, [searched on Sep. 18, 2015], Internet <URL: http://www.bacterio.net/>.

Henk C den Bakker et al., "Comparative genomics of the bacterial genus *Listeria*: Genome evolution is characterized by limited gene acquisition and limited gene loss", BMC Genomics 2010, 11, 688, 20 pages total.

Marco Favaro et al., "First case of *Listeria innocua* meningitis in a patient on steroids and eternecept", JMM Case Reports (2014), 5 pages total.

Bala Swaminathan et al., "The epidemiology of human listeriosis", Microbes and Infection 9 (2007) pp. 1236-1243, 8 pages total.

Renato H. Orsi et al., "*Listeria monocytogenes* lineages: Genomics, evolution, ecology, and phenotypic characteristics", International Journal of Medical Microbiology 301 (2011) pp. 79-96, 18 pages total.

Todd J. Ward et al., "Multilocus Genotyping Assays for Single Nucleotide Polymorphism-Based Subtyping of *Listeria monocytogenes* Isolates", Applied and Environmental Microbiology, vol. 74, No. 24, Dec. 2008, pp. 7629-7642, 14 pages total.

Lewis M. Graves et al., "PulseNet standardized protocol for subtyping *Listeria monocytogenes* by macrorestriction and pulsed-field gel electrophoresis", International Journal of Food Microbiology 65 (2001) pp. 55-62, 8 pages total.

C. Salcedo et al., "Development of a Multilocus Sequence Typing Method for Analysis of *Listeria monocytogenes* Clones", Journal of Clinical Microbiology, vol. 41, No. 2, Feb. 2003, pp. 757-762, 6 pages total.

Marie Ragon et al., "A New Perspective on *Listeria monocytogenes* Evolution", PLoS Pathogens, vol. 4, Issue 9, e1000146, Sep. 2008, 14 pages total.

Monica K. Borucki et al., "Discrimination among *Listeria monocytogenes* isolates using a mixed genome DNA microarray", Veterinary Microbiology 92 (2003) pp. 351-362, 12 pages total.

Snehal Jadhav et al., "Rapid identification and source-tracking of *Listeria monocytogenes* using MALDI-TOF mass spectrometry", International Journal of Food Microbiology 202 (2015) pp. 1-9, 9 pages total.

Po-Ren Hsueh et al., "Bruker Biotyper Matrix-Assisted Laser Desorption Ionization—Time of Flight Mass Spectrometry System for Identification of *Nocardia, Rhodococcus, Kocuria, Gordonia,*

(56) References Cited

OTHER PUBLICATIONS

*Tsukamurella,* and *Listeria* Species", Journal of Clinical Microbiology, vol. 52, No. 7, Jul. 2014, pp. 2371-2379, 9 pages total.
Michel Doumith et al., "Differentiation of the Major *Listeria monocytogenes* Serovars by Multiplex PCR", Journal of Clinical Microbiology, vol. 42, No. 8, Aug. 2004, pp. 3819-3822, 4 pages total.
Hotta et al., "Classification of Genus Pseadomonas by MALDMOF IVIS Based on RibosomaS Protein Codjng in S10—spc—afpha Operon at Strain Level", Journal of Proteome Research, vol. 9, 2010, p. 6722- 6728, 7 pages total.
Hotta et al., Classification of the Genus *Bacillus* Based on MALDI-TOF MS Analysis of Ribosomal Proteins Coded in S10 and spc Operons, Journal of Agricultural and Food Chemistry, vol. 59, 2011, pp. 5222-5230, 9 pages total.
Suarez et al., Ribosomal proteins as biomarkers for bacterial identification by mass spectrometry in the clinical microbiology laboratory, Journal of Microbiological Methods, vol. 94, 2013, pp. 390-396, 7 pages total.
Sukhadeo B. Barbuddhe et al., "Rapid Identification and Typing of Listeria Species by Matrix-Assisted Laser Desorption Ionization-Time of Flight Mass Spectrometry", Applied and Environmental Microbiology, vol. 74, No. 17, Sep. 2008, pp. 5402-5407, 6 pages total.
E. Farfour et al., "Evaluation of the Andromas Matrix-Assisted Laser Desorption Ionization—Time of Flight Mass Spectrometry System for Identification of Aerobically Growing Gram-Positive Bacilli", Journal of Clinical Microbiology, vol. 50, No. 8, Aug. 2012, pp. 2702-2707, 6 pages total.
International Search Report dated Jul. 5, 2016 issued by the International Searching Authority in PCT/JP2016/060868.
International Preliminary Report on Patentability with the translation of Written Opinion dated Oct. 2, 2018 issued by the International Bureau in PCT/JP2016/060868.
Brief Communication issued Oct. 26, 2023 from the European Patent Office in Application No. 16896960.8.
Brief Communication issued Sep. 14, 2023 from the European Patent Office in Application No. 16896960.8.
Communication issued Sep. 8, 2023 from European Patent Office in Application No. 16896960.8.
Transmittal of Decision, Summons, Opposition, issued Jul. 27, 2023 from the European Patent Office in Application No. 16896960.8.
Druckexemplar in Opposition Procedure issued Jun. 22, 2023 For European Publication No. 3438276 B1.
Scanned Annex to a Communication, Opposition Procedure 5, Auxiliary Request 1, issued Jun. 22, 2023 for European Publication No. 3438276 B1.
Scanned Annex to a Communication, Opposition Procedure 4, Auxiliary Request 1, issued Jun. 22, 2023 for European Publication No. 3438276 B1.
Scanned Annex to a Communication, Opposition Procedure 3, Consolidated List, from the European Patent Office for Application No. 16896960.8.
Scanned Annex to Communication, Opposition Procedure 2, Auxiliary Request 1, Claims, issued Jun. 22, 2023 for European Application No. 16896960.8.
Scanned Annex to a Communication, Opposition Procedure, Auxiliary Request 1, Claims(editorial corrections), issued Jun. 22, 2023 for European Application No. 1689690.8.
Grounds for Decision (Annex), Opposition, Summary of Facts and Submissions, issued Jul. 27, 2023 in European Application No. 16896960.8.
Communication issued Jul. 27, 2023 from European Patent Office in Application No. 16896960.8.
Annex to the Communication, Opposition, issued Jul. 27, 2023 in European Application No. 16896960.8.
Brief Communication, Opposition Proceedings, issued Jun. 15, 2023 from the European Patent Office in Application No. 16896960. 8.
Written Submission in Preparation to During Oral Proceedings, issued Jun. 12, 2023 from the European Patent Office in Application No. 16896960.8.
Brief Communication, Opposition Proceedings 2, issued Apr. 28, 2023 from the European Patent Office in Application No. 16896960. 8.
Brief Communication, Opposition Proceedings, issued Apr. 28, 2023, from the European Patent Office in Application No. 16896960. 8.
Written Submission in Preparation to during Oral Proceedings issued Apr. 21, 2023 in Opposition to patent EP3438276 B1.

Fig. 3

| No. | Genus | Species | Subspecies | Strain | Serotype | Lineage | Supplier |
|---|---|---|---|---|---|---|---|
| 1 | *Listeria* | *monocytogenes* | | ATCC15313$^T$ | 1/2a | II | ATCC |
| 2 | *Listeria* | *monocytogenes* | | JCM2873 | 3d | I | JCM |
| 3 | *Listeria* | *monocytogenes* | | JCM7671 | 1/2a | II | JCM |
| 4 | *Listeria* | *monocytogenes* | | JCM7672 | 1/2a | II | JCM |
| 5 | *Listeria* | *monocytogenes* | | JCM7673 | 3a | II | JCM |
| 6 | *Listeria* | *monocytogenes* | | JCM7674 | 4a | III | JCM |
| 7 | *Listeria* | *monocytogenes* | | JCM7675 | 4b | I | JCM |
| 8 | *Listeria* | *monocytogenes* | | JCM7676 | 1/2b | I | JCM |
| 9 | *Listeria* | *monocytogenes* | | JCM7677 | 3b | I | JCM |
| 10 | *Listeria* | *monocytogenes* | | JCM7678 | 3c | II | JCM |
| 11 | *Listeria* | *seeligeli* | | JCM7679 | 4c | | JCM |
| 12 | *Listeria* | *monocytogenes* | | JCM7680 | 4d | I | JCM |
| 13 | *Listeria* | *seeligeli* | | JCM7682 | 4c | | JCM |
| 14 | *Listeria* | *monocytogenes* | | JCM7683 | 3b | I | JCM |
| 15 | *Listeria* | *monocytogenes* | | ATCC51772 | 1/2a | II | ATCC |
| 16 | *Listeria* | *monocytogenes* | | ATCC19115 | 4b | I | ATCC |
| 17 | *Listeria* | *innocua* | | ATCC33090$^T$ | 6a | | ATCC |
| 18 | *Listeria* | *innocua* | | GTC02960 | | | NBRP |
| 19 | *Listeria* | *ivanovii* | *ivanovii* | JCM7681 | | | JCM |
| 20 | *Listeria* | *ivanovii* | *londoniens* | ATCC49954 | | | ATCC |
| 21 | *Listeria* | *seeligeli* | | ATCC35967$^T$ | | | ATCC |
| 22 | *Listeria* | *welshimeri* | | GTC02963 | 6b | | NBRP |
| 23 | *Listeria* | *grayi* | | ATCC19120$^T$ | | | ATCC |
| 24 | *Listeria* | *rocourtiae* | | GTC16429$^T$ | | | NBRP |

Weak agglutination of H antigen in agglutination test
Listeria of Nos. 11 and 13 was supplied from supplier as L. monocytogenes, but was identified as L. seeligeri by biochemistry test and sequence analysis of 16S RNA

Fig. 4

| Name | Sequence (5'-3') | Application |
|---|---|---|
| Lm-S10-1 | CATGGCGGATGTTCAGGTAA | Amplification and sequence analysis of S10 region |
| Lm-S10-R | CTCCTTCCAGAATAACGGGT | Amplification and sequence analysis of S10 region |
| Lm-S10-2 | AGCAGCACAAAACGTGGTAC | Sequence analysis of S10 region |
| Lm-S10-3 | AAGGAGGACTAACGAATGCC | Sequence analysis of S10 region |
| Lm-S10-4 | TGCACGCAACTTACAAGGCA | Sequence analysis of S10 region |
| Lm-S10-5 | CGGACGCAATAACCAAGGT A | Sequence analysis of S10 region |
| Lm-S10-6 | AATGAACCCGAACGATCACC | Sequence analysis of S10 region |
| Lm-S10-7 | TACAAGCGCAAAAGCCGTTG | Sequence analysis of S10 region |
| Lm-S10-8 | GTGCAGCTAACCGTGTGAAT | Sequence analysis of S10 region |
| Lm-S10-9 | AGGCGGAACTGAAGTTGCAT | Sequence analysis of S10 region |
| Lm-spc-1 | ACCCGTTATTCTGGAAGGAG | Amplification and sequence analysis of spc region |
| Lm-spc-R | AAGGCATTACACCCATGGCA | Amplification and sequence analysis of spc region |
| Lm-spc-F | CTCGTCCATTGTCTGCAACT | Sequence analysis of spc region |
| Lm-spc-2 | CAAACGTAATGCTAMTTGACCC | Sequence analysis of spc region |
| Lm-spc-3 | CGTGGTAACTATACGTTGGGT | Sequence analysis of spc region |
| Lm-spc-4 | GACTGGCGAACGTGTAATCA | Sequence analysis of spc region |
| Lm-spc-5 | TCCTGCAAACACWCAAGTGATT | Sequence analysis of spc region |
| Lm-spc-6 | GGAGGGACATATTACATGCCTG | Sequence analysis of spc region |
| Lm-spc-7 | TTAATCGGACGCCCTCAA | Sequence analysis of spc region |
| Lm-alpha-F | CTCTACCAAACGCGATGTTC | Amplification and sequence analysis of alpha region |
| Lm-alpha-R | GGAAACACAGAGCTAGACAAGG | Amplification and sequence analysis of alpha region |
| Lm-alpha-1 | CCTGACACGCGGAAGAATTA | Sequence analysis of alpha region |
| Lm-alpha-2 | AAGGCCCGTCCAAAACAGTA | Sequence analysis of alpha region |
| Lm-alpha-3 | CAGCGATGATGCCAAGTATG | Sequence analysis of alpha region |
| Lm-alpha-4 | GAAGCAGTTTCACTTGGAGC | Sequence analysis of alpha region |
| Lm-alpha-5 | AACTGGCTGACCTTGGCTT A | Sequence analysis of alpha region |
| Lm-L21-F | CCCCTGTGATGGCGAGTCTT | Amplification and sequence analysis of L21 gene |
| Lm-L21-R | TCTTCTCGCATAACATCGACTTGAA | Amplification of L21 gene |
| Lm-S21-F | TGAAGGATTTAAGTGAGTGCATGT | Amplification and sequence analysis of S21 gene |
| Lm-S21-R | CGCATCGCTTGTTTCATATCT | Amplification of S21 gene |
| Lm-S9-F | TTCGGGAGCTAATTTGTTTCAA | Amplification and sequence analysis of S9 gene and LI3 gene |
| Lm-S9-R | AACGTTTTCAGAACTGAGGTGC | Amplification and sequence analysis of S9 gene and LI3 gene |
| Lm-S9-F2 | CACATATCGACACTGGAGACTTTG | Sequence analysis of S9 gene and L13 gene |
| Lm-L10-F | CTGGAATCAAAGTCGACCCA | Amplification and sequence analysis of L10 gene |
| Lm-L10-R | GCAGCAGTTACGCCAAATTCTT | Amplification of L10 gene |
| Listeria_sp-L31-F | TGTTATAATATYTATACTGTGTGTAAAAGC | Amplification and sequence analysis of L31 gene |
| Listeria_sp-L31-R | TGAGACCGTAYTTTTTGTTGAAGC | Amplification and sequence analysis of L31 gene |

| Amino acid | Mass |
|---|---|
| A | 71.079 |
| R | 156.188 |
| N | 114.103 |
| D | 115.088 |
| C | 103.145 |
| Q | 128.13 |
| E | 129.114 |
| G | 57.052 |
| H | 137.141 |
| I | 113.159 |
| L | 113.159 |
| K | 128.174 |
| M | 131.198 |
| F | 147.176 |
| P | 97.116 |
| S | 87.078 |
| T | 101.104 |
| W | 186.213 |
| Y | 163.175 |
| V | 99.132 |

| | | Strains<br>Serotype | ATCC15313$^T$<br>1/2a | JCM2873<br>4d | JCM7671<br>1/2a | JCM7672<br>1/2c | JCM7673<br>3 | JCM7674<br>4a | JCM7675<br>4b | JCM7676<br>1/2b | JCM7677<br>3b | JCM7678<br>3c | JCM7680<br>4d | JCM7683<br>3b | ATCC51772<br>1/2a | ATCC19115<br>4b |
|---|---|---|---|---|---|---|---|---|---|---|---|---|---|---|---|---|
| Operon | Actual Measurement | Protein | | | | | | | | | | | | | | |
| S10 | ○ | S10 | 11551.43 | 11551.43 | 11551.43 | 11551.43 | 11551.43 | 11551.43 | 11551.43 | 11551.43 | 11551.43 | 11551.43 | 11551.43 | 11551.43 | 11551.43 | 11551.43 |
| | × | L3 | 22695.18 | 22695.18 | 22695.18 | 22695.18 | 22695.18 | 22695.18 | 22695.18 | 22695.18 | 22695.18 | 22695.18 | 22695.18 | 22695.18 | 22695.18 | 22695.18 |
| | × | L4 | 22472.97 | 22472.97 | 22472.97 | 22472.97 | 22472.97 | 22472.97 | 22472.97 | 22472.97 | 22472.97 | 22472.97 | 22472.97 | 22472.97 | 22472.97 | 22472.97 |
| | × | L23 | 10916.61 | 10916.61 | 10916.61 | 10916.61 | 10916.61 | 10930.64 | 10916.61 | 10916.61 | 10916.61 | 10916.61 | 10916.61 | 10916.61 | 10916.61 | 10916.61 |
| | × | L2 | 30374.96 | 30374.96 | 30374.96 | 30374.96 | 30374.96 | 30374.96 | 30374.96 | 30374.96 | 30374.96 | 30303.88 | 30374.96 | 30374.96 | 30374.96 | 30374.96 |
| | ○ | S19 | 10344.86 | 10344.86 | 10344.86 | 10344.86 | 10344.86 | 10344.86 | 10344.86 | 10344.86 | 10344.86 | 10344.86 | 10344.86 | 10344.86 | 10344.86 | 10344.86 |
| | ○ | L22 | 12743.72 | 12743.72 | 12743.72 | 12743.72 | 12743.72 | 12743.72 | 12743.72 | 12743.72 | 12743.72 | 12743.72 | 12743.72 | 12743.72 | 12743.72 | 12743.72 |
| | × | S3 | 24411.84 | 24411.84 | 24411.84 | 24411.84 | 24411.84 | 24411.84 | 24411.84 | 24411.84 | 24411.84 | 24411.84 | 24411.84 | 24411.84 | 24411.84 | 24411.84 |
| | × | L16 | 16138.96 | 16138.96 | 16138.96 | 16138.96 | 16138.96 | 16138.96 | 16138.96 | 16138.96 | 16138.96 | 16138.96 | 16138.96 | 16138.96 | 16138.96 | 16138.96 |
| | ○ | L29 | 7402.53 | 7402.53 | 7402.53 | 7402.53 | 7402.53 | 7402.53 | 7402.53 | 7402.53 | 7402.53 | 7402.53 | 7402.53 | 7402.53 | 7402.53 | 7402.53 |
| | × | S17 | 9905.45 | 9905.45 | 9905.45 | 9905.45 | 9905.45 | 9905.45 | 9905.45 | 9905.45 | 9905.45 | 9905.45 | 9905.45 | 9905.45 | 9905.45 | 9905.45 |
| spc | × | L14 | 13227.39 | 13227.39 | 13227.39 | 13227.39 | 13227.39 | 13227.39 | 13227.39 | 13227.39 | 13227.39 | 13227.39 | 13227.39 | 13227.39 | 13227.39 | 13227.39 |
| | ○ | L24 | 11180.22 | 11254.35 | 11180.22 | 11180.22 | 11180.22 | 11180.22 | 11194.25 | 11194.25 | 11194.25 | 11180.22 | 11194.25 | 11194.25 | 11180.22 | 11194.25 |
| | × | L5 | 19996.21 | 19996.21 | 19996.21 | 19996.21 | 19996.21 | 19996.21 | 19996.21 | 19996.21 | 19996.21 | 19996.21 | 19996.21 | 19996.21 | 19996.21 | 19996.21 |
| | ○ | S14 | 7016.49 | 7016.49 | 7016.49 | 7016.49 | 7016.49 | 7016.49 | 7016.49 | 7016.49 | 7016.49 | 7016.49 | 7016.49 | 7016.49 | 7016.49 | 7016.49 |
| | ○ | S8 | 14513.89 | 14513.89 | 14513.89 | 14513.89 | 14513.89 | 14513.89 | 14513.89 | 14513.89 | 14513.89 | 14513.89 | 14513.89 | 14513.89 | 14513.89 | 14513.89 |
| | ○ | L6 | 19270.08 | 19256.01 | 19270.08 | 19270.08 | 19270.08 | 19270.08 | 19256.01 | 19256.01 | 19256.01 | 19270.08 | 19256.01 | 19256.01 | 19270.08 | 19256.01 |
| | ○ | L18 | 13096.86 | 13096.86 | 13096.86 | 13096.86 | 13096.86 | 13096.86 | 13096.86 | 13096.86 | 13096.86 | 13096.86 | 13096.86 | 13096.86 | 13096.86 | 13096.86 |
| | △ | S5 | 17325.94 | 17325.94 | 17325.94 | 17325.94 | 17325.94 | 17325.94 | 17325.94 | 17325.94 | 17325.94 | 17325.94 | 17325.94 | 17325.94 | 17325.94 | 17325.94 |
| | ○ | L30 | 6362.55 | 6362.55 | 6362.55 | 6362.55 | 6362.55 | 6362.55 | 6362.55 | 6362.55 | 6362.55 | 6362.55 | 6362.55 | 6362.55 | 6362.55 | 6362.55 |
| | ○ | L15 | 15782.02 | 15782.02 | 15782.02 | 15782.02 | 15782.02 | 15782.02 | 15782.02 | 15782.02 | 15782.02 | 15782.02 | 15782.02 | 15782.02 | 15782.02 | 15782.02 |
| alpha | ○ | L36 | 4324.42 | 4324.42 | 4324.42 | 4324.42 | 4324.42 | 4324.42 | 4324.42 | 4324.42 | 4324.42 | 4324.42 | 4324.42 | 4324.42 | 4324.42 | 4324.42 |
| | △ | S13 | 13578.69 | 13578.69 | 13578.69 | 13578.69 | 13578.69 | 13578.69 | 13578.69 | 13578.69 | 13578.69 | 13578.69 | 13578.69 | 13578.69 | 13578.69 | 13578.69 |
| | ○ | S11 | 13655.65 | 13655.65 | 13655.65 | 13655.65 | 13655.65 | 13655.65 | 13655.65 | 13655.65 | 13655.65 | 13655.65 | 13655.65 | 13655.65 | 13655.65 | 13655.65 |
| | ○ | L17 | 15084.51 | 15084.51 | 15084.51 | 15084.51 | 15084.51 | 15084.51 | 15084.51 | 15084.51 | 15084.51 | 15084.51 | 15084.51 | 15084.51 | 15084.51 | 15084.51 |
| | × | L10 | 17433.93 | 17577.07 | 17563.04 | 17563.04 | 17563.04 | 17577.07 | 17577.07 | 17577.07 | 17577.07 | 17563.04 | 17577.07 | 17577.07 | 17563.04 | 17577.07 |
| | × | L21 | 11214.99 | 11214.99 | 11214.99 | 11214.99 | 11214.99 | 11214.99 | 11214.99 | 11214.99 | 11214.99 | 11214.99 | 11214.99 | 11214.99 | 11214.99 | 11214.99 |
| | ○ | S21 | 6715.79 | 6715.79 | 6715.79 | 6715.79 | 6715.79 | 6715.79 | 6715.79 | 6715.79 | 6715.79 | 6715.79 | 6715.79 | 6715.79 | 6715.79 | 6715.79 |
| | △ | L13 | 16200.61 | 16200.61 | 16200.61 | 16200.61 | 16200.61 | 16200.61 | 16184.61 | 16200.61 | 16200.61 | 16200.61 | 16184.61 | 16200.61 | 16200.61 | 16184.61 |
| | ○ | S9+Ac | 14283.40 | 14359.50 | 14283.40 | 14283.40 | 14283.40 | 14359.50 | 14359.50 | 14359.50 | 14359.50 | 14283.40 | 14359.50 | 14359.50 | 14283.40 | 14359.50 |

| | |
|---|---|
| lineage I | 1/2b, 3b, 4b, 4d, 4e |
| lineage II | 1/2a, 1/2c, 3a, 3c |
| lineage III | 4a, 4c |

Fig. 7A

| | | | | | | | | | | | | | | | |
|---|---|---|---|---|---|---|---|---|---|---|---|---|---|---|---|
| | Strain | ATCC15313T | ATCC51772 | JCM7671 | JCM7672 | JCM7673 | JCM7678 | JCM7677 | JCM7675 | ATCC19115 | JCM7680 | JCM7676 | JCM7683 | JCM2873 | JCM7674 |
| | Group | A | | | | | | B | | | | | | C | D |
| | Serotype | 1/2a | 1/2a | 1/2a | 1/2c | 3a | 3c | 3b | 4b | 4b | 4d | 1/2b | 3b | 4d | 4a |
| Biomarker | | L24 | 1 | 1 | 1 | 1 | 1 | 2 | 2 | 2 | 2 | 2 | 2 | 3 | 1 |
| | | L6 | 1 | 1 | 1 | 1 | 1 | 2 | 2 | 2 | 2 | 2 | 2 | 2 | 1 |
| | | L18 | 1 | 1 | 1 | 1 | 1 | 1 | 1 | 1 | 1 | 1 | 1 | 1 | 1 |
| | | L15 | 1 | 1 | 1 | 1 | 1 | 1 | 1 | 1 | 1 | 1 | 1 | 1 | 1 |
| | | S11 | 1 | 1 | 1 | 1 | 1 | 1 | 1 | 1 | 1 | 1 | 1 | 1 | 1 |
| | | S9+Ac | 1 | 1 | 1 | 1 | 1 | 2 | 2 | 2 | 2 | 2 | 2 | 2 | 2 |

Fig. 7B

| | Attribution No. | | |
|---|---|---|---|
| Biomarker | 1 | 2 | 3 |
| L24 | 11180.22 | 11194.25 | 11254.35 |
| L6 | 19270.08 | 19256.01 | |
| L18 | 13096.86 | 13110.89 | |
| L15 | 15782.02 | 15797.08 | |
| S11 | 13655.65 | 13674.66 | |
| S9+Ac | 14283.40 | 14359.50 | |

Fig. 8

| | | A | B | C | D | E | F | G | H | I | J | K | L | M |
|---|---|---|---|---|---|---|---|---|---|---|---|---|---|---|
| | | L. monocytogenes | | | | L. innocua | L. innocua | L. ivanovii | L. ivanovii | L. seeligeri | L. seeligeri | L. welshmeri | L. rocourtiae | L. grayi |
| | subspecies | | | | | | | ivanovii | londoniensis | | | | | |
| | strain | | | | | ATCC 33090T | GTC02960 | JCM76881 | ATCC49954 | JCM7679<br>JCM7682 | ATCC 35967T | GTC02963 | GTC16429T | ATCC19120T |
| | serotype | 1/2a, 1/2c<br>3a, 3c | 1/2b, 3b, 4b<br>4d, 4e | 4d | 4a | 6a | | | | | | | | |
| | Linage | II | I | I | III | | | | | | | | | |
| Biomarker | L24 | 11180.22 | 11194.25 | 11254.35 | 11180.22 | 11194.25 | 11194.25 | 11194.25 | 11194.25 | 11194.25 | 11194.25 | 11194.25 | 11558.65 | 11180.14 |
| | L6 | 19270.04 | 19256.01 | 19256.01 | 19270.04 | 19270.04 | 19270.04 | 19270.04 | 19270.04 | 19270.04 | 19270.04 | 19270.04 | 19097.81 | 19371.01 |
| | L18 | 13096.86 | 13096.86 | 13096.86 | 13096.86 | 13082.84 | 13096.86 | 13096.86 | 13082.84 | 13110.89 | 13110.89 | 13082.84 | 13068.99 | 13066.84 |
| | L15 | 15782.02 | 15782.02 | 15782.02 | 15782.02 | 15797.03 | 15797.03 | 15811.10 | 15796.09 | 15797.08 | 15797.08 | 15797.08 | 15743.01 | 15601.77 |
| | S11 | 13655.65 | 13655.65 | 13655.65 | 13655.65 | 13655.65 | 13655.65 | 13655.65 | 13655.65 | 13674.66 | 13674.66 | 13683.67 | 13608.66 | 13591.67 |
| | S9+Ac | 14283.40 | 14359.50 | 14359.50 | 14359.50 | 14359.50 | 14359.50 | 14359.50 | 14359.50 | 14302.45 | 14283.40 | 14302.45 | 14372.55 | 14330.55 |
| | L31 type B | 9259.36 | 9259.36 | 9259.36 | 9259.36 | 9259.36 | 9259.36 | 9290.37 | 9290.37 | 9290.37 | 9290.37 | 9290.37 | 9271.08 | 9327.44 |
| | S16 | 10234.94 | 10234.94 | 10234.94 | 10234.94 | 10252.96 | 10252.96 | 10234.94 | 10234.94 | 10234.94 | 10234.94 | 10234.94 | 10003.54 | 10230.88 |

The mass value of S11 of L. grayi was calculated assuming that the mass of Methyl group was added to the theoretical mass value.
The mass value of S11 of L. grayi was calculated assuming that the mass of Methyl group was added to the theoretical mass value.

Fig. 10

| sample | % | family | genus | species |
|---|---|---|---|---|
| L. innocua–ATCC33090T | 91.8 | Family IV Listeriaceae | Listeria | sp. |
| L. innocua–GTC02960 | 99.9 | Family IV Listeriaceae | Listeria | sp. |
| L. ivanovii–GTC02961 | 84.4 | Family IV Listeriaceae | Listeria | monocytogenes |
| L. ivanovii–ATCC49954T | 99.9 | Family IV Listeriaceae | Listeria | sp. |
| L. seeligeri–ATCC35967 | 91.8 | Family IV Listeriaceae | Listeria | sp. |
| L. welshimeri–GTC02963T | 97.2 | Family IV Listeriaceae | Listeria | sp. |
| L. rocouritiae–GTC16429T | 0 | | | |
| L. grayi–ATCC19120 | 99.9 | Family IV Listeriaceae | Listeria | grayi |
| L. seeligeri–JCM7679 | 81.1 | Family IV Listeriaceae | Listeria | monocytogenes |
| L. seeligeri–JCM7682 | 81.1 | Family IV Listeriaceae | Listeria | monocytogenes |

Fig. 12A

| | A | B | C | D | E | F | G | H | I | J | K | L | M |
|---|---|---|---|---|---|---|---|---|---|---|---|---|---|
| | L. monocytogenes | | | | L. innocua | | L. ivanovii | | L. seeligeri | | L. welshmeri | L. rocourtiae | L. grayi |
| subspecies | | | | | | | ivanovii | londoniensis | | | | | |
| strain | | | | | ATCC 33090T | GTC02960 | JCM7681T | ATCC49954 | JCM7679 JCM7682 | ATCC 35967T | GTC02963 | GTC16429T | ATCC19120T |
| serotype | 1/2a, 1/2c 3a, 3c | 1/2b, 3b, 4b 4d, 4e | 4d | 4a | 6a | | | | | | | | |
| Linage | II | I | I | III | | | | | | | | | |
| L24 | 1 | 2 | 3 | 1 | 2 | 2 | 2 | 2 | 2 | 2 | 2 | 1 | 1 |
| L6 | 1 | 2 | 2 | 1 | 1 | 1 | 1 | 1 | 1 | 1 | 1 | 3 | 4 |
| L18 | 1 | 1 | 1 | 1 | 3 | 1 | 1 | 3 | 2 | 2 | 3 | 4 | 4 |
| L15 | 1 | 1 | 1 | 1 | 2 | 2 | 3 | 2 | 2 | 2 | 2 | 4 | 5 |
| S11 | 1 | 1 | 1 | 1 | 1 | 1 | 1 | 1 | 2 | 2 | 3 | 4 | 5 |
| S9+Ac | 1 | 2 | 2 | 2 | 2 | 2 | 2 | 2 | 3 | 1 | 3 | 4 | 5 |
| L31 type B | 1 | 1 | 1 | 1 | 1 | 1 | 2 | 2 | 2 | 2 | 2 | 3 | 4 |
| S16 | 1 | 1 | 1 | 1 | 2 | 2 | 1 | 1 | 1 | 1 | 1 | 3 | 4 |

Fig. 12B

| Attr. No. | 1 | 2 | 3 | 4 | 5 |
|---|---|---|---|---|---|
| L24 | 11180.22 | 11194.25 | 11254.35 | 11558.65 | |
| L6 | 19270.04 | 19256.01 | 19097.81 | 19371.01 | |
| L18 | 13096.86 | 13110.89 | 13082.84 | 13066.84 | |
| L15 | 15782.02 | 15797.08 | 15811.1 | 15743.01 | 15601.77 |
| S11 | 13655.65 | 13674.66 | 13683.67 | 13591.66 | 13591.67 |
| S9+Ac | 14283.40 | 14359.50 | 14302.45 | 14372.55 | 14330.55 |
| L31 type B | 9259.36 | 9290.34 | 9271.3 | 9327.44 | |
| S16 | 10234.94 | 10252.97 | 10003.54 | 10230.88 | |

The mass value of S11 of L. grayi was calculated assuming that the mass of Methyl group was added to the theoretical mass value.

METHOD FOR DISCRIMINATING A MICROORGANISM

CROSS REFERENCE TO RELATED APPLICATIONS

This application is a Rule 53(b) Continuation of U.S. application Ser. No. 16/089,922 filed Sep. 28, 2018, which is a National Stage of International Application No. PCT/JP2016/060868 filed Mar. 31, 2016, the respective disclosures of which are incorporated herein by reference in their entirety.

INCORPORATION BY REFERENCE OF SEQUENCE LISTING

The content of the electronically submitted sequence listing, file name: Q281873_sequence listing as filed.XML; size: 444,906 bytes; and date of creation: Nov. 28, 2022, filed herewith, is incorporated herein by reference in their entirety.

TECHNICAL FIELD

The present invention relates to a method for discriminating a microorganism using mass spectrometry.

BACKGROUND ART

Homology analysis based on DNA base sequences has been known as one of methods for discriminating types of microorganisms and has been widely used for classification, identification or the like of microorganisms (see, for example, Patent Literature 1). In this method, DNA is first extracted from a test microorganism, and the DNA base sequence of a region, such as rRNA genes, existing in high conservation in all organisms is determined. Next, using the DNA base sequence, a database involving a large number of DNA base sequence data of known microorganisms is searched and a base sequence showing high similarity to the DNA base sequence of the test microorganism is selected. Then, the species from which the base sequence is derived is determined to be of the same species or closely related species to the test microorganism.

However, with such a method utilizing the DNA base sequence, it takes a relatively long time to extract DNA from a test microorganism and to determine a DNA base sequence, so that there is a problem that it is difficult to quickly identify the microorganisms.

Therefore, in recent years, a method of identifying a microorganism based on a mass spectrum pattern obtained by mass spectrometry of a test microorganism has been increasingly used. According to the mass spectrometry, analytical results can be obtained in a short time using a trace amount of a microorganism sample, and continuous analysis of multiple specimens is easily carried out, so that simple and quick microorganism identification is possible. In this method, a solution containing proteins extracted from a test microorganism, a suspension of a test microorganism or the like is analyzed by a mass spectrometer using a soft ionization method such as MALDI-MS (matrix assisted laser desorption ionization mass spectrometry). Note that the "soft" ionization method is an ionization method that hardly causes decomposition of a high-molecular weight compound. Then, the test microorganism is identified by comparing the obtained mass spectrum pattern with mass spectrum patterns of known microorganisms that have been involved in advance in a database in large numbers. Such a method is called a fingerprint method because a mass spectrum pattern is used as information (that is, a fingerprint) specific to each microorganism.

However, in the identification of microorganisms by the fingerprint method using mass spectrometry, it is possible to identify at the genus level or a relatively distant species level, but discrimination between closely related species and identification at the level of subspecies, pathogenic types, strains or the like as a classification level lower than the species are normally considered to be difficult. Further, in the fingerprint method, it is not determined from which protein each peak appearing on the mass spectra originates, leaving a problem of the theoretical basis of identification and reliability. Therefore, in order to solve the problem, utilizing the fact that about half of peaks obtained by mass spectrometry of microbial cells is derived from ribosomal proteins, a method of attributing the type of protein from which a peak is derived by associating a mass-to-charge ratio of the peak obtained by mass spectrometry with a calculated mass estimated from the amino acid sequence obtained by translating base sequence information of ribosomal protein genes have been developed (see Patent Literatures 2 and 3). According to this method, it is possible to perform microorganism identification with high reliability based on the theoretical basis by using mass spectrometry.

However, since peaks with different mass-to-charge ratios differ depending on the classification level of microorganisms (family, genus, species, subspecies, pathogenic type, serotype, strain, etc.), for example, in order to perform discrimination reproducibly at the pathogenic type or strain level, it is necessary to select marker peaks that can be used for discrimination at the pathogenic type or strain level to be identified. For example, as marker proteins for identifying and discriminating *Pseudomonas putida* and its analogous cells, 23 ribosomal subunit proteins (L5, L13, L14, L15, L18, L19, L20, L22, L23, L24, L28, L30, L35, L36, S7, S8, S10, S13, S14, S17, S19, S20, and S21) are available (Patent Literature 2).

CITATION LIST

Patent Literature

Patent Literature 1: JP 2006-191922 A
Patent Literature 2: JP 2007-316063 A
Patent Literature 3: JP 2013-085517 A

Non Patent Literature

Non Patent Literature 1: List of prokaryotic names with standing in nomenclature, [searched on Sep. 18, 2015], Internet <URL: http://www.bacterio.net/>
Non Patent Literature 2: BMC Genomics 2010, 11, 688
Non Patent Literature 3: JMM Case Reports, 2014, DOI 10.1099/jmmcr.0.003103
Non Patent Literature 4: Microbes Infect 2007, 9, 1236-1243
Non Patent Literature 5: Int J med Microbiol, 2011, 301, 79-96
Non Patent Literature 6: Appl Environ Micribiol, 2008, 74, 7629-7642
Non Patent Literature 7: Int J Food Microbiol 2001, 65:55-62
Non Patent Literature 8: J Clin Microbiol 2003, 41:757-762
Non Patent Literature 9: PLoS Pathog 2008, 4: e1000146

Non Patent Literature 10: Vet Microbiol, 2003, 92, 351-362.

Non Patent Literature 11: Appl Environ Micribiol, 2008, 74, 5402-5407

Non Patent Literature 12: J Clin Microbiol. 2012, 50, 2702-2707

Non Patent Literature 13: Int J Food Microbiol. 2015, 202, 1-9

Non Patent Literature 14: J Clin Microbiol. 2014, 52, 2371-2379

Non Patent Literature 15: J Clin Microbiol. 2004, 42, 3819-3822

SUMMARY OF INVENTION

Technical Problem

Incidentally, *Listeria monocytogenes* (hereinafter, "*Listeria*" is abbreviated as "L.") is known as one causative bacterium for food poisoning. *Listeria monocytogenes* is a bacterium belonging to the genus *Listeria* of gram-positive bacteria and has characteristics such as growth ability at low temperature (4° C.) and salt tolerance.

In the genus *Listeria*, 18 bacterial species have been discovered so far (Non Patent Literature 1) and numerous findings particularly about 8 species discovered in the 1960's and 1980's (*Listeria monocytogenes* (*L. monocytogenes*), *Listeria innocua* (*L. innocua*), *Listeria welshimeri* (*L. welshimeri*), *Listeria seeligeri* (*L. seeligeri*), *Listeria ivanovii* (*L. ivanovii*), *Listeria grayi* (*L. grayi*), *Listeria marthii* (*L. marthii*), and *Listeria rocourtiae* (*L. rocourtiae*)) have been reported as conventional species (Non Patent Literatures 2 and 3). According to such findings, *Listeria monocytogenes* and *Listeria ivanovii* have pathogenicity to animals and, in particular, *Listeria monocytogenes* has been reported to infect humans frequently via familiar uncooked ready-to-eat foods such as meat, dairy products, vegetables, etc., causing outbreaks of food poisoning. In addition, when pregnant women, newborns, elderly persons, and immunity deficient persons such as patients suffering from AIDS or cancer, and organ transplant patients are infected with *Listeria monocytogenes*, severe symptomatic listeriosis such as sepsis or meningitis is caused, which may lead to death. Further, in recent years, examples have also been reported in which *Listeria innocua* infected patients develop listeriosis (Non Patent Literature 3).

*Listeria monocytogenes* is known to have 13 serotypes (1/2a, 1/2b, 1/2c, 3a, 3b, 3c, 4a, 4ab, 4b, 4c, 4d, 4e, and 7), serotype 4b is the most common in epidemic outbreak cases, and serotype 1/2b and serotype 1/2a have been reported to be included (Non Patent Literature 4). In addition, *Listeria monocytogenes* can be genetically classified into four evolutionary lineages (lineages I, II, III, and IV) (Non Patent Literature 5). Serotypes frequently isolated from infected individuals belong to lineages I and II, and more specifically, serotypes 1/2b, 3b, 4b, 4d, and 4e belong to the lineage I and serotypes 1/2a, 1/2c, 3a, and 3c belong to the lineage II. On the other hand, serotypes 4a and 4c belong to the lineage III. The lineage IV is a recently proposed classification, and it has been reported that serotypes 4a, 4b, and 4c may belong to IV (Non Patent Literature 6). The lineages III and IV are less isolated from humans and are mainly detected from ruminants.

For this reason, among *Listeria* bacteria, *Listeria monocytogenes* need to be managed in the food field and the medical field as food poisoning bacteria harming humans, and development of a rapid detection method and an identification and discrimination technology has been desired.

Heretofore, as a method for discriminating serotypes of the genus *Listeria* and *Listeria monocytogenes*, pulse field gel electrophoresis (Non Patent Literature 7), multi-locus sequence typing method (Non Patent Literatures 8 and 9), microarray method (Non Patent Literature 10) and the like have been reported. However, each of these methods poses a problem that complicated operations are needed and a time is required.

Meanwhile, in the clinical field and the food field, a microorganism identification technology using matrix-assisted laser desorption/ionization time-of-flight mass spectrometry (MALDI-TOF MS) has been rapidly spreading in recent years. This is a method of identifying a microorganism based on a mass spectrum pattern obtained using a trace amount of a microorganism sample, and an analysis result can be obtained in a short time. In addition, continuous analysis of multiple specimens is easily carried out, so that simple and quick microorganism identification is possible.

For this reason, it has been attempted to discriminate *Listeria* bacteria using MALDI-TOF MS by a plurality of research groups (Non Patent Literatures 11 to 14). For example, Non Patent Literature 10 reports that *Listeria monocytogenes, Listeria innocua, Listeria welshimeri, Listeria ivanovii*, and *Listeria seeligeri* have been discriminated by pattern matching of all detected mass peaks with existing databases and calculating their scores. In addition, serotype 4a and serotype 4c of *Listeria monocytogenes* are distinguished by the fact that specific mass peaks (mass-to-charge ratios [m/z] 5590 and 11179) are detected as indexes (biomarkers).

On the other hand, according to Non Patent Literature 12, it is possible to identify species of *Listeria grayi* only, with 6 bacterial species of the genus *Listeria* being discriminated at the genus level. In Non Patent Literature 14, it has been reported that *Listeria monocytogenes* is classified into groups of serotype 1/2a, serotype 1/2b, and serotype 4b by using peaks of five detection masses (m/z 5594.85, 6184.39, 11871.31, 5601.21, 11199.33) as biomarkers.

As described above, although there are a plurality of reports on discrimination of bacterial species of *Listeria* bacteria and the serotype of *Listeria monocytogenes* by MALDI-TOF MS, from which protein each peak appearing on the mass spectra or each biomarker peak originates is not determined, lacking in the theoretical basis of identification and discrimination as well as reliability. In addition, the results of identification and discrimination are different from research group to research group, and unified views have not yet been obtained. In other words, a highly reliable marker protein that can be suitably used for discrimination of bacterial species and serotype of *Listeria* bacteria has not yet been established.

The present invention has been made in view of the above points, and an object of the present invention is to select a marker protein capable of reproducibly and quickly discriminating a bacterial species of the genus *Listeria* and to provide a method for discriminating a microorganism using the marker protein.

Solution to Problem

As a result of diligent discussion, the present inventors have found that *Listeria* bacteria can be discriminated by using at least one of 17 ribosomal proteins L3, L4, L23, L2, L24, L6, L18, S5, L15, S13, S11, L10, L21, L13, S9, L31, S16 as a marker protein for discriminating *Listeria* bacteria contained in a sample by mass spectrometry, and that *Listeria* bacteria can be discriminated reproducibly and quickly in particular by using at least one of 8 ribosomal proteins L24, L6, L18, L15, S11, S9, L31, S16 among these 17 ribosomal proteins.

That is, a method for discriminating a microorganism according to the present invention, which has been made to solve the above problem, includes:

a) a step of subjecting a sample containing a microorganism to mass spectrometry to obtain a mass spectrum;
b) a reading step of reading a mass-to-charge ratio m/z of a peak derived from a marker protein from the mass spectrum; and
c) a discrimination step of discriminating which bacterial species of *Listeria* bacteria the microorganism contained in the sample contains based on the mass-to-charge ratio m/z, wherein at least one of 17 ribosomal proteins L3, L4, L23, L2, L24, L6, L18, S5, L15, S13, S11, L10, L21, L13, S9, L31, S16 is used as the marker protein.

Particularly in the method for discriminating a microorganism, it is preferable to use at least one of 8 ribosomal proteins L24, L6, L18, L15, S9, L31, S16 among the 17 ribosomal proteins.

The method for discriminating a microorganism is suitable as a method for discriminating one of *Listeria monocytogenes* (*L. monocytogenes*), *Listeria innocua* (*L. innocua*), *Listeria welshimeri* (*L. welshimeri*), *Listeria seeligeri* (*L. seeligeri*), *Listeria ivanovii* (*L. ivanovii*), *Listeria grayi* (*L. grayi*), and *Listeria rocourtiae* (*L. rocourtiae*) as a bacterial species of the *Listeria* bacteria.

Specifically, the discrimination step discriminates whether or not *Listeria monocytogenes* is contained in the microorganism based on at least a mass-to-charge ratio m/z of a peak derived from each of the ribosomal proteins L15, S11, and S9, or a mass-to-charge ratio m/z of a peak derived from each of the ribosomal proteins L24, L6, L18, and S9, or a mass-to-charge ratio m/z of a peak derived from each of the ribosomal proteins S11, S9, L31, and S16, or a mass-to-charge ratio m/z of a peak derived from each of the ribosomal proteins L18, S9, L31, and S16, or a mass-to-charge ratios m/z of a peak derived from each of the ribosomal proteins L18, L15, and S9, or a mass-to-charge ratio m/z of a peak derived from each of the ribosomal proteins L24, L6, S11, and S9.

When the microorganism is discriminated as containing *Listeria monocytogenes*, the discrimination step further discriminates a lineage of *Listeria monocytogenes* based on a mass-to-charge ratio m/z of a peak derived from the ribosomal protein S9 and a mass-to-charge ratio m/z of a peak derived from at least one of the ribosomal proteins L24 and L6.

The discrimination step discriminates whether or not *Listeria innocua* is contained in the microorganism based on at least a mass-to-charge ratio m/z of a peak derived from the ribosomal protein S16 or a mass-to-charge ratio m/z of a peak derived from each of the ribosomal proteins L15 and L31. Then, when the microorganism is discriminated as containing *Listeria innocua*, the discrimination step further determines a strain of *Listeria innocua* based on at least a mass-to-charge ratio m/z of a peak derived from the ribosomal protein L18.

In addition, the discrimination step discriminates whether or not a strain of a group similar to a type strain (reference strain) of *Listeria innocua* in pattern of a mass-to-charge ratio of a ribosomal protein is contained in the microorganism based on at least a mass-to-charge ratio m/z of a peak derived from each of the ribosomal proteins L18 and S16, or a mass-to-charge ratios m/z of a peak derived from each of the ribosomal proteins L18 and L31.

Further, the discrimination step classifies a strain contained in the microorganism into a group similar to a type strain of *Listeria innocua* in pattern of a mass-to-charge ratio of a ribosomal protein or a non-similar group based on at least a mass-to-charge ratio m/z of a peak derived from each of the ribosomal proteins L18 and S16 or a mass-to-charge ratio m/z of a peak derived from each of the ribosomal proteins L18 and L31.

Also, the discrimination step discriminates whether or not *Listeria ivanovii* is contained in the microorganism based on at least a mass-to-charge ratio m/z of a peak derived from the ribosomal proteins S9 and L31.

Further, when the microorganism is discriminated as containing *Listeria ivanovii*, the discrimination step further discriminates a subspecies of *Listeria ivanovii* based on at least one of a mass-to-charge ratio m/z of a peak derived from the ribosomal protein L18 and a mass-to-charge ratio m/z of a peak derived from the ribosomal protein L15.

Then, the discrimination step discriminates whether or not *Listeria ivanovii ivanovii* (*L. ivanovii ivanovii*) as a subspecies of *Listeria ivanovii* is contained in the microorganism based on at least a mass-to-charge ratio m/z of a peak derived from the ribosomal protein L15 or a mass-to-charge ratio m/z of a peak derived from each of the ribosomal proteins L18 and L31, and discriminates whether or not *Listeria ivanovii londiniensis* (*L. ivanovii londiniensis*) as a subspecies of *Listeria ivanovii* is contained in the microorganism based on at least a mass-to-charge ratio m/z of a peak derived from each of the ribosomal proteins L18, S9, and L31, or a mass-to-charge ratio m/z of a peak derived from each of the ribosomal proteins L15, S11, and L31, or a mass-to-charge ratio m/z of a peak derived from each of the ribosomal proteins L15, S9, and L31, or a mass-to-charge ratio m/z of a peak derived from each of the ribosomal proteins L18, S11, and L31.

Further, the discrimination step discriminates whether or not *Listeria seeligeri* is contained in the microorganism based on a mass-to-charge ratio m/z of a peak derived from the ribosomal protein S9 and a mass-to-charge ratio m/z of a peak derived from at least one of the ribosomal proteins L18 and S11.

When the microorganism is discriminated as containing *L. seeligeri*, the discrimination step further determines a strain of *L. seeligeri* based on at least the mass-to-charge ratio m/z of a peak derived from the ribosomal protein S9.

The discrimination step discriminates whether or not a strain of a group similar to a type strain of *Listeria seeligeri* in pattern of a mass-to-charge ratio of a ribosomal protein is contained in the microorganism based on at least a mass-to-charge ratio m/z of a peak derived from the ribosomal protein S9 and a mass-to-charge ratio m/z of a peak derived from at least one of the ribosomal proteins L24, L18, L15, S11, and L31.

The discrimination step classifies a strain contained in the microorganism into a group similar to a type strain of *Listeria seeligeri* in pattern of a mass-to-charge ratio of a ribosomal protein or a non-similar group based on at least a mass-to-charge ratios m/z of a peak derived from each of the ribosomal proteins S9 and L18 or a mass-to-charge ratio m/z of a peak derived from each of the ribosomal proteins S9 and S1.

Further, the discrimination step discriminates whether or not *Listeria welshimeri* is contained in the microorganism based on at least a mass-to-charge ratio m/z of a peak derived from the ribosomal protein S11 or a mass-to-charge ratio m/z of a peak derived from each of the ribosomal proteins L18 and S9.

In addition, the discrimination step discriminates whether the bacterial species of the *Listeria* bacteria contained in the microorganism is *Listeria grayi* or *Listeria rocourtiae* based on a mass-to-charge ratio m/z of a peak derived from at least one of the ribosomal proteins L6, L15, S11, S9, L31, and S16.

Also, in the above method for discriminating a microorganism according to the present invention, the discrimination step may discriminate which bacterial species of *Listeria* bacteria the microorganism contained in the sample contains using a cluster analysis in which at least a mass-to-charge ratio m/z of a peak of each of the ribosomal proteins L24, L18, S9, and L31 and a mass-to-charge ratio m/z of a peak of one of the ribosomal proteins L6, L15, and S11, or a mass-to-charge ratio m/z of a peak of each of the ribosomal proteins L24, L18, S9, and S16 and a mass-to-charge ratio m/z of a peak of one of the ribosomal proteins L6, L15, and S11 are used as indexes, and in particular, if the cluster analysis in which all of the mass-to-charge ratios m/z of peaks derived from 8 marker proteins (L24, L18, S9, L31, S16, L6, L15, S11) are used as indexes, it is possible to accurately discriminate which bacterial species of *Listeria* bacteria the microorganism contained in the sample is.

In this case, it is preferable to further include a step of creating a dendrogram representing a discrimination result by the cluster analysis.

Advantageous Effects of Invention

In the method for discriminating a microorganism according to the present invention described above, a ribosomal protein having a mutation peculiar to a bacterial species of the genus *Listeria* is used as a marker protein, and therefore, the bacterial species of the genus *Listeria* can be reproducibly and quickly discriminated.
By using a ribosomal protein having a mutation peculiar to a bacterial species of the genus *Listeria* as a marker protein and carrying out cluster analysis using a mass-to-charge ratio m/z of a peak derived from the marker protein on the mass spectra as an index, the bacteria of the genus *Listeria* contained in a plurality of samples can be collectively discriminated.

BRIEF DESCRIPTION OF DRAWINGS

FIG. 3 is a diagram showing a list of bacterial species names and strain names of the genus *Listeria* used in Example.

FIG. 4 is a diagram showing a list of primers used in Example. In particular, FIG. 4 shows catggcggat gttcaggtaa (SEQ ID NO: 305), ctccttccag aataacgggt (SEQ ID NO: 306), agcagcacaa aacgtggtac (SEQ ID NO: 307), aaggaggact aacgaatgcc (SEQ ID NO: 308), tgcacgcaac ttacaaggca (SEQ ID NO: 309), cggacgcaat aaccaaggta (SEQ ID NO: 310), aatgaacccg aacgatcacc (SEQ ID NO: 311), tacaagcgca aaagccgttg (SEQ ID NO: 312), gtgcagctaa ccgtgtgaat (SEQ ID NO: 313), aggcggaact gaagttgcat (SEQ ID NO: 314), acccgttatt ctggaaggag (SEQ ID NO: 315), aaggcattac acccatggca (SEQ ID NO: 316), ctcgtccatt gtctgcaact (SEQ ID NO: 317), caaacgtaat gctamttgac cc (SEQ ID NO: 318), cgtggtaact atacgttggg t (SEQ ID NO: 319), gactggcgaa cgtgtaatca (SEQ ID NO: 320), tcctgcaaac acwcaagtga tt (SEQ ID NO: 321), ggagggacat attacatgcc tg (SEQ ID NO: 322), ttaatcggac gccctcaa (SEQ ID NO: 323), ctctaccaaa cgcgatgttc (SEQ ID NO: 324), ggaaacacag agctagacaa gg (SEQ ID NO: 325), cctgacacgc ggaagaatta (SEQ ID NO: 326), aaggcccgtc caaaacagta (SEQ ID NO: 327), cagcgatgat gccaagtatg (SEQ ID NO: 328), gaagcagttt cacttggagc (SEQ ID NO: 329), aactggctga ccttggctta (SEQ ID NO: 330), cccctgtgat ggcgagtctt (SEQ ID NO: 331), tcttctcgca taacatcgac ttgaa (SEQ ID NO: 332), tgaaggattt aagtgagtgc atgt (SEQ ID NO: 333), cgcatcgctt gtttcatatc t (SEQ ID NO: 334), ttcgggagct aatttgtttc aa (SEQ ID NO: 335), aacgttttca gaactgaggt gc (SEQ ID NO: 336), cacatatcga cactggagac tttg (SEQ ID NO: 337), ctggaatcaa agtcgaccca (SEQ ID NO: 338), gcagcagtta cgccaattc tt (SEQ ID NO: 339), tgttataata tytatactgt gtgtaaaagc (SEQ ID NO: 340), and tgagaccgta ytttttgttg aagc (SEQ ID NO: 341).

FIG. 5 is a diagram showing the mass of each amino acid.

FIG. 6 is a diagram showing a list of theoretical mass values of respective proteins in a *Listeria monocytogenes* strain used in Example.

FIG. 7A is a diagram showing a list of attribution of actual measurement values of respective ribosomal proteins in the strain used in Example.

FIG. 7B is a diagram showing the relationship between the attribution number in FIG. 7A and the theoretical mass value of each ribosomal protein.

FIG. 8 is a diagram showing a list of theoretical mass values of respective proteins in a species of the genus *Listeria* used in Example.

FIG. 10 is an analysis result based on SARAMIS.

FIGS. 11A-1 and 11A-2 show a peak chart obtained by MALDI-TOF MS measurement (part 1).

FIGS. 11B-1 and 11B-2 is a peak chart obtained by MALDI-TOF MS measurement (part 2).

FIG. 12A is an attribution result by actual measurement values of 8 ribosomal proteins.

FIG. 12B is a table showing the relationship between the attribution number shown in FIG. 12A and the theoretical mass value.

DESCRIPTION OF EMBODIMENTS

Hereinafter, a specific embodiment of a method for discriminating a microorganism according to the present invention will be described.

Figure 1:
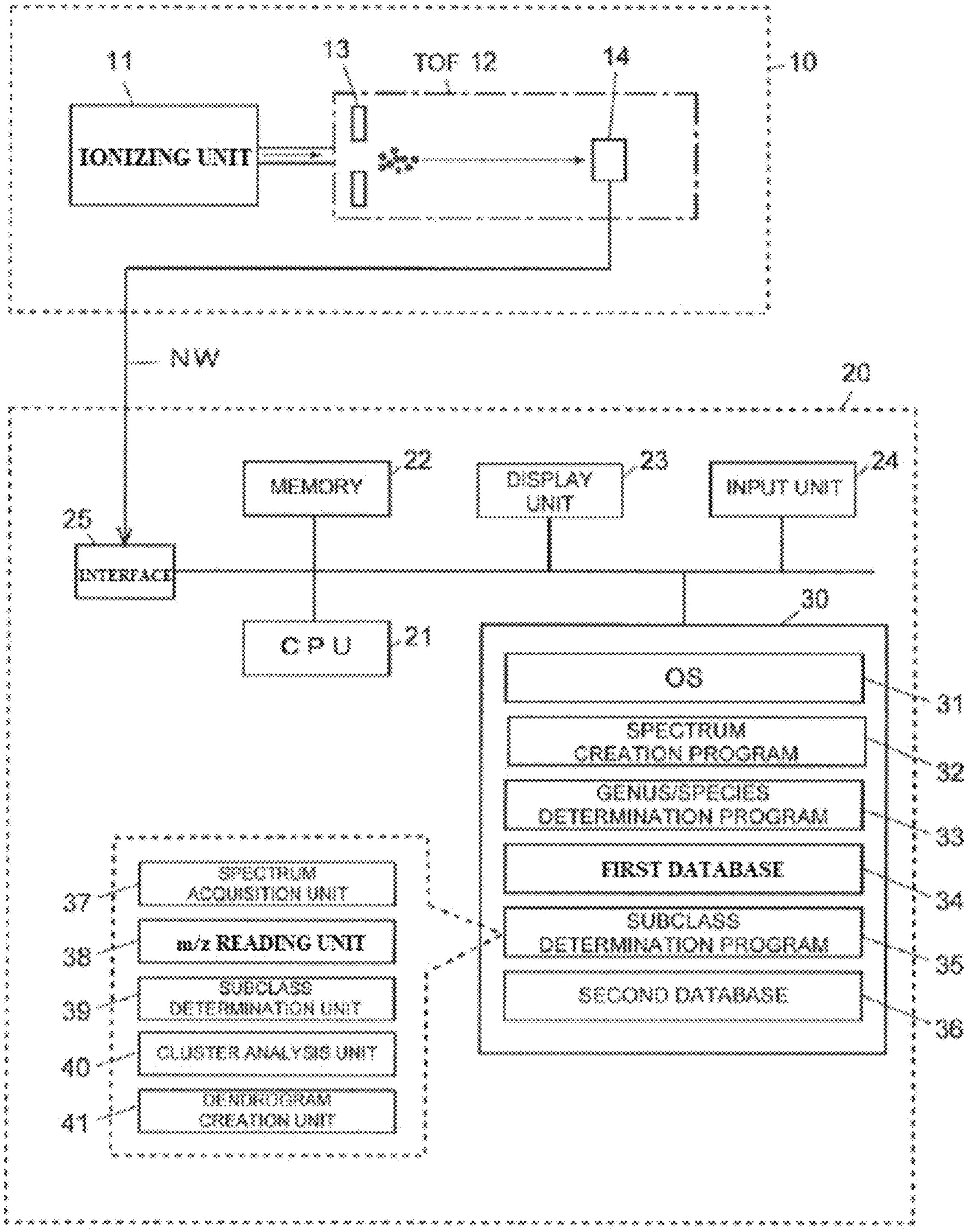
FIG. 1 is a block diagram showing principal units of a microorganism discrimination system used in a method for discriminating a microorganism according to the present invention.

FIG. 1 is an overall view of a microorganism discrimination system used by the method for discriminating a microorganism according to the present invention. The microorganism discrimination system is roughly made up of a mass spectrometry unit 10 and a microorganism determination unit 20. The mass spectrometry unit 10 includes an ionization unit 11 that ionizes molecules and atoms in a sample by a matrix-assisted laser desorption ionization (MALDI) method and a time-of-flight mass separator (TOF) 12 that separates various ions emitted from the ionization unit 11 in accordance with the mass-to-charge ratio.

The TOF 12 includes an extraction electrode 13 that extracts ions from the ionization unit 11 to guide the ions into an ion flight space in the TOF 12 and a detector 14 that detects ions mass-separated in the ion flight space.

The substance of the microorganism determination unit 20 is a computer such as a workstation or a personal computer, and a central processing unit (CPU) 21 as a central processing unit, a memory 22, a display unit 23 including a liquid crystal display (LCD), an input unit 24 including a keyboard, a mouse and the like, and a storage unit 30 including a mass storage device such as a hard disk and a solid state drive (SSD) are connected to each other. An operating system (OS) 31, a spectrum creation program 32, a genus/species determination program 33, and a subclass determination program 35 (program according to the present invention) are stored in the storage unit 30 and also, a first database 34 and a second database 36 are stored. The microorganism determination unit 20 further includes an interface (I/F) 25 to control direct connection with an external device and connection via a network such as a Local Area Network (LAN) with an external device or the like and is connected to the mass spectrometry unit 10 from the interface 25 via a network cable NW (or wireless LAN).

In FIG. 1, a spectrum acquisition unit 37, an m/z reading unit 38, a subclass determination unit 39, a cluster analysis unit 40, and the dendrogram (lineage diagram) creation unit 41 are shown as relating to the subclass determination program 35. Basically, these units are functional means implemented by software by the subclass determination program 35 being executed by the CPU 21. The subclass determination program 35 is not necessarily a single program, but may be a function incorporated into a portion of a program for controlling the genus/species determination program 33 or the mass spectrometry unit 10 and its form is not particularly limited. As the genus/species determination program 33, for example, a program for performing microorganism identification by a conventional fingerprint method or the like can be used.

Also, in FIG. 1, the spectrum creation program 32, the genus/species determination program 33, the subclass determination program 35, the first database 34, and the second database 36 are mounted on the terminal operated by the user, but at least a portion or all of these units may be provided in another device connected to the terminal via a computer network so that processing by a program and/or access to a database provided in the other device is performed according to instructions from the terminal.

A large number of mass lists related to known microorganisms are registered in the first database 34 of the storage unit 30. These mass lists enumerate the mass-to-charge ratios of ions detected upon mass spectrometry of a certain microorganism cell and include, in addition to the information of the mass-to-charge ratios, at least information (classification information) of the classification group to which the microbial cell belongs (family, genus, species, etc.). Such mass lists are desirably created based on data (actual measurement data) obtained by actual mass spectrometry of various microbial cells in advance by the same ionization method and mass separation method as those by the mass spectrometry unit 10.

When creating a mass list from the actual measurement data, a peak appearing in a predetermined mass-to-charge ratio range is first extracted from the mass spectrum acquired as the actual measurement data. At this point, by setting the mass-to-charge ratio range to about 2,000 to 35,000, protein-derived peaks can be mainly extracted. Also, by extracting only peaks whose peak height (relative intensity) is equal to or greater than a predetermined threshold, undesirable peaks (noise) can be excluded. Since the ribosomal protein group is expressed in a large amount in the cell, most of the mass-to-charge ratios listed in the mass list can be derived from the ribosomal proteins by setting the threshold appropriately. Then, the mass-to-charge ratios (m/z) of the peaks extracted in the above manner are listed for each cell and registered in the first database 34 after adding the classification information and the like. In order to suppress variations in gene expression due to culture conditions, it is desirable to standardize culture conditions in advance for each microbial cell used for collecting actual measurement data.

Information about marker proteins to discriminate known microorganisms at a level lower than the classification level discriminable by the genus/species determination program 33 is registered in the second database 36 of the storage unit 30. That is, information about marker proteins to discriminate the classification subordinate to the genus (species, subspecies, pathogenic type, serotype, strain, etc.) when the genus/species determination program 33 can discriminate the genus of a known microorganism and to discriminate the classification subordinate to the species (subspecies, pathogenic type, serotype, strain, etc.) when the species of a known microorganism can be discriminated is registered. Information about the marker protein includes at least information about the mass-to-charge ratio (m/z) of the marker protein in the known microorganism. In the second database 36 according to the present embodiment, as information about marker proteins to discriminate which of 7 species (*Listeria monocytogenes* (*L. monocytogenes*), *Listeria innocua* (*L. innocua*), *Listeria ivanovii* (*L. ivanovii*), *Listeria seeligeri* (*L. seeligeri*), *Listeria welshimeri* (*L. welshimeri*), *Listeria rocourtiae* (*L. rocourtiae*), and *Listeria grayi* (*L. grayi*)) of the genus *Listeria* the test microorganism is, mass-to-charge ratio values of at least 8 ribosomal proteins, the mass-to-charge ratio value of L24 (m/z 11180.22, 11194.25, 11254.35, 11558.65), the mass-to-charge ratio value of L6 (m/z 19270.04, 19256.01, 19097.81, 19371.01), the mass-to-charge ratio value of L18 (m/z 13096.86, 13110.89, 13082.84, 13066.84), the mass-to-charge ratio value of L15 (m/z 15782.02, 15797.08, 15811.1, 15743.01, 15601.77), the mass-to-charge ratio value of S11 (m/z 13655.65, 13674.66, 13683.67, 13591.66, 13591.67), the mass-to-charge ratio value of S9+Ac (m/z 14283.40, 14359.50, 14302.45, 14372.55, 14330.55), the mass-to-charge ratio value of L31 type B (m/z 9259.36, 9290.34, 9271.3, 9327.44), and the mass-to-charge ratio value of S16 (m/z 10234.94, 10252.97, 10003.54, 10230.88) are stored. The subclass determination program 35 uses at least one of these 8 ribosomal proteins to discriminate which of the 7 bacterial species of *Listeria* genus is the test microorganism.

Specifically, based on at least the mass-to-charge ratio m/z of a peak derived from each of the ribosomal proteins L15, S11, and S9, or the mass-to-charge ratio m/z of a peak derived from each of the ribosomal proteins L24, L6, L18, and S9, or the mass-to-charge ratio m/z of a peak derived from each of the ribosomal proteins S11, S9, L31, and S16, or the mass-to-charge ratio m/z of a peak derived from each of the ribosomal proteins L18, S9, L31, and S16, or the mass-to-charge ratio m/z of a peak derived from each of the ribosomal proteins L18, L15, and S9, or the mass-to-charge ratio m/z of a peak derived from each of the ribosomal proteins L24, L6, S11, and S9, whether or not *Listeria monocytogenes* is contained in the test microorganism is discriminated.

Also, based on at least the mass-to-charge ratio m/z of a peak derived from the ribosomal protein S16 or the mass-to-charge ratio m/z of a peak derived from each of the ribosomal proteins L15 and L31, whether or not *Listeria innocua* is contained in the test microorganism is discriminated.

Further, based on the mass-to-charge ratio m/z of a peak derived from the ribosomal proteins S9 and L31, whether or not *Listeria ivanovii* is contained in the test microorganism is discriminated.

Further, based on the mass-to-charge ratio m/z of a peak derived from the ribosomal protein S9 and the mass-to-charge ratio m/z of a peak derived from at least one of the ribosomal proteins L18 and S11, whether or not *Listeria seeligeri*, is contained in the test microorganism is discriminated.

Further, based on at least the mass-to-charge ratio m/z of a peak derived from the ribosomal protein S11 or the mass-to-charge ratios m/z of a peak derived from each of the ribosomal proteins L18 and S9, whether or not *Listeria welshimeri* is contained in the test microorganism is discriminated.

As described above, the above 8 ribosomal proteins can be used as marker proteins to discriminate the bacterial species of the genus *Listeria* alone or as a combination of a plurality of ribosomal proteins and therefore, the value of the mass-to-charge ratio is stored in the second database 36 together with information about the bacterial species.

When discriminated that *Listeria monocytogenes* is contained in the test microorganism, based on the mass-to-charge ratio m/z of a peak derived from the ribosomal protein S9 and the mass-to-charge ratio m/z of a peak derived from at least one of the ribosomal proteins L24 and L6, the lineage of *Listeria monocytogenes* can be discriminated. Thus, the ribosomal proteins S9, L24, and L6 can also be used as marker proteins to discriminate *Listeria monocytogenes* lineage (Lineage), and the ribosomal proteins L24, L18, L15, S11, S9, and L31 can also be used as marker proteins to discriminate the serotype of *Listeria monocytogenes*. Therefore, the values of the mass-to-charge ratio of these ribosomal proteins are also stored in the second database 36 as information about the marker proteins for discriminating the lineage and serotype of *Listeria monocytogenes.*

In addition, when discriminated that *Listeria innocua* is contained in the test microorganism, the strain of the *innocua* can be determined based on at least the mass-to-charge ratio m/z of a peak derived from the ribosomal protein L18.

Further, based on at least the mass-to-charge ratios m/z of a peak derived from each of the ribosomal proteins L18 and S16, or the mass-to-charge ratios m/z of a peak derived from each of the ribosomal proteins L18 and L31, whether or not a strain (for example, *Listeria innocua* ATCC33090T (*L. innocua* ATCC33090T)) as a group similar to the type strain (reference strain) of *Listeria innocua* in pattern of the mass-to-charge ratio of the ribosomal protein is contained in the microorganism can be discriminated.

Further, based on at least the mass-to-charge ratio m/z of a peak derived from each of the ribosomal proteins L18 and S16, or the mass-to-charge ratio m/z of a peak derived from each of the ribosomal proteins L18 and L31, the strains contained in the microorganism can be classified into a group similar to the type strain of *Listeria innocua* in pattern of the mass-to-charge ratio of the ribosomal protein and a non-similar group.

Therefore, the values of the mass-to-charge ratios of these ribosomal proteins L18, S16, and L31 are also stored in the second database 36 as information about the marker proteins for discriminating the strain of *Listeria innocua.*

In addition, when discriminated that *Listeria ivanovii* is contained in the test microorganism, based on at least one of the mass-to-charge ratio m/z of a peak derived from the ribosomal protein L18 and the mass-to-charge ratio m/z of a peak derived from the ribosomal protein L15, the subspecies of *Listeria ivanovii* can be discriminated.

Further, based on at least the mass-to-charge ratio m/z of a peak derived from the ribosomal protein L15 or the mass-to-charge ratio m/z of a peak derived from each of the ribosomal proteins L18 and L31, whether or not *Listeria ivanovii ivanovii* (*L. ivanovii ivanovii*) as a subspecies of *Listeria ivanovii* is contained in the test microorganism can be discriminated.

Further, based on at least the mass-to-charge ratio m/z of a peak derived from each of the ribosomal proteins L18, S9, and L31, or the mass-to-charge ratio m/z of a peak derived from each of the ribosomal proteins L15, S11, and L31, or the mass-to-charge ratio m/z of a peak derived from each of the ribosomal proteins L15, S9, and L31, or the mass-to-charge ratio m/z of a peak derived from each of the ribosomal proteins L18, S11, and L31, whether or not *Listeria ivanovii londiniensis* (*L. ivanovii londiniensis*) as a subspecies of *Listeria ivanovii* is contained in the test microorganism can be discriminated.

Therefore, the values of the mass-to-charge ratios of the ribosomal proteins L18, S9, L31, L15, and S11 are also stored in the second database 36 as information about the marker proteins for discriminating the subspecies of *Listeria ivanovii.*

Also, based on the mass-to-charge ratio m/z of a peak derived from at least one of the ribosomal proteins L6, L15, S11, S9, L31, and S16, whether the bacterial species of *Listeria* bacteria contained in the test microorganism is *Listeria grayi* or *Listeria rocourtiae* can be discriminated.

Therefore, the values of the mass-to-charge ratios of the ribosomal proteins L6, L15, S11, S9, L31, and S16 are stored in the second database 36 as information about the marker proteins for discriminating *Listeria grayi* or *Listeria rocourtiae.*

The fact that the 8 ribosomal proteins described above can be used for discrimination of bacterial species of the genus *Listeria*, discrimination of lineage and serotype of *Listeria monocytogenes*, determination of strains of *Listeria innocua* and grouping of strains, and discrimination of subspecies of *Listeria ivanovii* and the like is derived from the result of determining the mass-to-charge ratios of 8 ribosomal proteins for each bacterial species or each strain of the genus *Listeria* and attributing the mass-to-charge ratios of 8 ribosomal proteins of each bacterial species or each strain. For example, with respect to *Listeria innocua*, ribosomal proteins useful for grouping the strains are selected by comparing the mass-to-charge ratios of 8 ribosomal proteins of *Listeria innocua* ATCC33090T (*L. innocua* ATCC33090T) as the type strain and the mass-to-charge ratios of 8 ribosomal proteins of *Listeria innocua* GTCO2960 (*L. innocua* GTCO2960), which is not the type strain (for details, refer to Examples to be described below, FIG. 8 showing the theoretical mass values of 8 ribosomal proteins, FIG. 12A showing the attribution results based on actual measurement values of 8 ribosomal proteins, and the like)).

The value of the mass-to-charge ratio of the marker proteins stored in the second database 36 is desirably selected by comparing the calculated mass obtained by translating the base sequence of each marker protein into an amino acid sequence with the mass-to-charge ratio detected by actual measurement. The base sequence of the marker protein may be, in addition to determining by sequencing, acquired from a public database, for example, a database or the like of National Center for Biotechnology Information (NCBI) and used. When calculating the calculated mass from the amino acid sequence, it is desirable to consider cleavage of the N-terminal methionine residue as a post-translational modification. More specifically, when the penultimate amino acid residue is Gly, Ala, Ser, Pro, Val, Thr, or Cys, the theoretical value is calculated assuming that the N-terminal methionine is cleaved. In addition, molecules added with protons are actually observed by MALDI-TOF MS and thus, it is desirable to determine the calculated mass by factoring in protons (that is, the theoretical value of the mass-to-charge ratio of ions obtained when each protein is analyzed by MALDI-TOF MS).

Note that a portion or all of the information about the marker proteins stored in the second database 36 may also be stored in the first database 34.

Figure 2:
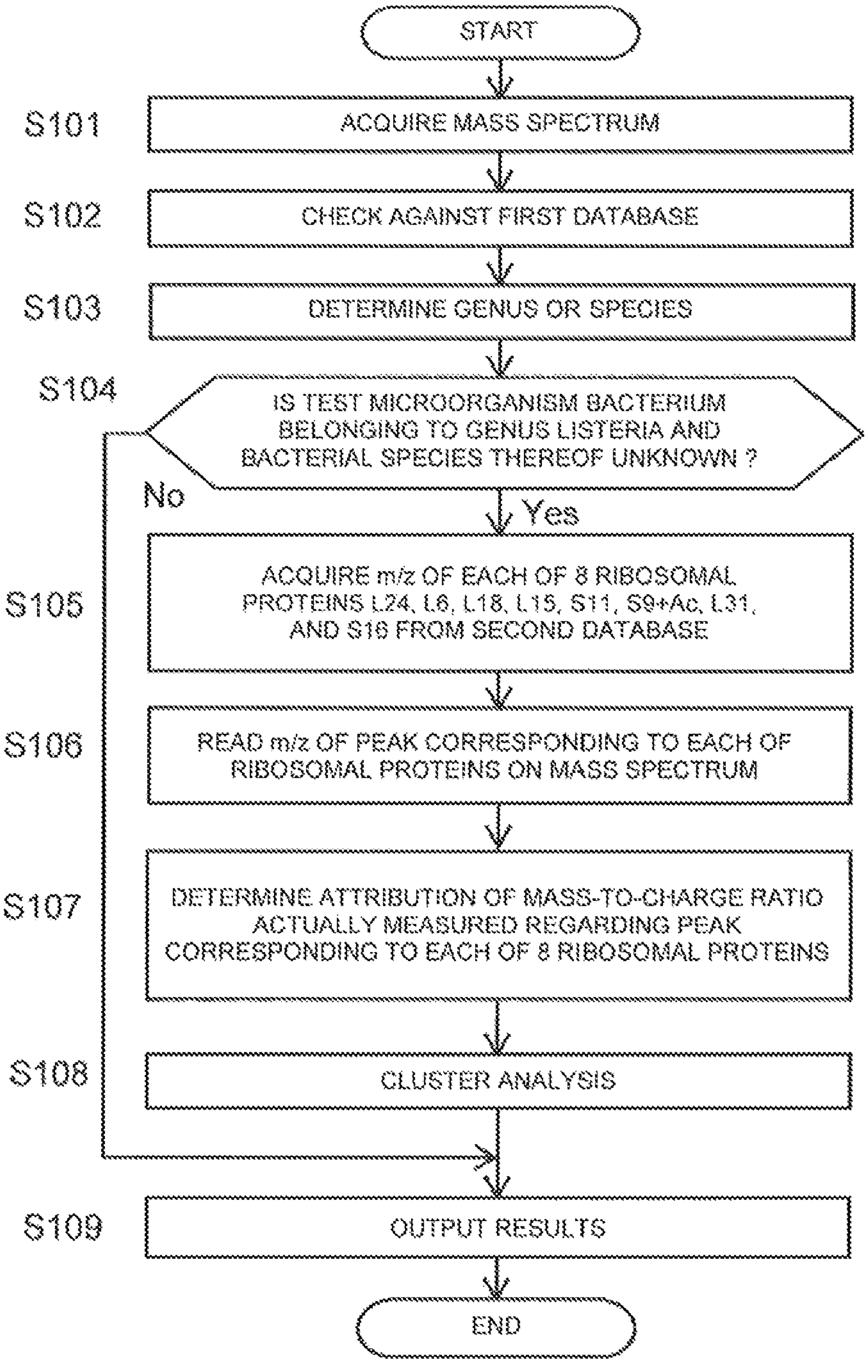
FIG. 2 is a flowchart showing an example of a procedure for the method for discriminating a microorganism according to the present invention.

The discrimination procedure of bacterial species of the genus *Listeria* using a microorganism discrimination system according to the present embodiment will be described with reference to the flowchart shown in FIG. 2.

First, the user prepares a sample containing constituent components of a test microorganism and sets the sample to the mass spectrometry unit 10 to perform mass spectrometry. At this point, in addition to a cell extract or a cellular component such as a ribosomal protein purified from a cell extract, bacterial cells or a cell suspension may be used as it is.

The spectrum creation program 32 acquires a detection signal obtained from the detector 14 of the mass spectrometry unit 10 via the interface 25 and creates a mass spectrum of the test microorganism based on the detection signal (step S101).

Next, the genus/species determination program 33 checks the mass spectrum of the test microorganism against a mass list of known microorganisms recorded in the first database 34 and extracts a mass list of known microorganisms having a mass-to-charge ratio pattern similar to the mass spectrum of the test microorganism, for example, a mass list including peaks that coincide with each peak in the mass spectrum of the test microorganism within a predetermined error range (step S102). Subsequently, the genus/species determination program 33 refers to the classification information stored in the first database 34 in association with the mass list extracted in step S102, thereby determining the classification (genus or species) of the known microorganism corresponding to the mass list (step S103). If the test microorganism is not bacteria belonging to the genus *Listeria*, or the test microorganism is a bacterium belonging to the genus *Listeria* and the bacterial species thereof is determined (No in step S104), the classification is output the display unit 23 as a classification of the test microorganism (step S112) before the discrimination processing is terminated. On the other hand, if the species is a bacterium belonging to the genus *Listeria* and the bacterial species thereof is unknown (Yes in step S104), then the processing proceeds to the discrimination processing by the subclass determination program 35. If it is determined in advance that the sample contains *Listeria* bacteria by other methods, the processing may proceed to the subclass determination program 35 without using the genus/species determination program using a mass spectrum.

In the subclass determination program 35, first the subclass determination unit 39 reads the mass-to-charge ratio values of the 8 ribosomal proteins L24, L6, L18, L15, S11, S9+Ac, L31 type B, and S16 as marker proteins from the second database 36 (step S105). Subsequently, the spectrum acquisition unit 37 acquires the mass spectrum of the test microorganism created in step S101. Then, the m/z reading unit 38 selects peaks appearing in the mass-to-charge ratio range stored in the second database 36 in association with each of the marker proteins on the mass spectrum as peaks corresponding to each of the marker proteins and reads the mass-to-charge ratios thereof (step S106). Then, the cluster analysis is performed using the read mass-to-charge ratio as an index. More specifically, the subclass determination unit 39 compares the mass-to-charge ratio with the value of the mass-to-charge ratio of each marker protein read out from the second database 36 and determines the attribution of the protein with respect to the read mass-to-charge ratio (Step S107). Then, the cluster analysis is performed based on the determined attribution to determine the species of the test microorganism (step S108), and the determined species is output to the display unit 23 as the discrimination result of the test microorganisms (step S109).

In the foregoing, an embodiment to carry out the present invention has been described above with reference to the drawings, but the present invention is not limited to the above embodiment and appropriate modifications are permitted within the scope of the spirit of the present invention.

For example, in the above embodiment, for convenience of description, to which species of the genus *Listeria* the test microorganism belongs is determined and then, the serotype and lineage of *Listeria monocytogenes* are discriminated, but the determination and the discrimination may be performed simultaneously. Also, the discrimination of serotypes and lineage of bacterial species of *Listeria monocytogenes* may be omitted.

EXAMPLE

Hereinafter, an experiment conducted to demonstrate the selection procedure of marker proteins in the present invention and the effect of the present invention will be described.

(1) Strains Used and Culture Medium

In order to construct a protein mass database, 14 strains of *Listeria monocytogenes*, two strains of *Listeria innocua*, two strains of *Listeria ivanovii*, three strains of *Listeria seeligeri*, one strain of each of *Listeria welshimeri, Listeria grayi* (*L. grayi*, and *Listeria rocourtiae*, and so 24 strains in total were used (FIG. 3). These strains were obtained from National Bioresource Project (NBRP, Pathogenic Bacteria Department, Gifu University, Gifu city, Japan), American Type Culture Collection (ATCC, Rockville, Maryland, USA), Japan Collection of Microorganisms (JCM, RIKEN BioResource Center, Tsukuba City, Japan), National Institute of Technology and Evaluation, Biological Resource Center (NBRC, Kisarazu City, Japan). For the cultivation, a Brain Heart Infusion liquid medium (Nippon Becton Dickinson Company, Ltd., Tokyo, Japan) or an agar medium was used. In addition, the serotype of *Listeria monocytogenes* shown in FIG. 3 was determined by the multiplex polymerase chain reaction (PCR) method (see Non Patent Literature 15) using the *Listeria* type immunity serum "*Listeria* Antisera" (DENKA SEIKEN Co., Ltd., Tokyo, Japan).

(2) Analysis of DNA

The DNA sequence of the ribosomal protein encoded into the S10-spc-alpha operon and the ribosomal protein genes of biomarker candidates was sequenced by DNA sequencing with a primer designed based on the consensus sequence upstream and downstream of the target region of a genome sequencing strain. More specifically, the genomes were extracted from various strains of the genus *Listeria* shown in FIG. 3 by a conventional method, and the region of the ribosomal protein gene (up to 5 kbp) and the region of the biomarker proteins were amplified as a template thereof by the polymerase chain reaction (PCR) using KOD plus (Toyobo, Osaka, Japan) as high fidelity DNA polymerase. The obtained PCR product was purified and used as a template for DNA sequencing. DNA sequencing was performed using Big Dye ver. 3.1 Cycle Sequencing Kit (Applied Biosystems, Foster City, Calif.). The primers used for PCR and DNA sequencing are shown in FIG. 4.

Further, a mass-to-charge ratio of the ribosomal protein was calculated from the amino acid sequence obtained by translating the DNA base sequence of the ribosomal protein gene determined as described above and the mass of each amino acid shown in FIG. 5, and the mass-to-charge ratio was defined as the theoretical mass value.

(3) Measurement by MALDI-TOF MS

Bacterial cells were recovered from the Brain Heart Infusion liquid medium or agar medium, and about 3 colonies of bacterial cells were suspended in 0.5 mL of 70% ethanol. The suspension was centrifuged at 10,000 rpm for 2 minutes, and the obtained bacterial cell pellet was dried in a vacuum drier for 5 minutes to evaporate the ethanol. 10 μL of 35% formic acid was added to the dried pellet and stirred, which was obtained as an analysis sample. 1.5 μL of the analysis sample was added to 10 μL of a sinapinic acid matrix agent (solution containing 20 mg/mL sinapinic acid (Wako Pure Chemical Corporation, Osaka, Japan) in a solution of 50 v/v % acetonitrile and 1 v/v % trifluoroacetic acid) and sufficiently mixed. Then, 1.5 μL of the mixed solution was dropped on a sample plate and allowed to air dry. For the MALDI-TOF MS measurement, an AXIMA microorganism identification system (Shimadzu Corporation, Kyoto City, Japan) was used and the sample was measured in the positive linear mode and in the spectral range of 2000 m/z to 35000 m/z. The theoretical mass value calculated by the above method was matched with the measured mass-to-charge ratio with a tolerance of 500 ppm and appropriately corrected. For the calibration of the AXIMA microorganism identification system, the *Escherichia coli* DH5α strain was used.

(4) Construction of a Protein Mass Database for Discrimination of *Listeria monocytogenes*

With respect to the above 14 strains of *Listeria monocytogenes*, the theoretical mass value of the ribosomal protein described above was checked against the peak chart obtained by MALDI-TOF MS measurement and regarding the ribosomal proteins that could be actually detected, it was confirmed that there was no difference between the theoretical mass value and the actual measurement value. Next, the ribosomal proteins encoded into the S10-spc-alpha operon and other ribosomal proteins of the biomarker candidates were examined for the relationship between *Listeria monocytogenes* strain or serotype and the mass-to-charge ratio. The result is shown in FIG. 6. Because the acetyl group ($COCH_3$) was found to be modified in the ribosomal protein S9, the mass value of (S9+Ac) to which the acetyl group was added to the mass value calculated from the DNA sequence of the gene was defined as the theoretical mass value.

FIG. 6 shows the theoretical mass values (mass-to-charge ratios (m/z)) of ribosomal proteins encoded into the S10-spc-alpha operon and other ribosomal proteins of the biomarker candidates for 14 strains of *Listeria monocytogenes*. Serotypes 1/2b, 3b, 4b, 4d, and 4e are classified into Lineage I, serotypes 1/2a, 1/2c, 3a, and 3c are classified into Lineage II, and serotype 4a is classified into lineage III. In addition, ○, x, and Δ shown in FIG. 6 each indicate the results of peak processing under the default processing conditions (threshold offset: 0.015 mV, threshold response: 1.200) of the AXIMA microorganism identification system. That is, ○ indicates that the peak was detected within the tolerance of 500 ppm from the theoretical mass value, and x indicates that the peak was not detected in some cases. Also, Δ indicates that the peak was detected, but the difference from the theoretical mass value of other strains or other serotypes was small or the difference from the peak of other ribosomal proteins was within 500 ppm.

As can be seen from FIG. 6, the ribosomal proteins L3, L4, L23, L2, L24, L6, L18, S5, L15, S13, and S11 encoded into the S10-spc-alpha operon and the ribosomal proteins L10, L21, L13, and S9+Ac other than the operon, a total of 15, were found to have different theoretical mass values from other strains in some strains of *Listeria monocytogenes* used for the measurement. This suggested that these 15 ribosomal proteins are marker proteins that can be used to discriminate strains or serotypes of *Listeria monocytogenes*. The DNA base sequence in each strain of these 15 ribosomal proteins is shown in SEQ ID NO: 1 to 240 in the sequence listing. The outline of the sequence corresponding to each sequence number is as follows.

The DNA base sequences of 14 strains of *Listeria monocytogenes* (ATCC 15313T, JCM 2873, JCM 7671, JCM 7672, JCM 7673, JCM 7674, JCM 7675, JCM 7676, JCM 7677, JCM 7678, JCM 7680, JCM 7683, ATCC 51772, and ATCC 19115) and two strains of *Listeria seeligeri* (JCM 7679 and JCM 7682) are as follows.

SEQ ID NOs: 1 to 16: DNA base sequence of L3 in the above 16 strains.

SEQ ID NOs: 17 to 32: DNA base sequence of L4 in the above 16 strains.

SEQ ID NOs: 33 to 48: DNA base sequence of L23 in the above 16 strains.

SEQ ID NOs: 49 to 64: DNA base sequence of L2 in the above 16 strains.

SEQ ID NOs: 65 to 80: DNA base sequence of L24 in the above 16 strains.

SEQ ID NOs: 81 to 96: DNA sequence of L6 in the above 16 strains.

SEQ ID NOs: 97 to 112: DNA nucleotide sequence of L18 in the above 16 strains.

SEQ ID NOs: 113 to 128: the DNA nucleotide sequence of S5 in the above 16 strains.

SEQ ID NOs: 129 to 144: DNA base sequence of L15 in the above 16 strains.

SEQ ID NOs: 145 to 160: DNA base sequence of S13 in the above 16 strains.

SEQ ID NOs: 161 to 176: DNA base sequence of S11 in the above 16 strains.

SEQ ID NOs: 177 to 192: DNA base sequence of L10 in the above 16 strains.

SEQ ID NOs: 193 to 208: DNA base sequence of L21 in the above 16 strains.

SEQ ID NOs: 209 to 224: DNA nucleotide sequence of L13 in the above 16 strains.

SEQ ID NOs: 225 to 240: DNA sequence of S9 in the above 16 strains.

However, among the above 15 ribosomal proteins, L3, L4, L23, L2, L10, and L21 have one or more strains having a difference in theoretical mass value from other strains of 500 ppm or more and are considered as biomarker candidates to be used for discrimination of the strains, the peak shape was unclear or the peak intensity was insufficient and so it was not possible to detect the peak and therefore, these ribosomal proteins are considered to be inappropriate as stable biomarkers.

In addition, though ribosomal proteins S5 and L13 were able to detect peaks in MALDI-TOF MS measurement, the difference in theoretical mass value from other strains was 500 ppm or less, which makes the ribosomal proteins inappropriate as biomarkers. Further, S13 (m/z 13578.69 or 13552.65) overlaps with the peak of another ribosomal protein L20 (m/z 13552.08) and both peaks cannot be distinguished so S13 is still inappropriate as a biomarker.

On the other hand, 6 ribosomal proteins, L24, L6, L18, L15, S11, and S9+Ac, were detected in a stable manner regardless of the strain and the difference in theoretical mass value from other strains was 500 ppm or more and so were considered to be useful as biomarkers. Therefore, in the present embodiment, these 6 ribosomal proteins were used as biomarkers for discriminating the serotype or strain (or lineage) of *Listeria monocytogenes* in MALDI-TOF MS measurement.

(5) Construction of a Mass Database for Discrimination of the Genus *Listeria*

The 6 biomarkers L24, L6, L18, L15, S11, and S9+Ac, which have been shown to be useful for discriminating serotypes or strains of *Listeria monocytogenes*, were detected in a stable manner in all the strains of *Listeria monocytogenes* in MALDI-TOF MS measurement and thus, it was expected that the peaks of these proteins are likely to be detected in a stable manner in the same way even for samples of different species of the genus *Listeria*.

Thus, with respect to 10 strains of 6 species of *Listeria grayi, Listeria innocua, Listeria ivanovii, Listeria rocourtiae, Listeria seeligeri*, and *Listeria welshimeri* that were available from public distributors of the genus *Listeria*, the theoretical mass values of the 6 marker proteins were calculated by the method described above. As a result of MALDI-TOF MS measurement on these 10 strains, the peaks of the above 6 proteins were detected in a stable manner. In addition to the above 6 biomarkers, it was found that the ribosomal proteins L31 type B and S16 detected as distinct mass peaks showed characteristic peak masses depending on the species of the genus *Listeria*. Therefore, these two ribosomal proteins are also considered to be biomarkers that can be used to discriminate species of the genus *Listeria*, and a table of theoretical mass values for discrimination of species of the genus *Listeria* with respect to 8 ribosomal proteins newly including L31 type B (m/z 9259.36, 9290.34, 9327.44, or 9271.3) and S16 (m/z 10234.94, 10252.97, 10230.88, or 10003.54), in addition to the above 6 ribosomal proteins (L24, L6, L18, L15, S11, and S9), was created (FIG. 8). It is a matter of course that these 8 ribosomal proteins are biomarkers that can be used not only for discriminating species of the genus *Listeria*, but also for discriminating the serotype of *Listeria monocytogenes*.

The 56th amino acid of the ribosomal protein S11 of *Listeria grayi* has been specifically changed to lysine and further, in the result of MALDI-TOF MS measurement, the mass peak was observed at the position where the mass of the methyl group ($CH_3$) was added. From the above, the theoretical mass value was calculated assuming that S11 of *Listeria grayi* was methylated. Also, since S11 of *Listeria rocourtiae* (*L. rocourtiae* was observed to have a peak at a position larger than the theoretical mass value by about 17 in m/z, 17 was added to the theoretical mass value. Further, with respect to S16, theoretical values were calculated from the sequence information of genome-sequenced strains, and it was confirmed that the theoretical values are not different from the measured values of the strains actually measured this time. In addition, two patterns of DNA sequences were registered in S16 of *Listeria monocytogenes*, but the amino acid sequences matched.

The DNA base sequences of the above 8 ribosomal proteins determined in the above manner in 8 strains of 6 species are shown in SEQ ID NOs: 241 to 304 in the sequence listing. The outline of the sequence corresponding to each sequence number is as follows.

SEQ ID NOs: 241 to 248: DNA bae sequence of L24, L6, L18, L15, S11, S9+Ac, L31 type B, and S16 in the strain ATCC 33090T of *Listeria innocua*. The strain ATCC 33090T is the type strain (standard strain) of *Listeria innocua*.

SEQ ID NOs: 249 to 256: DNA base sequence of L24, L6, L18, L15, S11, S9+Ac, L31 type B, and S16 in the strain GTC02960 of *Listeria innocua.*

SEQ ID NOs: 257 to 264: DNA base sequence of L24, L6, L18, L15, S11, S9+Ac, L31 type B, and S16 in the strain JCM7681 of *Listeria ivanovii ivanovii.*

SEQ ID NOs: 265 to 272: DNA base sequence of L24, L6, L18, L15, S11, S9+Ac, L31 type B, and S16 in the strain ATCC44954 of *Listeria ivanovii londiniensis.*

SEQ ID NOs: 273 to 280: DNA base sequence of L24, L6, L18, L15, S11, S9+Ac, L31 type B, and S16 in the strain ATCC35967T of *Listeria seeligeri.*

SEQ ID NOs: 281 to 288: DNA base sequence of L24, L6, L18, L15, S11, S9+Ac, L31 type B, and S16 in the strain GTC02963 of *Listeria welshimeri.*

SEQ ID NOs: 289 to 296: DNA base sequence of L24, L6, L18, L15, S11, S9+Ac, L31 type B, and S16 in the strain GTC16429T of *Listeria rocourtiae.*

SEQ ID NOs: 297 to 304: DNA base sequence of L24, L6, L18, L15, S11, S9+Ac, L31 type B, and S16 in the strain ATCC19120T of *Listeria grayi.*

(6) Identification of Bacterial Species of the Genus *Listeria*

The mass pattern of the protein was analyzed by the fingerprint method using SARAMIS (trademark, Spectral Archive and Microbial Identification System), and it was confirmed that all the strains were bacteria of the genus *Listeria*. Subsequently, profile data was created by evaluating those having the mass-to-charge ratio of the peak on the mass spectrum of each strain matching the mass-to-charge ratio of a biomarker protein without mutation as "1", those that did not match as "2" to "5" (2 to 5 indicate mutually different mass-to-charge ratios), and those in which no peak corresponding to the biomarker protein was present as "0". This data was imported into PAST software (Natural History Museum, University of Oslo, Norway) and cluster-analyzed by the proximity coupling method using the Kimura algorithm. In addition, a phylogenetic tree (FIG. 13A) was created using FigTree ver. 1.4.0 software. As a result, as is clear from FIG. 13A, 7 bacterial species of the genus *Listeria* were correctly classified and further, *Listeria monocytogenes* was correctly classified for each lineage.

(7) Identification of the Strain or Serotype/Lineage of *Listeria monocytogenes*

By associating the mass-to-charge ratio of a peak obtained by MALDI-TOF MS measurement with the theoretical mass values of the above 6 ribosomal proteins, the attribution of the type of protein from which the peak was derived was analyzed to identify the strain of *Listeria monocytogenes*. For the analysis of attribution of protein types, software for discriminating bacteria was developed and used based on S10-GERMS (S10-spc-alpha operon Gene Encoded Ribosomal protein Mass Spectrum) method (see Patent Literature 3).

First, the above software was activated to register the theoretical mass value for each strain of the 6 ribosomal proteins L24, L6, L18, L15, S11, and S9+Ac (the value of the mass-to-charge ratio of the ribosomal protein L24 (m/z 11180.22, 11194.25, 11254.35), the value of the mass-to-charge ratio of the ribosomal protein L6 (m/z 19270.08 (19270.80), 19256.01), the value of the mass-to-charge ratio of the ribosomal protein L18 (m/z 13096.86, 13110.89), the value of the mass-to-charge ratio of the ribosomal protein L15 (m/z 15782.02, 15797.08), the value of the mass-to-charge ratio of the ribosomal protein S11 (m/z 13655.65, 13674.66), and the value of the mass-to-charge ratio of the ribosomal protein S9+Ac (m/z 14283.40, 14359.50, 14302.45)). Two theoretical mass values m/z 19270.08 and 19270.04 of L6 having a mass difference of 500 ppm or less were deemed not to be distinguishable from each other and so were registered as m/z 19270.08.

Next, mass spectrum data obtained by MALDI-TOF MS measurement was analyzed for each strain to examine whether or not the peak corresponding to a biomarker was correctly attributed to the theoretical mass value of the registered biomarker. As a result, as shown in FIG. 7A, for all strains, peaks corresponding to all biomarkers were attributed to the theoretical mass values of the registered biomarkers. FIG. 7B shows the relationship between the mass-to-charge ratios of the 6 ribosomal proteins and the attribution numbers 1 to 3 shown in FIG. 7A. Attribution patterns were classified into groups A to D and checked against the serotypes of each strain and it turned out that strains of lineage II belong to group A, strains of lineage I belong to groups B, C, and strains of lineage III belong to group D.

From the above, it is verified that L24 (m/z 11180.22, 11194.25, 11254.35), L6 (m/z 19270.08, 19256.01), L18 (m/z 13096.86, 13110.89), L15 (m/z 15782.02, 15797.08, 15668.86), S11 (m/z 13655.65, 13674.66) and S9+Ac (m/z 14283.40, 14359.50, or 14302.45) are useful marker proteins for discrimination of the serotype and lineage of *Listeria monocytogenes* in MALDI-TOF MS measurement. In addition, accurate masses of these marker proteins were calculated from these genetic information and these marker proteins were also checked against actual measurement values and therefore, it became clear that a mass database with high reliability can be constructed.

Figure 9A:
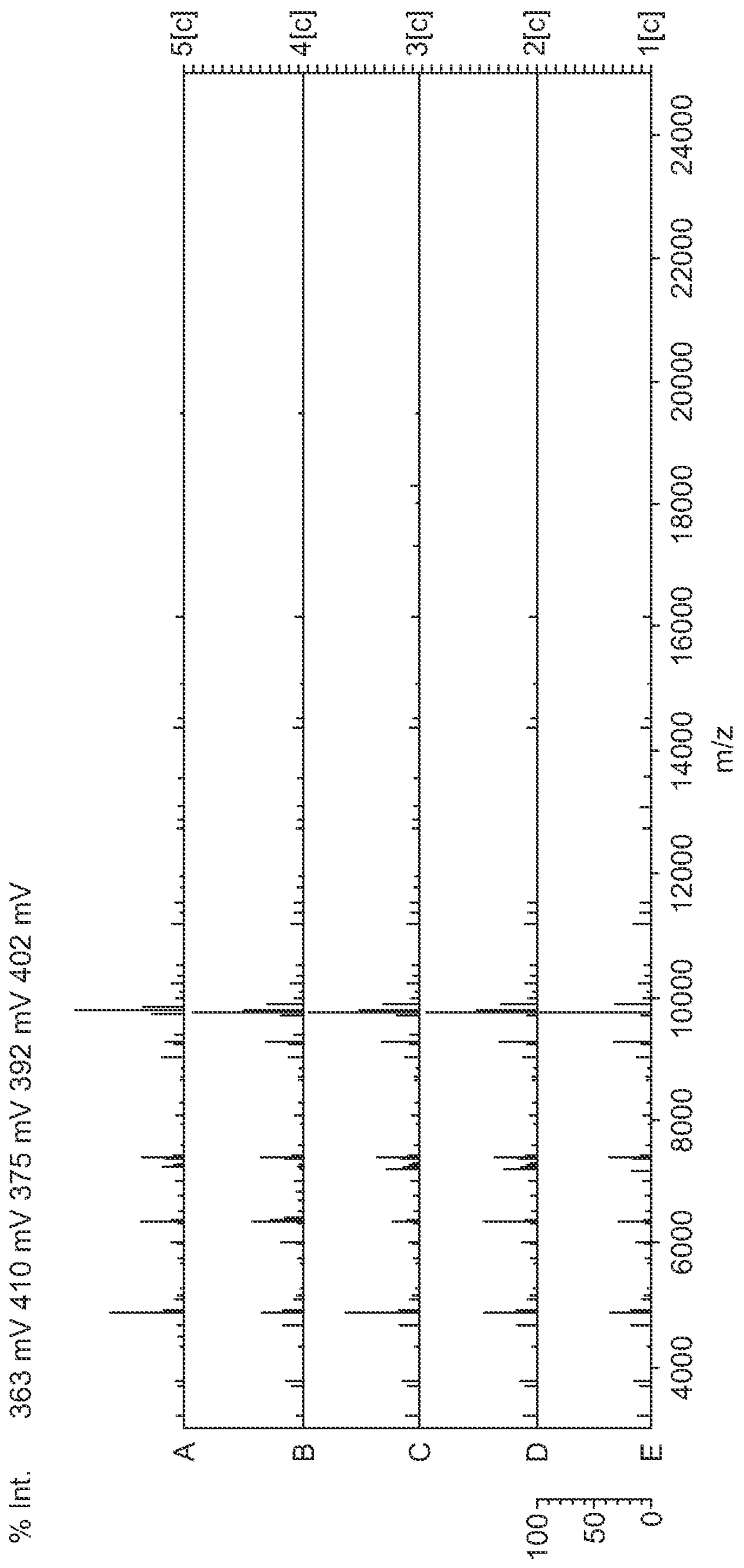
FIG. 9A is a chart obtained by MALDI-TOF MS measurement (part 1).
Figure 9B:
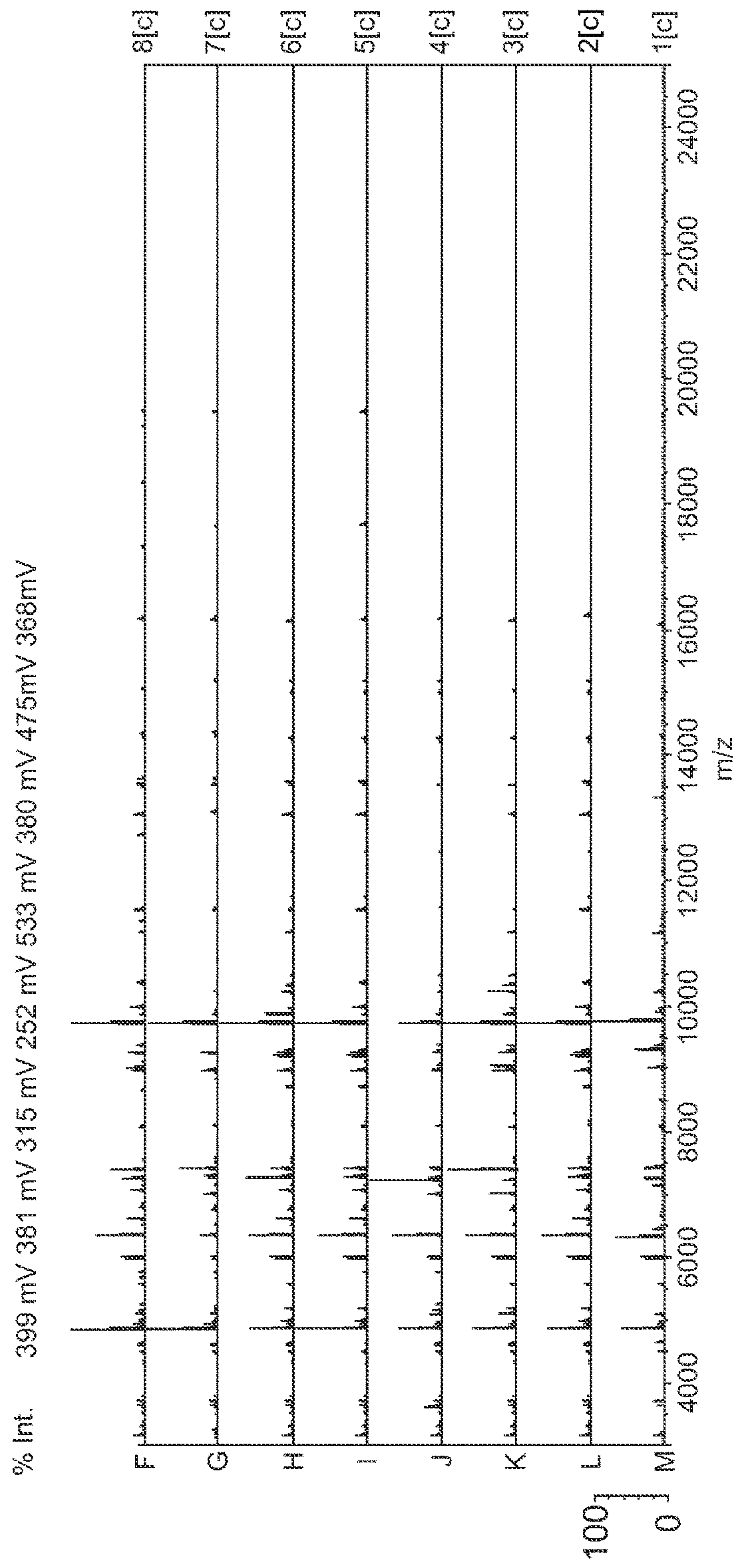
FIG. 9B is a chart obtained by MALDI-TOF MS measurement (part 2).
Figures 1, 11A:
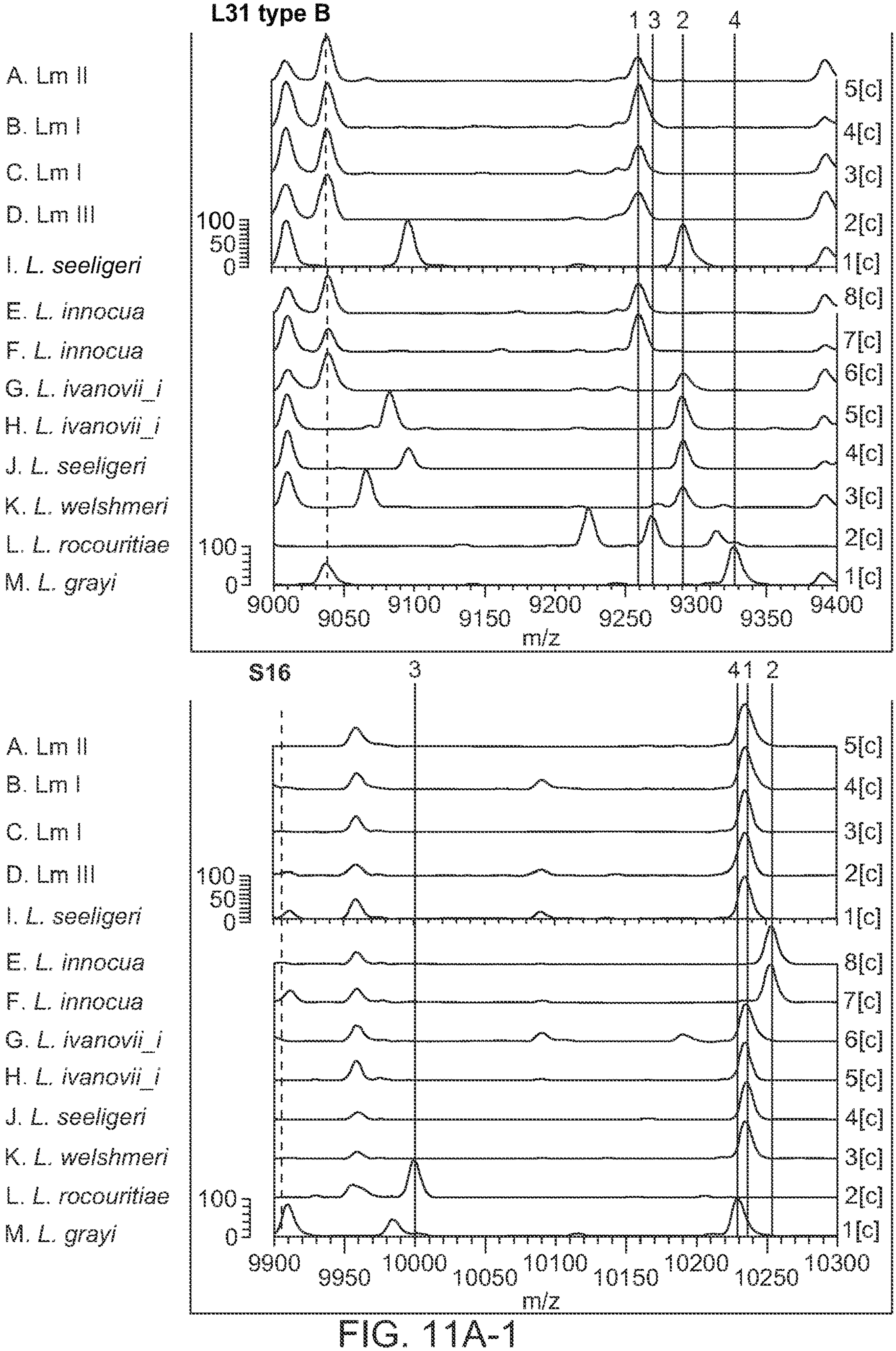
Figures 2, 11A:
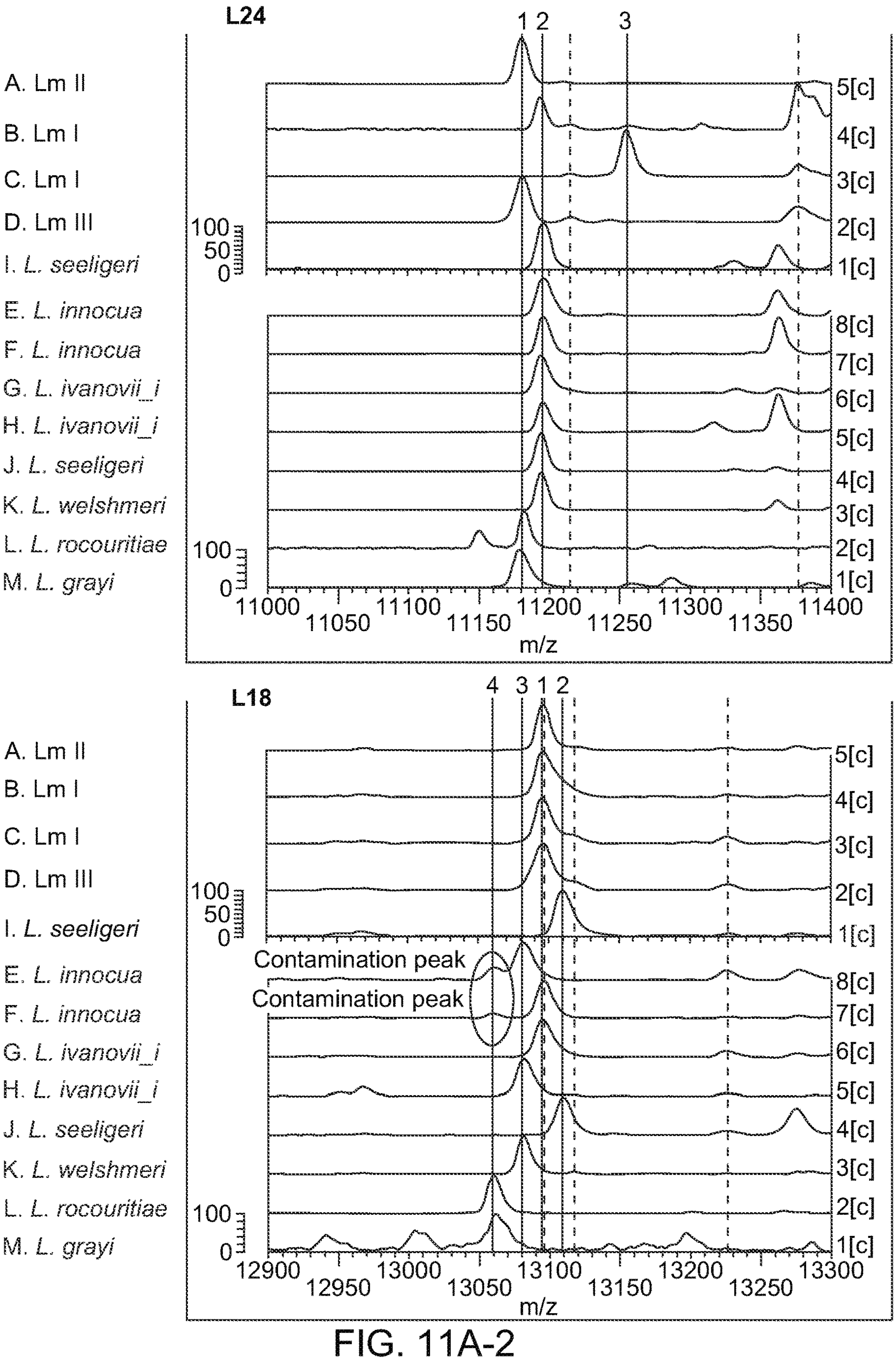
Figure 11B:
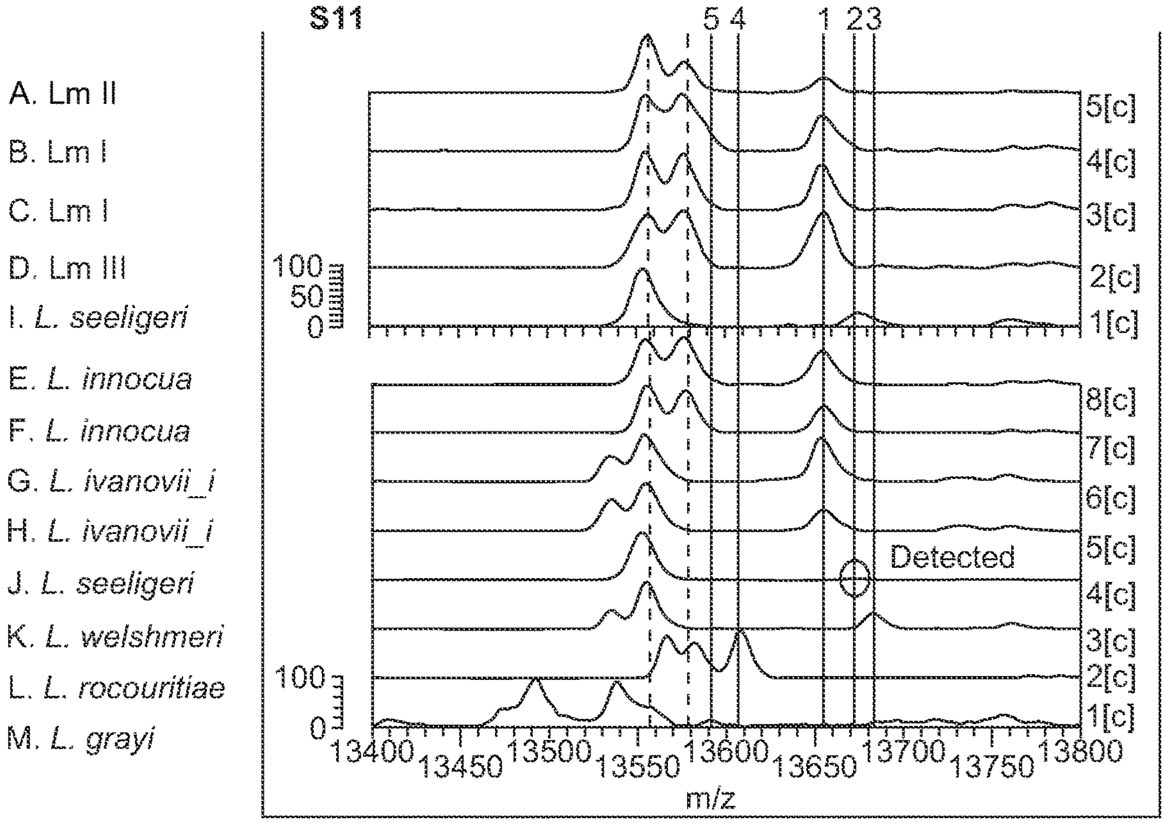
Figure 1:
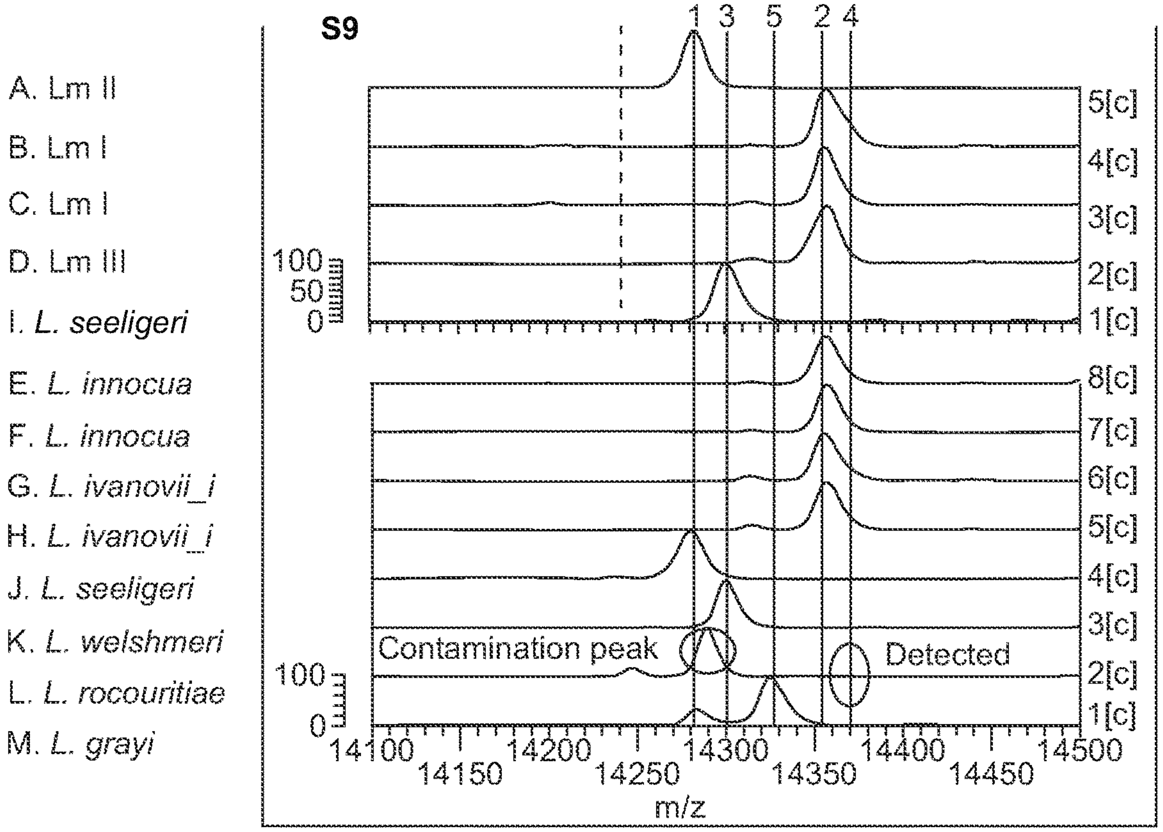
Figures 2, 11B:
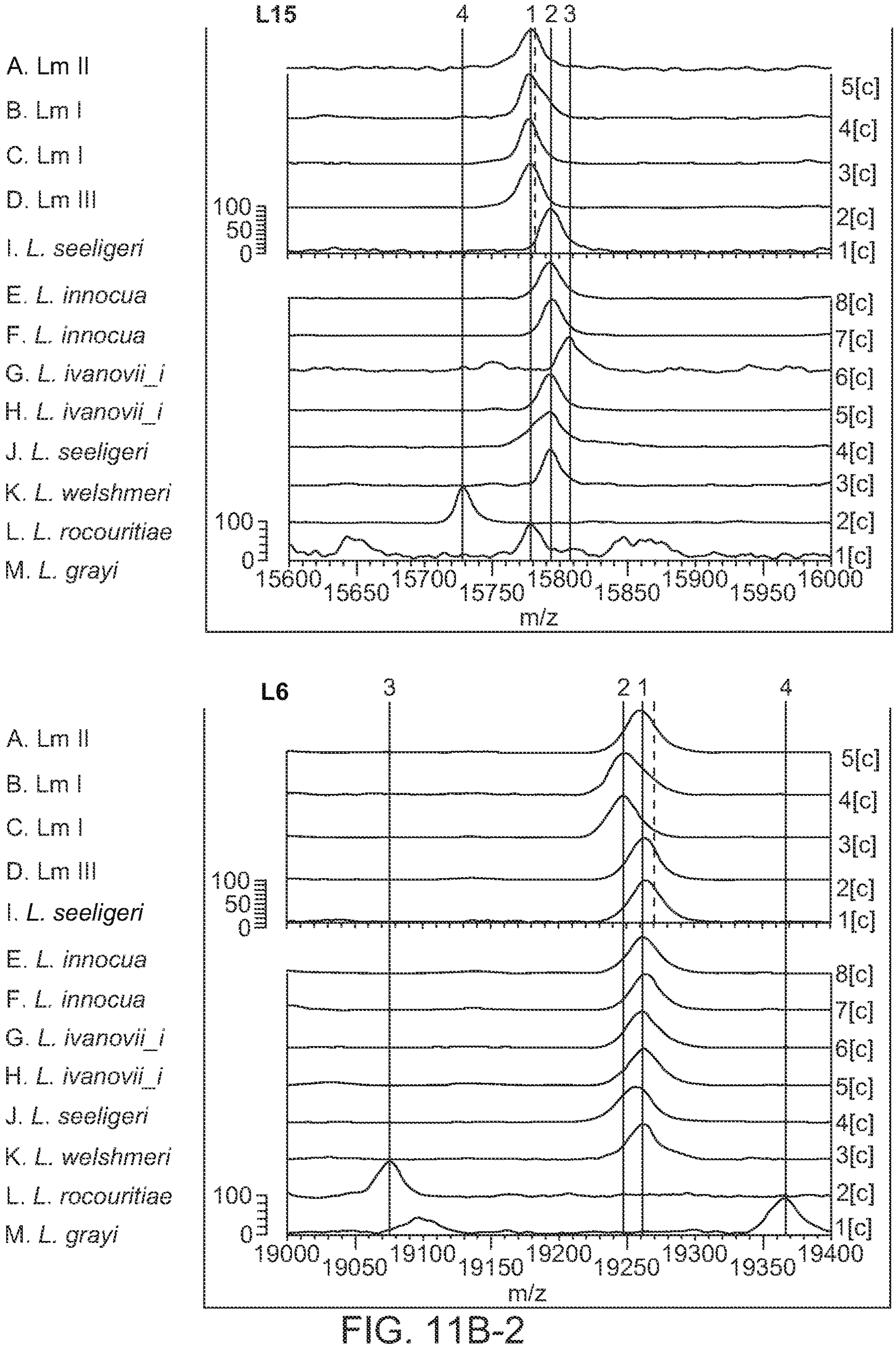

(8) Comparison of Discrimination Results Using SARAMIS and Discrimination Results by Cluster Analysis The species of the genus *Listeria* was discriminated using SARAMIS and the species of the genus *Listeria* was discriminated by cluster analysis using the theoretical mass values of 8 ribosomal proteins shown in FIG. 8 as an index and the results were compared. FIGS. 9A and 9B show charts obtained by MALDI-TOF MS measurements. FIG. 9A is a chart of bacterial species or strains of groups A to E, and FIG. 9B is a chart of bacterial species or strains of groups F to M. When these charts were analyzed using SARAMIS, the discrimination result shown in FIG. 10 was obtained. As can be seen from FIG. 10, two strains of *Listeria innocua*, one strain of *Listeria ivanovii, Listeria seeligeri* ATCC 35967, and *Listeria welshimeri* were all discriminated as "*Listeria* sp." and their species could not be identified. The *Listeria ivanovii* JCM7681 strain and *Listeria seeligeri* JCM7679 and JCM7682 strains were misidentified as *L. monocytogenes*. For *Listeria seeligeri* JCM7679 and JCM7682 strains, a biochemical test and sequence analysis of 16S RNA were carried out so that *Listeria seeligeri* could be identified. *Listeria rocourtiae* was not identified as a species because the theoretical mass value corresponding to its mass peak was not stored in the database of SARAMIS. On the other hand, *Listeria grayi* was correctly identified up to the species level by SARAMIS. Because *Listeria grayi* is systematically distant from other *Listeria* bacteria, *Listeria grayi* is considered to have been identifiable by the existing fingerprint method.

Next, based on the database of theoretical mass values shown in FIG. 8, attempts were made to discriminate the species of the genus *Listeria*. For m/z 15797.08, 15797.03, and 15796.09 of L15 with a small difference in mass value, these mass-to-charge ratios are considered to be not discriminable by actual measurements and so were all attributed by regarding as having the theoretical mass value m/z 15797.08. FIGS. 11A-1, 11A-2, 11B-1 and 11B-2 are enlarged views of the biomarker peak portions of the charts of FIGS. 9A and 9B. As can be seen from FIGS. 11A-1, 11A-2, 11B-1 and 11B-2, the biomarker mass was shifted by the species of the genus *Listeria* and peaks could be distinguished.

When the actual measurement values of 8 ribosomal proteins were compared with the theoretical values and attributed, the results shown in FIG. 12A were obtained. FIG. 12B is a table showing the correspondence relationship between the attribution number of the biomarker and the theoretical mass value in FIG. 12A. Incidentally, the numerals 1 to 5 shown on the charts in FIGS. 11A-1, 11A-2, 11B-1 and 11B-2 represent the attribution number of each biomarker.

As can be seen from FIGS. 8 and 12A, for *Listeria rocourtiae* and *Listeria grayi*, a difference between the theoretical value and the actual measurement value was found in some ribosomal proteins, but for other bacterial species of the genus *Listeria*, a difference in mass value of the ribosomal proteins could be discriminated.

Figure 13A:
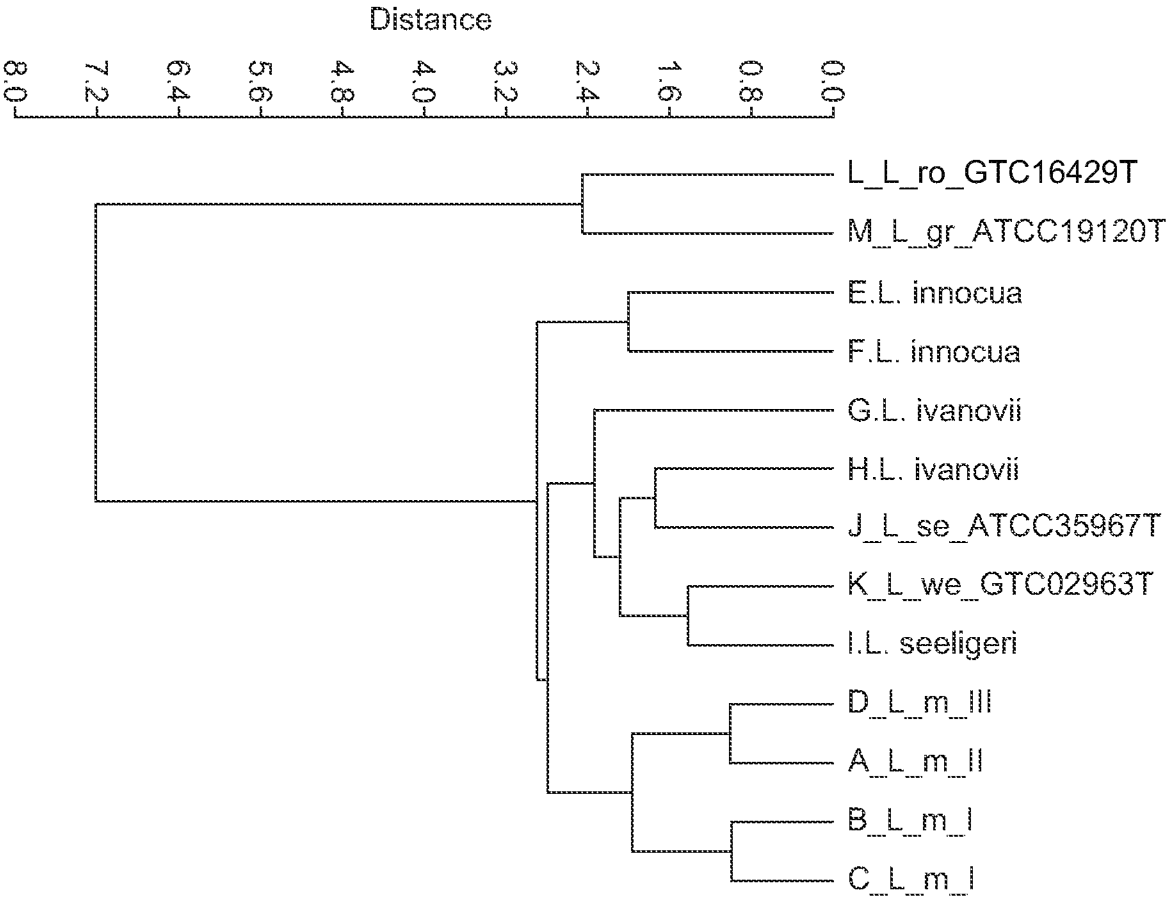
FIG. 13A is a dendrogram created using 8 ribosomal proteins.
Figure 13B:
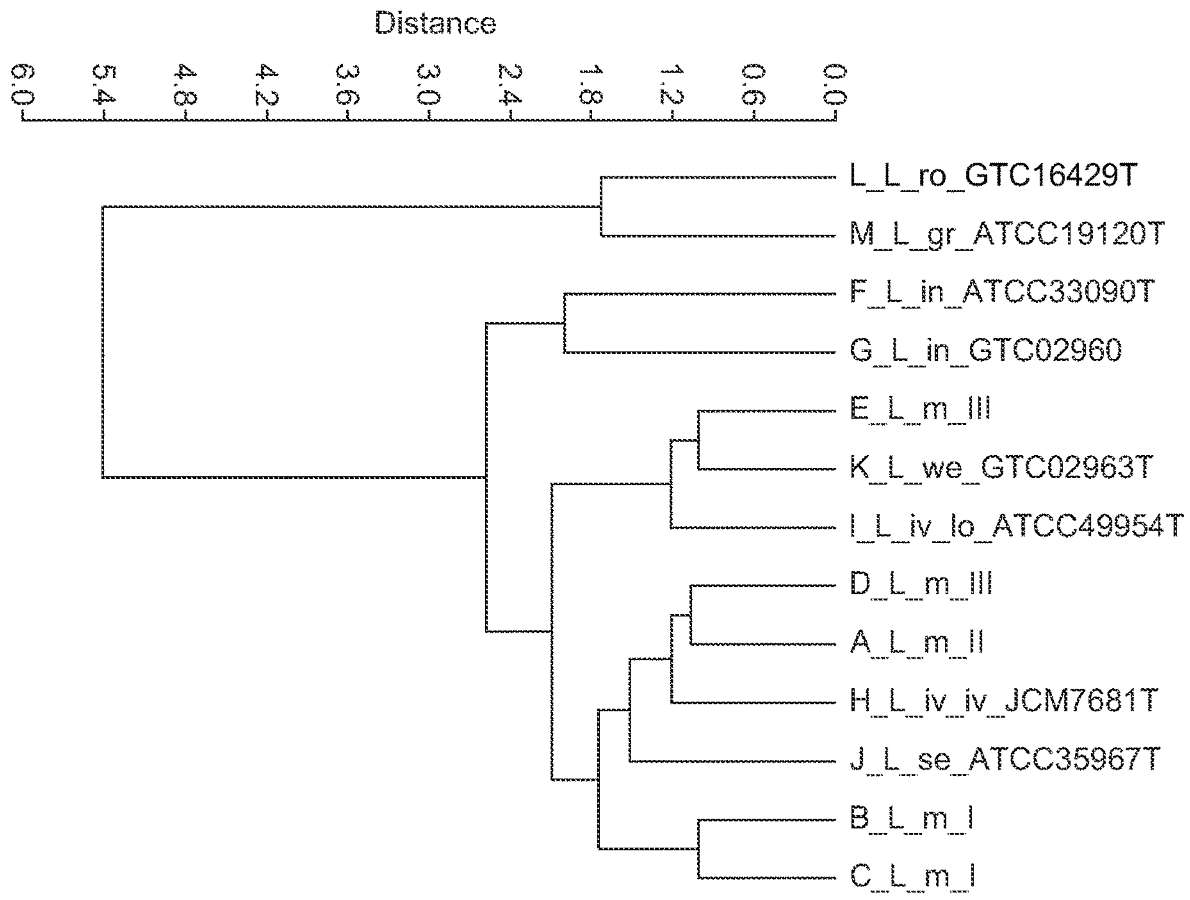
FIG. 13B is a dendrogram created using 5 ribosomal proteins.

A dendrogram (lineage diagram) showing the attribution result using the 8 ribosomal proteins shown in FIG. 12A and a dendrogram of the attribution result using five ribosomal proteins L24, S9, L6, L18, and S16 out of the 8 ribosomal proteins are shown in FIGS. 13A and 13B. In both cases, it is clear that the species of the genus *Listeria* can be discriminated and the lineage of *Listeria monocytogenes* can be discriminated. From the above, it was found that the discrimination method of the genus *Listeria* using the ribosomal proteins found in the present embodiment as marker proteins is a very effective method.

In the above embodiment, the second database 36 was caused to store the mass-to-charge ratios of 8 ribosomal proteins as marker proteins to discriminate which of the 7 bacterial species of the genus *Listeria* the test microorganism belongs to, but in the above embodiment, the second database 36 may also be caused to store the total of 17 ribosomal proteins, 15 ribosomal proteins (L3, L4, L23, L2, L24, L6, L18, S5, L15, S13, S11, L10, L21, L13, and S9) found in the process of constructing a protein mass database to discriminate *Listeria monocytogenes* and two ribosomal proteins (L31 (L31 type B), and S16) found in the process of constructing a protein mass database to discriminate the bacterial species other than *Listeria monocytogenes*, so that the subclass determination program 35 uses at least one of 17 ribosomal proteins to discriminate which of the bacterial species of the genus *Listeria* the test microorganism belongs to.

Further, in the above embodiment, the lineage of *Listeria monocytogenes* is discriminated by cluster analysis, but the lineage may also be discriminated by comparing the actual measurement value of one or more ribosomal proteins with the theoretical mass value. For example, the lineage may be discriminated from actual measurement values of mass peaks corresponding to the ribosomal proteins L24, L6, and S9. In particular, the ribosomal proteins L24 and L6 are useful as marker proteins to distinguish between a lineage I and other lineages, because a unique mass shift was observed in the lineage I of *Listeria monocytogenes.*

Further, distinct peaks could be detected in MALDI-TOF MS measurements of the ribosomal protein L18 and a unique mass shift was observed in *Listeria seeligeri*. Therefore, the ribosomal protein L18 may be used as a marker protein to discriminate *Listeria seeligeri.*

Also, the ribosomal protein S16 having a mass-to-charge ratio characteristic of *L. innocua* and the ribosomal protein S9 capable of discriminating a strain of *Listeria seeligeri* are useful as biomarkers to discriminate species of the genus *Listeria*. In addition, the ribosomal proteins L18, L15 become useful marker proteins to discriminate subspecies of *Listeria ivanovii*, and the ribosomal protein S11 becomes a useful marker protein to discriminate *Listeria welshimeri.*

REFERENCE SIGNS LIST

10 . . . Mass spectrometry unit
11 . . . Ionization unit
12 . . . TOF
13 . . . Extraction electrode
14 . . . Detector
20 . . . Microorganism determination unit
21 . . . CPU
22 . . . Memory
23 . . . Display unit
24 . . . Input unit
25 . . . I/F
30 . . . Storage unit
31 . . . OS
32 . . . Spectrum creation program
33 . . . Genus/species determination program
34 . . . First database
35 . . . Subclass determination program
36 . . . Second database
37 . . . Spectrum acquisition unit
38 . . . m/z reading unit
39 . . . Subclass determination unit
40 . . . Cluster analysis unit
41 . . . Dendrogram creation unit

The invention claimed is:

1. A method for discriminating a microorganism, the method comprising:

a) a step of subjecting a sample containing a microorganism to mass spectrometry to obtain a mass spectrum;

b) a reading step of reading a mass-to-charge ratio m/z of a peak derived from a marker protein from the mass spectrum; and c) a discrimination step of discriminating which bacterial species of *Listeria* bacteria is contained in the sample based on the mass-to-charge ratio m/z, wherein (i) at least one of ribosomal proteins L24, L6, L18, L15, S11, S9, and S16, and (ii) L31 are used as the marker protein; and a bacterial species of the *Listeria* bacteria is one of *Listeria innocua, Listeria welshimeri, Listeria seeligeri, Listeria ivanovii, Listeria grayi*, and *Listeria rocourtiae.*

2. A non-transitory computer-readable medium storing a program for causing a computer to execute each step according to claim 1.

* * * * *

SEQUENCE LISTING

```
Sequence total quantity: 341
SEQ ID NO: 1           moltype = DNA  length = 630
FEATURE                Location/Qualifiers
source                 1..630
                       mol_type = genomic DNA
                       organism = Listeria monocytogenes
SEQUENCE: 1
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagat  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tcgaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 2           moltype = DNA  length = 630
FEATURE                Location/Qualifiers
source                 1..630
                       mol_type = genomic DNA
                       organism = Listeria monocytogenes
SEQUENCE: 2
atgaccaaag gaatcttagg tagaaaagta gggatgacac aagttttcac tgaaaacggc  60
gaacttattc cagtaacagt aatcgaagca gcacaaaacg tggtacttca aaagaagact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 3           moltype = DNA  length = 630
FEATURE                Location/Qualifiers
source                 1..630
                       mol_type = genomic DNA
                       organism = Listeria monocytogenes
```

-continued

```
SEQUENCE: 3
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagat  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tcgaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 4            moltype = DNA  length = 630
FEATURE                 Location/Qualifiers
source                  1..630
                        mol_type = genomic DNA
                        organism = Listeria monocytogenes
SEQUENCE: 4
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tcgaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 5            moltype = DNA  length = 630
FEATURE                 Location/Qualifiers
source                  1..630
                        mol_type = genomic DNA
                        organism = Listeria monocytogenes
SEQUENCE: 5
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagat  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tcgaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 6            moltype = DNA  length = 630
FEATURE                 Location/Qualifiers
source                  1..630
                        mol_type = genomic DNA
                        organism = Listeria monocytogenes
SEQUENCE: 6
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccatggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 7            moltype = DNA  length = 630
FEATURE                 Location/Qualifiers
source                  1..630
                        mol_type = genomic DNA
                        organism = Listeria monocytogenes
SEQUENCE: 7
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
```

-continued

```
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 8            moltype = DNA  length = 630
FEATURE                 Location/Qualifiers
source                  1..630
                        mol_type = genomic DNA
                        organism = Listeria monocytogenes
SEQUENCE: 8
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 9            moltype = DNA  length = 630
FEATURE                 Location/Qualifiers
source                  1..630
                        mol_type = genomic DNA
                        organism = Listeria monocytogenes
SEQUENCE: 9
atgaccaaag gaatcttagg tagaaaagta gggatgacac aagttttcac tgaaaacggc  60
gaacttattc cagtaacagt aatcgaagca gcacaaaacg tggtacttca aaagaagact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gggcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 10           moltype = DNA  length = 630
FEATURE                 Location/Qualifiers
source                  1..630
                        mol_type = genomic DNA
                        organism = Listeria monocytogenes
SEQUENCE: 10
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tcgaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 11           moltype = DNA  length = 630
FEATURE                 Location/Qualifiers
source                  1..630
                        mol_type = genomic DNA
                        organism = Listeria monocytogenes
SEQUENCE: 11
atgaccaaag gaatcttagg tagaaaagta gggatgacac aagttttcac tgaaaacggc  60
gaacttattc cagtaacagt tatcgaagcg gcacaaaacg tggtacttca aaagaaaact  120
gttgaaactg acggctacga agctgtacaa atcggtttcg aagataagag agcaaaattg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630
```

```
SEQ ID NO: 12          moltype = DNA  length = 630
FEATURE                Location/Qualifiers
source                 1..630
                       mol_type = genomic DNA
                       organism = Listeria monocytogenes
SEQUENCE: 12
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 13          moltype = DNA  length = 630
FEATURE                Location/Qualifiers
source                 1..630
                       mol_type = genomic DNA
                       organism = Listeria monocytogenes
SEQUENCE: 13
atgaccaaag gaatcttagg tagaaaagta gggatgacac aagttttcac tgaaaacggc  60
gaacttattc cagtaacagt tatcgaagcg gcacaaaacg tggtacttca aaagaaaact  120
gttgaaactg acggctacga agctgtacaa atcggtttcg aagataagag agcaaaattg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtcaaaggt aacgttccag gcgctaaaaa agcattagtt  600
caaattaaaa ctgctactaa agcaaaataa                                  630

SEQ ID NO: 14          moltype = DNA  length = 630
FEATURE                Location/Qualifiers
source                 1..630
                       mol_type = genomic DNA
                       organism = Listeria monocytogenes
SEQUENCE: 14
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 15          moltype = DNA  length = 630
FEATURE                Location/Qualifiers
source                 1..630
                       mol_type = genomic DNA
                       organism = Listeria monocytogenes
SEQUENCE: 15
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tcgaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 16          moltype = DNA  length = 630
FEATURE                Location/Qualifiers
source                 1..630
                       mol_type = genomic DNA
                       organism = Listeria monocytogenes
```

-continued

```
SEQUENCE: 16
atgaccaaag gaatcttagg tagaaaagta gggatgacac aagttttcac tgaaaacggc  60
gaacttattc cagtaacagt aatcgaagca gcacaaaacg tggtacttca aaagaaaact  120
gttgaaactg acggctatga agctgtacaa atcggtttcg aagataagag agcaattttg  180
tcaaacaaac ccgaacaagg tcatgtagca aaagccaata ctactcctaa gcgcttcatt  240
cgcgaattcc gcgatgtaaa cttagacgag tatgagattg gtgcagaagt aaaagtagac  300
gtattcgcag aaggtgacat catcgacgcg acaggcgtat cgaaaggtaa aggattccaa  360
ggtgttatta aacgccacgg acaatcacgc ggccctatgg cccacggttc ccgttaccat  420
cgtcgcccag gttcaatggg tccagtagca cctaaccgtg ttttcaaaaa taaactactt  480
ccaggtcgta tgggtggaga acaaatcact atccaaaacc tagaaatcgt taaagtagac  540
gttgaaaaga acgttctttt agtaaaaggt aacgttccag gcgctaaaaa agcattagtt  600
caaattaaaa ctgctactaa agcaaaataa                                  630

SEQ ID NO: 17          moltype = DNA  length = 624
FEATURE                Location/Qualifiers
source                 1..624
                       mol_type = genomic DNA
                       organism = Listeria monocytogenes
SEQUENCE: 17
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc ggctgaaagt  540
atctcagtac tagaagttgc taaacatgat aaattaatta tcactaaagc agctgtcgaa  600
aaagtagagg aggtgctcgc ataa                                        624

SEQ ID NO: 18          moltype = DNA  length = 624
FEATURE                Location/Qualifiers
source                 1..624
                       mol_type = genomic DNA
                       organism = Listeria monocytogenes
SEQUENCE: 18
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                        624

SEQ ID NO: 19          moltype = DNA  length = 624
FEATURE                Location/Qualifiers
source                 1..624
                       mol_type = genomic DNA
                       organism = Listeria monocytogenes
SEQUENCE: 19
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc ggctgaaagt  540
atctcagtac tagaagttgc taaacatgat aaattaatta tcactaaagc agctgtcgaa  600
aaagtagagg aggtgctcgc ataa                                        624

SEQ ID NO: 20          moltype = DNA  length = 624
FEATURE                Location/Qualifiers
source                 1..624
                       mol_type = genomic DNA
                       organism = Listeria monocytogenes
SEQUENCE: 20
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
```

-continued

```
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc ggctgaaagt  540
atctcagtac tagaagttgc taaacatgat aaattaatta tcactaaagc agctgtcgaa  600
aaagtagagg aggtgctcgc ataa                                          624

SEQ ID NO: 21          moltype = DNA  length = 624
FEATURE                Location/Qualifiers
source                 1..624
                       mol_type = genomic DNA
                       organism = Listeria monocytogenes
SEQUENCE: 21
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc ggctgaaagt  540
atctcagtac tagaagttgc taaacatgat aaattaatta tcactaaagc agctgtcgaa  600
aaagtagagg aggtgctcgc ataa                                          624

SEQ ID NO: 22          moltype = DNA  length = 624
FEATURE                Location/Qualifiers
source                 1..624
                       mol_type = genomic DNA
                       organism = Listeria monocytogenes
SEQUENCE: 22
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccacaatggc gcggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                          624

SEQ ID NO: 23          moltype = DNA  length = 624
FEATURE                Location/Qualifiers
source                 1..624
                       mol_type = genomic DNA
                       organism = Listeria monocytogenes
SEQUENCE: 23
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                          624

SEQ ID NO: 24          moltype = DNA  length = 624
FEATURE                Location/Qualifiers
source                 1..624
                       mol_type = genomic DNA
                       organism = Listeria monocytogenes
SEQUENCE: 24
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                          624

SEQ ID NO: 25          moltype = DNA  length = 624
```

-continued

```
FEATURE              Location/Qualifiers
source               1..624
                     mol_type = genomic DNA
                     organism = Listeria monocytogenes
SEQUENCE: 25
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                         624

SEQ ID NO: 26        moltype = DNA  length = 624
FEATURE              Location/Qualifiers
source               1..624
                     mol_type = genomic DNA
                     organism = Listeria monocytogenes
SEQUENCE: 26
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc ggctgaaagt  540
atctcagtac tagaagttgc taaacatgat aaattaatta tcactaaagc agctgtcgaa  600
aaagtagagg aggtgctcgc ataa                                         624

SEQ ID NO: 27        moltype = DNA  length = 624
FEATURE              Location/Qualifiers
source               1..624
                     mol_type = genomic DNA
                     organism = Listeria monocytogenes
SEQUENCE: 27
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc ttcgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccacaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttaact ttcgatgctc ctaaaacaaa agaatttgcg  420
gcttttctta aaaatatctc tgtagatact aaggcactaa tcgtagttgc tagtgaaagt  480
gaaaatgtag aattatctgc acgcaactta caaggcatta cagttattcc agctgaaagt  540
atctcagtac tagaagttgc taaacatgat aagttaatta tcactaaagc agctgtcgaa  600
aaagtagagg aggtgctcgc ataa                                         624

SEQ ID NO: 28        moltype = DNA  length = 624
FEATURE              Location/Qualifiers
source               1..624
                     mol_type = genomic DNA
                     organism = Listeria monocytogenes
SEQUENCE: 28
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                         624

SEQ ID NO: 29        moltype = DNA  length = 624
FEATURE              Location/Qualifiers
source               1..624
                     mol_type = genomic DNA
                     organism = Listeria monocytogenes
SEQUENCE: 29
atgccaaaat taagcttact taaacaagat ggaacaaacg ctggcgaaat tactttaaac  60
gacactgttt tcggtatcga accaaatgaa aaagttgttg ttgatgtgat tttgagccaa  120
```

-continued

```
cgtgcatccc ttcgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccacaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttaact ttcgatgctc ctaaaacaaa agaatttgcg  420
gcttttctta aaaatatctc tgtagatact aaggcactaa tcgtagttgc tagtgaaagt  480
gaaaatgtag aattatctgc acgcaactta caaggcatta cagttattcc agctgaaagt  540
atctcagtac tagaagttgc taaacatgat aagttaatta tcactaaagc agctgtcgaa  600
aaagtagagg aggtgctcgc ataa                                          624

SEQ ID NO: 30          moltype = DNA  length = 624
FEATURE                Location/Qualifiers
source                 1..624
                       mol_type = genomic DNA
                       organism = Listeria monocytogenes
SEQUENCE: 30
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                          624

SEQ ID NO: 31          moltype = DNA  length = 624
FEATURE                Location/Qualifiers
source                 1..624
                       mol_type = genomic DNA
                       organism = Listeria monocytogenes
SEQUENCE: 31
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcttacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc tggtgaaagt  480
gaaaatgtag aattatctgc acgcaactta caaggcatta cagttattcc ggctgaaagt  540
atctcagtac tagaagttgc taaacatgat aaattaatta tcactaaagc agctgtcgaa  600
aaagtagagg aggtgctcgc ataa                                          624

SEQ ID NO: 32          moltype = DNA  length = 624
FEATURE                Location/Qualifiers
source                 1..624
                       mol_type = genomic DNA
                       organism = Listeria monocytogenes
SEQUENCE: 32
atgccaaaat taagcttact taaacaagat ggaacaaacg ctggcgaaat tactttaaac  60
gacactgttt tcggtatcga accaaatgaa aaagttgttg ttgatgtgat tttgagccaa  120
cgtgcatccc tacgtcaagg gactcacaaa gtaaaaaatc gttcagaagt acgtggtggc  180
ggacgtaaac catggcgtca aaaaggtaca ggtcgtgccc gtcaaggttc aatccgttcc  240
ccgcaatggc gtggcggtgg tgtcgtattc ggcccaacac ctcgttcata tgcatacaaa  300
ttacctaaga aagttcgtcg tttagcgatt aaatcaattc tttcttctaa agtaaatgaa  360
gaaaaattag ttgtacttga aggtttgact ttcgatgcac ctaaaacaaa agaatttgcg  420
gcttttctta aaaatatctc tgtagatact aaggcactaa tcgtagttgc cggtgaaagt  480
gaaaatgtag aattatctgc acgcaactta caaggcatta cagttattcc agctgaaagt  540
atctcagtac tagaagttgc taaacatgat aaattaatta tcactaaagc agctgtcgaa  600
aaagtagagg aggtgctcgc ataa                                          624

SEQ ID NO: 33          moltype = DNA  length = 285
FEATURE                Location/Qualifiers
source                 1..285
                       mol_type = genomic DNA
                       organism = Listeria monocytogenes
SEQUENCE: 33
atggatgcac gcgacatcat taagcgccca gttgtaactg aagaatctac aagcattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                   285

SEQ ID NO: 34          moltype = DNA  length = 285
FEATURE                Location/Qualifiers
source                 1..285
```

-continued

```
                        mol_type = genomic DNA
                        organism = Listeria monocytogenes
SEQUENCE: 34
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 35           moltype = DNA  length = 285
FEATURE                 Location/Qualifiers
source                  1..285
                        mol_type = genomic DNA
                        organism = Listeria monocytogenes
SEQUENCE: 35
atggatgcac gcgacatcat taagcgccca gttgtaactg aagaatctac aagcattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 36           moltype = DNA  length = 285
FEATURE                 Location/Qualifiers
source                  1..285
                        mol_type = genomic DNA
                        organism = Listeria monocytogenes
SEQUENCE: 36
atggatgcac gcgacatcat taagcgccca gttgtaactg aagaatctac aagcattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 37           moltype = DNA  length = 285
FEATURE                 Location/Qualifiers
source                  1..285
                        mol_type = genomic DNA
                        organism = Listeria monocytogenes
SEQUENCE: 37
atggatgcac gcgacatcat taagcgccca gttgtaactg aagaatctac aagcattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 38           moltype = DNA  length = 285
FEATURE                 Location/Qualifiers
source                  1..285
                        mol_type = genomic DNA
                        organism = Listeria monocytogenes
SEQUENCE: 38
atggatgcac gcgacatcat taagcgccca gttgtaactg aagaatctac aagcattctc  60
gacgataaga aatatacatt tgaagtagat actcgcgcaa ctaaaacgca agtaaaatac  120
gcaattgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 39           moltype = DNA  length = 285
FEATURE                 Location/Qualifiers
source                  1..285
                        mol_type = genomic DNA
                        organism = Listeria monocytogenes
SEQUENCE: 39
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 40           moltype = DNA  length = 285
FEATURE                 Location/Qualifiers
source                  1..285
                        mol_type = genomic DNA
                        organism = Listeria monocytogenes
SEQUENCE: 40
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
```

-continued

```
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 41           moltype = DNA  length = 285
FEATURE                 Location/Qualifiers
source                  1..285
                        mol_type = genomic DNA
                        organism = Listeria monocytogenes
SEQUENCE: 41
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 42           moltype = DNA  length = 285
FEATURE                 Location/Qualifiers
source                  1..285
                        mol_type = genomic DNA
                        organism = Listeria monocytogenes
SEQUENCE: 42
atggatgcac gcgacatcat taagcgccca gttgtaactg aagaatctac aagcattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 43           moltype = DNA  length = 285
FEATURE                 Location/Qualifiers
source                  1..285
                        mol_type = genomic DNA
                        organism = Listeria monocytogenes
SEQUENCE: 43
atggatgcac gcgacatcat taagcgcccg gttgtaactg aagaatctac aagcattctc  60
gacgataaga aatatacttt tgaagtagat actcgcgcaa ctaaaacgca agtaaaatac  120
gcagttgaag aaatttttga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 44           moltype = DNA  length = 285
FEATURE                 Location/Qualifiers
source                  1..285
                        mol_type = genomic DNA
                        organism = Listeria monocytogenes
SEQUENCE: 44
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 45           moltype = DNA  length = 285
FEATURE                 Location/Qualifiers
source                  1..285
                        mol_type = genomic DNA
                        organism = Listeria monocytogenes
SEQUENCE: 45
atggatgcac gcgacatcat taagcgcccg gttgtaactg aagaatctac aagcattctc  60
gacgataaga aatatacttt tgaagtagat actcgcgcaa ctaaaacgca agtaaaatac  120
gcagttgaag aaatttttga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 46           moltype = DNA  length = 285
FEATURE                 Location/Qualifiers
source                  1..285
                        mol_type = genomic DNA
                        organism = Listeria monocytogenes
SEQUENCE: 46
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285
```

```
SEQ ID NO: 47          moltype = DNA  length = 285
FEATURE                Location/Qualifiers
source                 1..285
                       mol_type = genomic DNA
                       organism = Listeria monocytogenes
SEQUENCE: 47
atggatgcac gcgacatcat taagcgccca gttgtaactg aagaatctac aagcattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 48          moltype = DNA  length = 285
FEATURE                Location/Qualifiers
source                 1..285
                       mol_type = genomic DNA
                       organism = Listeria monocytogenes
SEQUENCE: 48
atggatgcac gcgacatcat taagcgccca gttgtaactg aagaatctac aagtattctc  60
gacgataaga aatatacatt tgaagtagat actcgcgcaa ctaaaacgca agtaaaatac  120
gcagttgaag aaattttcga cgtaaaagtt gctaaagtaa acgtaatgaa ttacaaaggc  180
aaacttaaac gtatgggccg ttatgcaggt tacactaaca aacgccgtaa agcgattgtt  240
actgttacag ctgacagcaa agaaattcaa ttctttgaag tataa                  285

SEQ ID NO: 49          moltype = DNA  length = 834
FEATURE                Location/Qualifiers
source                 1..834
                       mol_type = genomic DNA
                       organism = Listeria monocytogenes
SEQUENCE: 49
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc gaaaggcctt gaagtaggcc aaacaattta ttcaggagca  360
gaagctgaca tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 50          moltype = DNA  length = 834
FEATURE                Location/Qualifiers
source                 1..834
                       mol_type = genomic DNA
                       organism = Listeria monocytogenes
SEQUENCE: 50
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 51          moltype = DNA  length = 834
FEATURE                Location/Qualifiers
source                 1..834
                       mol_type = genomic DNA
                       organism = Listeria monocytogenes
SEQUENCE: 51
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc gaaaggcctt gaagtaggcc aaacaattta ttcaggagca  360
```

-continued

```
gaagctgaca tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 52          moltype = DNA  length = 834
FEATURE                Location/Qualifiers
source                 1..834
                       mol_type = genomic DNA
                       organism = Listeria monocytogenes
SEQUENCE: 52
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgaca ttaaagtcgg taatgcacta gaattaaaag atattccagt gggtactgtt  420
atccacaata tcgaaatgaa acctggtaaa ggtggacaat tagtacgttc tgctggaaca  480
agtgctcaag tacttggtaa agaaggcaaa tacgtattaa tccgcttaaa ctctggtgaa  540
gttcgcatga tccttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 53          moltype = DNA  length = 834
FEATURE                Location/Qualifiers
source                 1..834
                       mol_type = genomic DNA
                       organism = Listeria monocytogenes
SEQUENCE: 53
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc gaaaggcctt gaagtaggcc aaacaattta ttcaggagca  360
gaagctgaca tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 54          moltype = DNA  length = 834
FEATURE                Location/Qualifiers
source                 1..834
                       mol_type = genomic DNA
                       organism = Listeria monocytogenes
SEQUENCE: 54
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgaca tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tacttggtaa agaaggcaaa tacgtattaa tccgcttaaa ctctggtgaa  540
gttcgcatga tccttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 55          moltype = DNA  length = 834
FEATURE                Location/Qualifiers
source                 1..834
                       mol_type = genomic DNA
                       organism = Listeria monocytogenes
```

-continued

```
SEQUENCE: 55
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggcaaaccaa ctcttggata caaaacacgt  780
aagaaaaaca acaactccga taaatttatc gtacgtcgtc gtaagaaaaa ataa        834

SEQ ID NO: 56           moltype = DNA  length = 834
FEATURE                 Location/Qualifiers
source                  1..834
                        mol_type = genomic DNA
                        organism = Listeria monocytogenes
SEQUENCE: 56
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 57           moltype = DNA  length = 834
FEATURE                 Location/Qualifiers
source                  1..834
                        mol_type = genomic DNA
                        organism = Listeria monocytogenes
SEQUENCE: 57
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 58           moltype = DNA  length = 834
FEATURE                 Location/Qualifiers
source                  1..834
                        mol_type = genomic DNA
                        organism = Listeria monocytogenes
SEQUENCE: 58
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgaca ttaaagtcgg taatgcacta gaattaaaag atattccagt gggtactgtt  420
atccacaata tcgaaatgaa acctggtaaa ggtggacaat tagtacgttc tgctggaaca  480
agtgctcaag tacttggtaa agaaggcaaa tacgtattaa tccgcttaaa ctctggtgaa  540
gttcgcatga tccttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834
```

-continued

```
SEQ ID NO: 59          moltype = DNA  length = 834
FEATURE                Location/Qualifiers
source                 1..834
                       mol_type = genomic DNA
                       organism = Listeria monocytogenes
SEQUENCE: 59
atggcgatca aaaagtataa acctaccaca aacgggcgcc ggcatatgac tagttcagat  60
tttgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagccgaca tcaaaatcgg taatgcacta gaattaaaag atattccagt gggtactgtt  420
atccacaata tcgaaatgaa acctggtaaa ggtggacaat tagtacgttc agctggaaca  480
agtgctcaag tgcttggtaa agaaggtaaa tacgtattaa tccgcttaaa ctctggtgaa  540
gttcgcatga ttcttgctac ttgccgcgct acaatcggtc aagttggtaa cgaacaacac  600
gaacttatca acattggtaa agcaggtcgt tcacgttgga tgggtaaacg cccaactgtt  660
cgtggatctg taatgaaccc taacgatcac ccgcacggtg gtggtgaagg taaagctcca  720
atcggtcgta aatctccaat gtctccatgg ggtaaaccaa ctcttggata caaaacacgt  780
aagaaaaata acaactccga taaatttatc gtacgtcgtc gtaagaaaaa ataa        834

SEQ ID NO: 60          moltype = DNA  length = 834
FEATURE                Location/Qualifiers
source                 1..834
                       mol_type = genomic DNA
                       organism = Listeria monocytogenes
SEQUENCE: 60
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggcaaaccaa ctcttggata caaaacacgt  780
aagaaaaaca acaactccga taaatttatc gtacgtcgtc gtaagaaaaa ataa        834

SEQ ID NO: 61          moltype = DNA  length = 834
FEATURE                Location/Qualifiers
source                 1..834
                       mol_type = genomic DNA
                       organism = Listeria monocytogenes
SEQUENCE: 61
atggcgatca aaaagtataa acctaccaca aacgggcgcc ggcatatgac tagttcagat  60
tttgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagccgaca tcaaaatcgg taatgcacta gaattaaaag atattccagt gggtactgtt  420
atccacaata tcgaaatgaa acctggtaaa ggtggacaat tagtacgttc agctggaaca  480
agtgctcaag tgcttggtaa agaaggtaaa tacgtattaa tccgcttaaa ctctggtgaa  540
gttcgcatga ttcttgctac ttgccgcgct acaatcggtc aagttggtaa cgaacaacac  600
gaacttatca acattggtaa agcaggtcgt tcacgttgga tgggtaaacg cccaactgtt  660
cgtggatctg taatgaaccc taacgatcac ccgcacggtg gtggtgaagg taaagctcca  720
atcggtcgta aatctccaat gtctccatgg ggtaaaccaa ctcttggata caaaacacgt  780
aagaaaaata acaactccga taaatttatc gtacgtcgtc gtaagaaaaa ataa        834

SEQ ID NO: 62          moltype = DNA  length = 834
FEATURE                Location/Qualifiers
source                 1..834
                       mol_type = genomic DNA
                       organism = Listeria monocytogenes
SEQUENCE: 62
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
```

-continued

```
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 63          moltype = DNA  length = 834
FEATURE                Location/Qualifiers
source                 1..834
                       mol_type = genomic DNA
                       organism = Listeria monocytogenes
SEQUENCE: 63
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgaca ttaaagtcgg taatgcacta gaattaaaag atattccagt gggtactgtt  420
atccacaata tcgaaatgaa acctggtaaa ggtggacaat tagtacgttc tgctggaaca  480
agtgctcaag tacttggtaa agaaggcaaa tacgtattaa tccgcttaaa ctctggtgaa  540
gttcgcatga tccttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggtaaaccaa ctcttggata caaaacacgt  780
aagaaaaaca acaactccga taaatttatc gtacgtcgtc gtaagaaaaa ataa        834

SEQ ID NO: 64          moltype = DNA  length = 834
FEATURE                Location/Qualifiers
source                 1..834
                       mol_type = genomic DNA
                       organism = Listeria monocytogenes
SEQUENCE: 64
atggcgatca aaaagtataa acctaccact aacgggcgcc ggcacatgac tagttctgat  60
ttcgctgaga ttactacaag tactccagaa aaatctttac tacgtcctct taaaaagaaa  120
gccggacgca ataaccaagg taagttaact gttcgtcatc acggcggtgg ccataaacgc  180
caataccgcg tgattgattt caaacgtaac aaagatggta ttcctggacg cgttgcaacg  240
atcgagtacg atccaaaccg ttctgctaat attgctctaa tcaactatgc tgatggagaa  300
aaacgctaca tcatcgcagc aaaaggcctt gaagtaggtc aaacaattta ttcaggagca  360
gaagctgata tcaaagtcgg taatgcacta gaattaaaag atattccagt gggtactgtt  420
atccacaata tcgaaatgaa acctggtaaa ggtggacaat tagtacgttc tgctggaaca  480
agtgctcaag tgcttggtaa agaaggtaaa tacgtattaa tccgcttaaa ctctggtgaa  540
gttcgcatga ttcttgctac ttgccgtgct acaatcggtc aagttggtaa cgaacaacac  600
gaacttatca acatcggtaa agcaggtcgt tcacgttgga tgggtaaacg cccaactgtt  660
cgtggatctg taatgaaccc gaacgatcac ccacacggtg gtggtgaagg taaagctcca  720
atcggccgta aatcgccaat gtctccatgg ggcaaaccaa ctcttggata caaaacacgt  780
aagaaaaaca acaactccga taaatttatc gtacgtcgtc gtaagaaaaa ataa        834

SEQ ID NO: 65          moltype = DNA  length = 312
FEATURE                Location/Qualifiers
source                 1..312
                       mol_type = genomic DNA
                       organism = Listeria monocytogenes
SEQUENCE: 65
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta cttgacccta aaacaggcga acctactcgt  240
gtaggatacg aagttaaagg cgacaagaaa gtacgcgtag caaaaaaatc cggtgaagta  300
atagataaat aa                                                      312

SEQ ID NO: 66          moltype = DNA  length = 312
FEATURE                Location/Qualifiers
source                 1..312
                       mol_type = genomic DNA
                       organism = Listeria monocytogenes
SEQUENCE: 66
atgcatgtca aaaaaggtga taaagtaaaa gttattactg gtaaagataa aggcaaattc  60
ggcaaagtgc tcgcagcatt tccgaaaaag gaccgcgtac ttatcgaagg aatcaatatg  120
gttaaaaaac atacaaaacc ttccaacatc aacccgcaag gcggaatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                      312

SEQ ID NO: 67          moltype = DNA  length = 312
FEATURE                Location/Qualifiers
source                 1..312
                       mol_type = genomic DNA
                       organism = Listeria monocytogenes
```

```
SEQUENCE: 67
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta cttgacccta aaacaggcga acctactcgt  240
gtaggatacg aagttaaagg cgacaagaaa gtacgcgtag caaaaaaatc cggtgaagta  300
atagataaat aa                                                       312

SEQ ID NO: 68          moltype = DNA  length = 312
FEATURE                Location/Qualifiers
source                 1..312
                       mol_type = genomic DNA
                       organism = Listeria monocytogenes
SEQUENCE: 68
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta attgacccta aaacaggtga acctactcgt  240
gtaggatacg aagttaaagg cgacaaaaaa gtacgcgtag caaaaaaatc cggtgaagta  300
atagataaat aa                                                       312

SEQ ID NO: 69          moltype = DNA  length = 312
FEATURE                Location/Qualifiers
source                 1..312
                       mol_type = genomic DNA
                       organism = Listeria monocytogenes
SEQUENCE: 69
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta cttgacccta aaacaggcga acctactcgt  240
gtaggatacg aagttaaagg cgacaagaaa gtacgcgtag caaaaaaatc cggtgaagta  300
atagataaat aa                                                       312

SEQ ID NO: 70          moltype = DNA  length = 312
FEATURE                Location/Qualifiers
source                 1..312
                       mol_type = genomic DNA
                       organism = Listeria monocytogenes
SEQUENCE: 70
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta attgacccta aaacaggcga acctactcgt  240
gtaggatacg aagttaaagg cgacaaaaaa gtacgcgtag caaaaaaatc cggtgaagta  300
atagataaat aa                                                       312

SEQ ID NO: 71          moltype = DNA  length = 312
FEATURE                Location/Qualifiers
source                 1..312
                       mol_type = genomic DNA
                       organism = Listeria monocytogenes
SEQUENCE: 71
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atacaaaacc ttccaacatc aacccgcaag gcgggatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                       312

SEQ ID NO: 72          moltype = DNA  length = 312
FEATURE                Location/Qualifiers
source                 1..312
                       mol_type = genomic DNA
                       organism = Listeria monocytogenes
SEQUENCE: 72
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atacaaaacc ttccaacatc aacccgcaag gcggaatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                       312

SEQ ID NO: 73          moltype = DNA  length = 312
FEATURE                Location/Qualifiers
source                 1..312
                       mol_type = genomic DNA
                       organism = Listeria monocytogenes
```

```
SEQUENCE: 73
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atacaaaacc ttccaacatc aacccgcaag gcggaatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                      312

SEQ ID NO: 74          moltype = DNA  length = 312
FEATURE                Location/Qualifiers
source                 1..312
                       mol_type = genomic DNA
                       organism = Listeria monocytogenes
SEQUENCE: 74
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta attgacccta aaacaggtga acctactcgt  240
gtaggatacg aagttaaagg cgacaaaaaa gtacgcgtag caaaaaaatc cggtgaagta  300
atagataaat aa                                                      312

SEQ ID NO: 75          moltype = DNA  length = 312
FEATURE                Location/Qualifiers
source                 1..312
                       mol_type = genomic DNA
                       organism = Listeria monocytogenes
SEQUENCE: 75
atgcatgtca aaaaaggtga taaagtaaaa gttattactg gtaaagataa aggcaaatcc  60
ggcaaagtgc tcgcagcatt tccgaagaag gatcgcgtac ttattgaagg aattaatatg  120
gtcaaaaaac atacaaaacc ttccaacatc aacccgcaag gcggaatctt gaatgttgaa  180
gcaccaatcc atgtttcaaa cgtaatgcta attgacccta aaacaggcga acctactcgt  240
gtaggctacg aagttaaagg cgataaaaaa gtacgcgtag caaaaaaatc cggtgaagta  300
atagataaat aa                                                      312

SEQ ID NO: 76          moltype = DNA  length = 312
FEATURE                Location/Qualifiers
source                 1..312
                       mol_type = genomic DNA
                       organism = Listeria monocytogenes
SEQUENCE: 76
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atacaaaacc ttccaacatc aacccgcaag gcgggatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                      312

SEQ ID NO: 77          moltype = DNA  length = 312
FEATURE                Location/Qualifiers
source                 1..312
                       mol_type = genomic DNA
                       organism = Listeria monocytogenes
SEQUENCE: 77
atgcatgtca aaaaaggtga taaagtaaaa gttattactg gtaaagataa aggcaaatcc  60
ggcaaagtgc tcgcagcatt tccgaagaag gatcgcgtac ttattgaagg aattaatatg  120
gtcaaaaaac atacaaaacc ttccaacatc aacccgcaag gcggaatctt gaatgttgaa  180
gcaccaatcc atgtttcaaa cgtaatgcta attgacccta aaacaggcga acctactcgt  240
gtaggctacg aagttaaagg cgataaaaaa gtacgcgtag caaaaaaatc cggtgaagta  300
atagataaat aa                                                      312

SEQ ID NO: 78          moltype = DNA  length = 312
FEATURE                Location/Qualifiers
source                 1..312
                       mol_type = genomic DNA
                       organism = Listeria monocytogenes
SEQUENCE: 78
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atacaaaacc ttccaacatc aacccgcaag gcggaatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                      312

SEQ ID NO: 79          moltype = DNA  length = 312
FEATURE                Location/Qualifiers
source                 1..312
                       mol_type = genomic DNA
                       organism = Listeria monocytogenes
```

-continued

```
SEQUENCE: 79
atgcatgtca aaaaaggtga taaagtaaaa gttattactg gtaaagataa aggcaaatcc  60
ggcaaagtgc tcgcagcatt tccgaaaaag gatcgcgtac ttatcgaagg aatcaatatg  120
gttaaaaaac atacaaaacc ttccaacgtc aacccgcaag gcggaatctt gaatgttgaa  180
gcaccaatcc acgtttcaaa cgtaatgcta attgacccta aaacaggtga acctactcgt  240
gtaggatacg aagttaaagg cgacaaaaaa gtacgcgtag caaaaaaatc cggtgaagta  300
atagataaat aa                                                      312

SEQ ID NO: 80          moltype = DNA  length = 312
FEATURE                Location/Qualifiers
source                 1..312
                       mol_type = genomic DNA
                       organism = Listeria monocytogenes
SEQUENCE: 80
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atacaaaacc ttccaacatc aacccgcaag gcgggatctt gaatgttgaa  180
gcaccaatcc acgtttcaaa cgtaatgcta attgacccta aaacaggcga acctactcgt  240
gtaggatacg aagttaaagg cgataaaaaa gtacgcgtag caaaaaaatc cggtgaagta  300
atagataaat aa                                                      312

SEQ ID NO: 81          moltype = DNA  length = 537
FEATURE                Location/Qualifiers
source                 1..537
                       mol_type = genomic DNA
                       organism = Listeria monocytogenes
SEQUENCE: 81
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gataagcttg ttcttaacgt agggtactct catccagtag agtttgttgc tcctaaaggc  360
gtagatattg aagttcctgc aaacacacaa gtgattgtta aaggatacaa caaggaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 82          moltype = DNA  length = 537
FEATURE                Location/Qualifiers
source                 1..537
                       mol_type = genomic DNA
                       organism = Listeria monocytogenes
SEQUENCE: 82
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 83          moltype = DNA  length = 537
FEATURE                Location/Qualifiers
source                 1..537
                       mol_type = genomic DNA
                       organism = Listeria monocytogenes
SEQUENCE: 83
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gataagcttg ttcttaacgt agggtactct catccagtag agtttgttgc tcctaaaggc  360
gtagatattg aagttcctgc aaacacacaa gtgattgtta aaggatacaa caaggaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 84          moltype = DNA  length = 537
FEATURE                Location/Qualifiers
source                 1..537
                       mol_type = genomic DNA
                       organism = Listeria monocytogenes
SEQUENCE: 84
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
```

-continued

```
gagggttatg aaaagaaatt agaacttatc ggtgttggtt accgtgcgca aaaacaaggc  300
gataagcttg ttcttaacgt agggtactct catccagtag agtttgttgc tcctaaaggc  360
gtagatattg aagttcctgc aaacacacaa gtgattgtta aaggatacaa caaggaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 85          moltype = DNA  length = 537
FEATURE                Location/Qualifiers
source                 1..537
                       mol_type = genomic DNA
                       organism = Listeria monocytogenes
SEQUENCE: 85
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gataagcttg ttcttaacgt agggtactct catccagtag agtttgttgc tcctaaaggc  360
gtagatattg aagttcctgc aaacacacaa gtgattgtta aaggatacaa caaggaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 86          moltype = DNA  length = 537
FEATURE                Location/Qualifiers
source                 1..537
                       mol_type = genomic DNA
                       organism = Listeria monocytogenes
SEQUENCE: 86
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 87          moltype = DNA  length = 537
FEATURE                Location/Qualifiers
source                 1..537
                       mol_type = genomic DNA
                       organism = Listeria monocytogenes
SEQUENCE: 87
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 88          moltype = DNA  length = 537
FEATURE                Location/Qualifiers
source                 1..537
                       mol_type = genomic DNA
                       organism = Listeria monocytogenes
SEQUENCE: 88
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 89          moltype = DNA  length = 537
FEATURE                Location/Qualifiers
source                 1..537
                       mol_type = genomic DNA
                       organism = Listeria monocytogenes
SEQUENCE: 89
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
```

-continued

```
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 90          moltype = DNA  length = 537
FEATURE                Location/Qualifiers
source                 1..537
                       mol_type = genomic DNA
                       organism = Listeria monocytogenes
SEQUENCE: 90
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gataagcttg ttcttaacgt agggtactct catccagtag agtttgttgc tcctaaaggc  360
gtagatattg aagttcctgc aaacacacaa gtgattgtta aaggatacaa caaggaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 91          moltype = DNA  length = 537
FEATURE                Location/Qualifiers
source                 1..537
                       mol_type = genomic DNA
                       organism = Listeria monocytogenes
SEQUENCE: 91
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caatgaaatt aacgtttctc gcccgactga taataaaaac  180
caccgcgcgc ttcatggtac aactcgtgct attctaaata acatggttgt cggagtttcc  240
gagggttatg aaaagaaatt agaacttatc ggtgttggtt accgtgcgca aaaacaaggc  300
gacaagcttg ttcttaacgt agggtactct catccagtag aatttgttgc tccgaaaggc  360
gtagaaattg aagttcctgc aaacacacaa gtgattgtta aaggatacaa caaagaacac  420
gttggagaat tagctgcaaa cattcgtgcc gtacgtccac cagagccgta taaaggtaaa  480
ggtattcgtt acgaaggcga acatgtacgc cgtaaagaag gtaaaactgg taaataa     537

SEQ ID NO: 92          moltype = DNA  length = 537
FEATURE                Location/Qualifiers
source                 1..537
                       mol_type = genomic DNA
                       organism = Listeria monocytogenes
SEQUENCE: 92
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 93          moltype = DNA  length = 537
FEATURE                Location/Qualifiers
source                 1..537
                       mol_type = genomic DNA
                       organism = Listeria monocytogenes
SEQUENCE: 93
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgcgcgc ttcatggtac aactcgtgct attctaaata acatggttgt cggagtttcc  240
gagggttatg aaaagaaatt agaacttatc ggtgttggtt accgtgcgca aaaacaaggc  300
gacaagcttg ttcttaacgt agggtactct catccagtag aatttgttgc tccgaaaggc  360
gtagaaattg aagttcctgc aaacacacaa gtgattgtta aaggatacaa caaagaacac  420
gttggagaat tagctgcaaa cattcgtgcc gtacgtccac cagagccgta taaaggtaaa  480
ggtattcgtt acgaaggcga acatgtacgc cgtaaagaag gtaaaactgg taaataa     537

SEQ ID NO: 94          moltype = DNA  length = 537
FEATURE                Location/Qualifiers
source                 1..537
                       mol_type = genomic DNA
                       organism = Listeria monocytogenes
SEQUENCE: 94
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
```

-continued

```
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 95          moltype = DNA  length = 537
FEATURE                Location/Qualifiers
source                 1..537
                       mol_type = genomic DNA
                       organism = Listeria monocytogenes
SEQUENCE: 95
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta aaatcgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gataagcttg ttcttaacgt agggtactct catccagtag agtttgttgc tcctaaaggc  360
gtagatattg aagttcctgc aaacacacaa gtgattgtta aaggatacaa caaggaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 96          moltype = DNA  length = 537
FEATURE                Location/Qualifiers
source                 1..537
                       mol_type = genomic DNA
                       organism = Listeria monocytogenes
SEQUENCE: 96
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaaggc  300
gacaagcttg ttcttaacgt agggtactct catccagtag agtttgttgc tcctaaaggc  360
gtagatattg aagttcctgc aaacacacaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 97          moltype = DNA  length = 360
FEATURE                Location/Qualifiers
source                 1..360
                       mol_type = genomic DNA
                       organism = Listeria monocytogenes
SEQUENCE: 97
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 98          moltype = DNA  length = 360
FEATURE                Location/Qualifiers
source                 1..360
                       mol_type = genomic DNA
                       organism = Listeria monocytogenes
SEQUENCE: 98
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 99          moltype = DNA  length = 360
FEATURE                Location/Qualifiers
source                 1..360
                       mol_type = genomic DNA
                       organism = Listeria monocytogenes
SEQUENCE: 99
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360
```

-continued

```
SEQ ID NO: 100         moltype = DNA  length = 360
FEATURE                Location/Qualifiers
source                 1..360
                       mol_type = genomic DNA
                       organism = Listeria monocytogenes
SEQUENCE: 100
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 101         moltype = DNA  length = 360
FEATURE                Location/Qualifiers
source                 1..360
                       mol_type = genomic DNA
                       organism = Listeria monocytogenes
SEQUENCE: 101
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 102         moltype = DNA  length = 360
FEATURE                Location/Qualifiers
source                 1..360
                       mol_type = genomic DNA
                       organism = Listeria monocytogenes
SEQUENCE: 102
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 103         moltype = DNA  length = 360
FEATURE                Location/Qualifiers
source                 1..360
                       mol_type = genomic DNA
                       organism = Listeria monocytogenes
SEQUENCE: 103
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 104         moltype = DNA  length = 360
FEATURE                Location/Qualifiers
source                 1..360
                       mol_type = genomic DNA
                       organism = Listeria monocytogenes
SEQUENCE: 104
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 105         moltype = DNA  length = 360
FEATURE                Location/Qualifiers
source                 1..360
                       mol_type = genomic DNA
                       organism = Listeria monocytogenes
SEQUENCE: 105
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360
```

```
SEQ ID NO: 106          moltype = DNA  length = 360
FEATURE                 Location/Qualifiers
source                  1..360
                        mol_type = genomic DNA
                        organism = Listeria monocytogenes
SEQUENCE: 106
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 107          moltype = DNA  length = 360
FEATURE                 Location/Qualifiers
source                  1..360
                        mol_type = genomic DNA
                        organism = Listeria monocytogenes
SEQUENCE: 107
gtgattacca aaatcgacaa aaataaagta cgtaaaaaaa gacatgctcg tgttcgttct  60
aagatttccg gaactgaaag tcgtccacgt ttaaacgtat tccgttcaaa caaaaacatt  120
tatgctcaag taattgatga tgtaaatggt gtgacacttg caagtgcgtc taatttagat  180
aaagatttcg gttctgttga atcaaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 108          moltype = DNA  length = 360
FEATURE                 Location/Qualifiers
source                  1..360
                        mol_type = genomic DNA
                        organism = Listeria monocytogenes
SEQUENCE: 108
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 109          moltype = DNA  length = 360
FEATURE                 Location/Qualifiers
source                  1..360
                        mol_type = genomic DNA
                        organism = Listeria monocytogenes
SEQUENCE: 109
gtgattacca aaatcgacaa aaataaagta cgtaaaaaaa gacatgctcg tgttcgttct  60
aagatttccg gaactgaaag tcgtccacgt ttaaacgtat tccgttcaaa caaaaacatt  120
tatgctcaag taattgatga tgtaaatggt gtgacacttg caagtgcgtc taatttagat  180
aaagatttcg gttctgttga atcaaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 110          moltype = DNA  length = 360
FEATURE                 Location/Qualifiers
source                  1..360
                        mol_type = genomic DNA
                        organism = Listeria monocytogenes
SEQUENCE: 110
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 111          moltype = DNA  length = 360
FEATURE                 Location/Qualifiers
source                  1..360
                        mol_type = genomic DNA
                        organism = Listeria monocytogenes
SEQUENCE: 111
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360
```

```
SEQ ID NO: 112         moltype = DNA  length = 360
FEATURE                Location/Qualifiers
source                 1..360
                       mol_type = genomic DNA
                       organism = Listeria monocytogenes
SEQUENCE: 112
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtgaaagc tcttgctgaa gcagctcgcg aaaatggact agaattttaa  360

SEQ ID NO: 113         moltype = DNA  length = 504
FEATURE                Location/Qualifiers
source                 1..504
                       mol_type = genomic DNA
                       organism = Listeria monocytogenes
SEQUENCE: 113
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                        504

SEQ ID NO: 114         moltype = DNA  length = 504
FEATURE                Location/Qualifiers
source                 1..504
                       mol_type = genomic DNA
                       organism = Listeria monocytogenes
SEQUENCE: 114
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                        504

SEQ ID NO: 115         moltype = DNA  length = 504
FEATURE                Location/Qualifiers
source                 1..504
                       mol_type = genomic DNA
                       organism = Listeria monocytogenes
SEQUENCE: 115
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                        504

SEQ ID NO: 116         moltype = DNA  length = 504
FEATURE                Location/Qualifiers
source                 1..504
                       mol_type = genomic DNA
                       organism = Listeria monocytogenes
SEQUENCE: 116
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                        504

SEQ ID NO: 117         moltype = DNA  length = 504
FEATURE                Location/Qualifiers
```

-continued

```
source                  1..504
                        mol_type = genomic DNA
                        organism = Listeria monocytogenes
SEQUENCE: 117
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504

SEQ ID NO: 118          moltype = DNA  length = 504
FEATURE                 Location/Qualifiers
source                  1..504
                        mol_type = genomic DNA
                        organism = Listeria monocytogenes
SEQUENCE: 118
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cacaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504

SEQ ID NO: 119          moltype = DNA  length = 504
FEATURE                 Location/Qualifiers
source                  1..504
                        mol_type = genomic DNA
                        organism = Listeria monocytogenes
SEQUENCE: 119
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504

SEQ ID NO: 120          moltype = DNA  length = 504
FEATURE                 Location/Qualifiers
source                  1..504
                        mol_type = genomic DNA
                        organism = Listeria monocytogenes
SEQUENCE: 120
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504

SEQ ID NO: 121          moltype = DNA  length = 504
FEATURE                 Location/Qualifiers
source                  1..504
                        mol_type = genomic DNA
                        organism = Listeria monocytogenes
SEQUENCE: 121
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504
```

```
SEQ ID NO: 122         moltype = DNA  length = 504
FEATURE                Location/Qualifiers
source                 1..504
                       mol_type = genomic DNA
                       organism = Listeria monocytogenes
SEQUENCE: 122
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                          504

SEQ ID NO: 123         moltype = DNA  length = 504
FEATURE                Location/Qualifiers
source                 1..504
                       mol_type = genomic DNA
                       organism = Listeria monocytogenes
SEQUENCE: 123
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cacaagaagt tccagatgca  180
atccgcaaag ctgttgagga tgctaaaaag aacatggtgc ttgtaccaac tgtaaacaca  240
actattccac acactgtagt cggacatttt ggtggcggag aaattcttct taaacctgct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca acttaaaaac gctgaagatg ttgcgaaact tcgtggcaaa  480
acagtagaag aattgttagg ataa                                          504

SEQ ID NO: 124         moltype = DNA  length = 504
FEATURE                Location/Qualifiers
source                 1..504
                       mol_type = genomic DNA
                       organism = Listeria monocytogenes
SEQUENCE: 124
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                          504

SEQ ID NO: 125         moltype = DNA  length = 504
FEATURE                Location/Qualifiers
source                 1..504
                       mol_type = genomic DNA
                       organism = Listeria monocytogenes
SEQUENCE: 125
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cacaagaagt tccagatgca  180
atccgcaaag ctgttgagga tgctaaaaag aacatggtgc ttgtaccaac tgtaaacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca acttaaaaac gctgaagatg ttgcgaaact tcgtggcaaa  480
acagtagaag aattgttagg ataa                                          504

SEQ ID NO: 126         moltype = DNA  length = 504
FEATURE                Location/Qualifiers
source                 1..504
                       mol_type = genomic DNA
                       organism = Listeria monocytogenes
SEQUENCE: 126
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
```

```
acaatcgacg gaattaaaca actgaaaaac gctgaagatg ttgcgaaact tcgtggcaaa  480
acagtagaag aattgttagg ataa                                         504

SEQ ID NO: 127         moltype = DNA  length = 504
FEATURE                Location/Qualifiers
source                 1..504
                       mol_type = genomic DNA
                       organism = Listeria monocytogenes
SEQUENCE: 127
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaacctgct  300
agtgccggtt ctggtgtaac tgctggtggt cccgttcgtg cggtcctaga acttgctggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504

SEQ ID NO: 128         moltype = DNA  length = 504
FEATURE                Location/Qualifiers
source                 1..504
                       mol_type = genomic DNA
                       organism = Listeria monocytogenes
SEQUENCE: 128
atgcctgagc aaattgatgg aaacaaatta gatttagaag aacgcgttgt tacaatcaac  60
cgtgttgcta aagtagttaa aggtggacgt cgtttccgtt tcacagcact tgttgttgtt  120
ggagacaaaa atggtcatgt tggtttcggt actggtaaag cgcaagaagt tccagatgct  180
atccgtaaag ctgttgagga tgctaaaaag aacatggtgc ttgtaccaac tgtagacaca  240
actattccac acactgtagt cggacatttt ggtggcggag aaattcttct taaaccagct  300
agtgccggtt ctggtgtaac tgctggtggt cccgttcgtg cggtcctaga acttgccggt  360
gttgctgatg tatcttccaa atcgcttgga tctaatacac caattaacat ggtacgtgct  420
acaatcgacg gaattaaaca actgaaaaac gctgaagatg ttgcgaaact tcgtggcaaa  480
acagtagaag aattgttagg ataa                                         504

SEQ ID NO: 129         moltype = DNA  length = 441
FEATURE                Location/Qualifiers
source                 1..441
                       mol_type = genomic DNA
                       organism = Listeria monocytogenes
SEQUENCE: 129
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggtttt gaaggtggac aacttccact tttccgtcgt  180
attccaaaac gtggattcac aaatatcaac cgtaaagaat ttgctatcgt gaacttagat  240
gttttaaacc gctttgaaga tggtacagaa gtaacaccag aacttttagt tgaaactgga  300
attattcgta atgaaaaatc cggaatcaag attttatcta atggaaatat cgagaaaaaa  360
cttactgtga aagcgaacaa attctctgca gctgcgaaag aagcaattga agcagctggc  420
ggaaaaactg aggtgatcta a                                            441

SEQ ID NO: 130         moltype = DNA  length = 441
FEATURE                Location/Qualifiers
source                 1..441
                       mol_type = genomic DNA
                       organism = Listeria monocytogenes
SEQUENCE: 130
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggcttt gaaggtggac aacttccact tttccgtcgt  180
attccaaaac gtggattcac aaatatcaac cgtaaagaat ttgctatcgt gaacttagat  240
gttttaaacc gctttgaaga tggtacagaa gtaacaccag aacttttagt tgaaactgga  300
attattcgta atgaaaaatc cggaatcaag attttatcta atggaaatat cgagaaaaaa  360
cttactgtga aagcgaacaa attctctgca gctgcgaaag aagcaattga agcggctggc  420
ggaaaaactg aggtgatcta a                                            441

SEQ ID NO: 131         moltype = DNA  length = 441
FEATURE                Location/Qualifiers
source                 1..441
                       mol_type = genomic DNA
                       organism = Listeria monocytogenes
SEQUENCE: 131
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggtttt gaaggtggac aacttccact tttccgtcgt  180
attccaaaac gtggattcac aaatatcaac cgtaaagaat ttgctatcgt gaacttagat  240
gttttaaacc gctttgaaga tggtacagaa gtaacaccag aacttttagt tgaaactgga  300
attattcgta atgaaaaatc cggaatcaag attttatcta atggaaatat cgagaaaaaa  360
cttactgtga aagcgaacaa attctctgca gctgcgaaag aagcaattga agcagctggc  420
ggaaaaactg aggtgatcta a                                            441
```

SEQ ID NO: 132 moltype = DNA length = 441
FEATURE Location/Qualifiers
source 1..441
mol_type = genomic DNA
organism = Listeria monocytogenes
SEQUENCE: 132
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggtttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcagctggc 420
ggaaaaactg aggtgatcta a 441

SEQ ID NO: 133 moltype = DNA length = 441
FEATURE Location/Qualifiers
source 1..441
mol_type = genomic DNA
organism = Listeria monocytogenes
SEQUENCE: 133
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggtttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcagctggc 420
ggaaaaactg aggtgatcta a 441

SEQ ID NO: 134 moltype = DNA length = 441
FEATURE Location/Qualifiers
source 1..441
mol_type = genomic DNA
organism = Listeria monocytogenes
SEQUENCE: 134
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggtttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta acgaaaaatc cggaatcaag attttatcta atggaaatat cgagaaaaaa 360
cttactgtga aagcgaacaa attctctgca gctgccaaag aagcaatcga agcagctggc 420
ggaaaaactg aggtgatcta a 441

SEQ ID NO: 135 moltype = DNA length = 441
FEATURE Location/Qualifiers
source 1..441
mol_type = genomic DNA
organism = Listeria monocytogenes
SEQUENCE: 135
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggcttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcggctggc 420
ggaaaaactg aggtgatcta a 441

SEQ ID NO: 136 moltype = DNA length = 441
FEATURE Location/Qualifiers
source 1..441
mol_type = genomic DNA
organism = Listeria monocytogenes
SEQUENCE: 136
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggcttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcggctggc 420
ggaaaaactg aggtgatcta a 441

SEQ ID NO: 137 moltype = DNA length = 441
FEATURE Location/Qualifiers
source 1..441

```
                       mol_type = genomic DNA
                       organism = Listeria monocytogenes
SEQUENCE: 137
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggcttt gaaggtggac aacttccact tttccgtcgt  180
attccaaaac gtggattcac aaatatcaac cgtaaagaat ttgctatcgt gaacttagat  240
gttttaaacc gctttgaaga tggtacagaa gtaacaccag aactttagt tgaaactgga  300
attattcgta atgaaaaatc cggaatcaag attttatcta atggaaatat cgagaaaaaa  360
cttactgtga aagcgaacaa attctctgca gctgcgaaag aagcaattga agcggctggc  420
ggaaaaactg aggtgatcta a                                          441

SEQ ID NO: 138         moltype = DNA  length = 441
FEATURE                Location/Qualifiers
source                 1..441
                       mol_type = genomic DNA
                       organism = Listeria monocytogenes
SEQUENCE: 138
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggtttt gaaggtggac aacttccact tttccgtcgt  180
attccaaaac gtggattcac aaatatcaac cgtaaagaat ttgctatcgt gaacttagat  240
gttttaaacc gctttgaaga tggtacagaa gtaacaccag aacttttagt tgaaactgga  300
attattcgta atgaaaaatc cggaatcaag attttatcta atggaaatat cgagaaaaaa  360
cttactgtga aagcgaacaa attctctgca gctgcgaaag aagcaattga agcagctggc  420
ggaaaaactg aggtgatcta a                                          441

SEQ ID NO: 139         moltype = DNA  length = 441
FEATURE                Location/Qualifiers
source                 1..441
                       mol_type = genomic DNA
                       organism = Listeria monocytogenes
SEQUENCE: 139
atgaaactac atgaacttaa gccttcagaa ggttctcgaa aagaacgtaa tcgtgttggt  60
cgtggaacag gctctggtaa cggcaaaact tcaggacgcg gtcataaagg acaaaaagct  120
cgttccggtg gtggcgtacg tttaggtttt gaaggtggac aacttccact tttccgtcgt  180
attccaaaac gtggattcac aaatatcaac cgtaaagaat ttgcaatcgt gaacttagat  240
gttttaaacc gctttgaaga cggtacagaa gtaacaccag aacttttaat tgaatctgga  300
attattcgta acgaaaaatc cggaatcaag attttatctg atggtaaaat cgagaaaaaa  360
cttactgtga aagcgaacaa attctctgca gctgcaaaag aagctattga agcggctggc  420
ggaaaaactg aggtgatcta a                                          441

SEQ ID NO: 140         moltype = DNA  length = 441
FEATURE                Location/Qualifiers
source                 1..441
                       mol_type = genomic DNA
                       organism = Listeria monocytogenes
SEQUENCE: 140
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggcttt gaaggtggac aacttccact tttccgtcgt  180
attccaaaac gtggattcac aaatatcaac cgtaaagaat ttgctatcgt gaacttagat  240
gttttaaacc gctttgaaga tggtacagaa gtaacaccag aacttttagt tgaaactgga  300
attattcgta atgaaaaatc cggaatcaag attttatcta atggaaatat cgagaaaaaa  360
cttactgtga aagcgaacaa attctctgca gctgcgaaag aagcaattga agcggctggc  420
ggaaaaactg aggtgatcta a                                          441

SEQ ID NO: 141         moltype = DNA  length = 441
FEATURE                Location/Qualifiers
source                 1..441
                       mol_type = genomic DNA
                       organism = Listeria monocytogenes
SEQUENCE: 141
atgaaactac atgaacttaa gccttcagaa ggttctcgaa aagaacgtaa tcgtgttggt  60
cgtggaacag gctctggtaa cggcaaaact tcaggacgcg gtcataaagg acaaaaagct  120
cgttccggtg gtggcgtacg tttaggtttt gaaggtggac aacttccact tttccgtcgt  180
attccaaaac gtggattcac aaatatcaac cgtaaagaat ttgcaatcgt gaacttagat  240
gttttaaacc gctttgaaga cggtacagaa gtaacaccag aacttttaat tgaatctgga  300
attattcgta acgaaaaatc cggaatcaag attttatctg atggtaaaat cgagaaaaaa  360
cttactgtga aagcgaacaa attctctgca gctgcaaaag aagctattga agcggctggc  420
ggaaaaactg aggtgatcta a                                          441

SEQ ID NO: 142         moltype = DNA  length = 441
FEATURE                Location/Qualifiers
source                 1..441
                       mol_type = genomic DNA
                       organism = Listeria monocytogenes
```

SEQUENCE: 142
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggcttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcggctggc 420
ggaaaaactg aggtgatcta a 441

SEQ ID NO: 143 moltype = DNA length = 441
FEATURE Location/Qualifiers
source 1..441
mol_type = genomic DNA
organism = Listeria monocytogenes
SEQUENCE: 143
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggtttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcagctggc 420
ggaaaaactg aggtgatcta a 441

SEQ ID NO: 144 moltype = DNA length = 441
FEATURE Location/Qualifiers
source 1..441
mol_type = genomic DNA
organism = Listeria monocytogenes
SEQUENCE: 144
atgaaactac atgaacttaa gccttcagaa ggttctcgta aagaacgtaa tcgtgttggt 60
cgtggaacag gctctggtaa cggcaaaact tcaggacgcg gtcataaagg acaaaaagct 120
cgttctggtg gtggcgtacg tttaggcttt gaaggtggac aacttccact tttccgtcgt 180
attccaaaac gtggattcac aaatatcaac cgtaaagaat ttgctatcgt gaacttagat 240
gttttaaacc gctttgaaga tggtacagaa gtaacaccag aacttttagt tgaaactgga 300
attattcgta atgaaaaatc cggaatcaag attttatcta atggaaatat cgagaaaaaa 360
cttactgtga aagcgaacaa attctctgca gctgcgaaag aagcaattga agcggctggc 420
ggaaaaactg aggtgatcta a 441

SEQ ID NO: 145 moltype = DNA length = 366
FEATURE Location/Qualifiers
source 1..366
mol_type = genomic DNA
organism = Listeria monocytogenes
SEQUENCE: 145
atggcacgta ttgcaggtgt ggacgttcca cgtgaaaaac gtattgttat ttccctgact 60
tacatttatg gtatcggtaa acaaacagct aaagaagttc ttgctgaagc tggcgtttct 120
gaagatactc gtactcgtga tttaactgaa gaagagctag gtaaaatccg tgaaatctta 180
gaccgtatta aagttgaagg tgaccttcgt cgtgaagtaa acttaaacat taaacgtcta 240
atcgaaatcg gttcttaccg tggcatgcgt caccgtcgtg gacttccagt tcgcggacaa 300
aatacaaaaa ataatgcccg tactcgtaaa ggcccgtcca aaacagtagc aggcaaaaag 360
aaataa 366

SEQ ID NO: 146 moltype = DNA length = 366
FEATURE Location/Qualifiers
source 1..366
mol_type = genomic DNA
organism = Listeria monocytogenes
SEQUENCE: 146
atggcacgta ttgcaggtgt ggacgttcca cgtgaaaaac gtattgttat ttccctgact 60
tacatttatg gtatcggtaa acaaacagct aaagaagttc ttgctgaagc tggcgtttct 120
gaagatactc gtactcgtga tttaactgaa gaagagctag gtaaaatccg tgaaatctta 180
gaccgtatta aagttgaagg tgaccttcgt cgtgaagtaa acttaaacat taaacgtcta 240
atcgaaatcg gttcttaccg tggcatgcgt caccgtcgtg gacttccagt tcgcggacaa 300
aatacaaaaa ataatgcccg tactcgtaaa ggcccgtcca aaacagtagc aggcaaaaag 360
aaataa 366

SEQ ID NO: 147 moltype = DNA length = 366
FEATURE Location/Qualifiers
source 1..366
mol_type = genomic DNA
organism = Listeria monocytogenes
SEQUENCE: 147
atggcacgta ttgcaggtgt ggacgttcca cgtgaaaaac gtattgttat ttccctgact 60
tacatttatg gtatcggtaa acaaacagct aaagaagttc ttgctgaagc tggcgtttct 120
gaagatactc gtactcgtga tttaactgaa gaagagctag gtaaaatccg tgaaatctta 180
gaccgtatta aagttgaagg tgaccttcgt cgtgaagtaa acttaaacat taaacgtcta 240
atcgaaatcg gttcttaccg tggcatgcgt caccgtcgtg gacttccagt tcgcggacaa 300

```
aatacaaaaa ataatgcccg tactcgtaaa ggcccgtcca aaacagtagc aggcaaaaag  360
aaataa                                                             366

SEQ ID NO: 148         moltype = DNA  length = 366
FEATURE                Location/Qualifiers
source                 1..366
                       mol_type = genomic DNA
                       organism = Listeria monocytogenes
SEQUENCE: 148
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                             366

SEQ ID NO: 149         moltype = DNA  length = 366
FEATURE                Location/Qualifiers
source                 1..366
                       mol_type = genomic DNA
                       organism = Listeria monocytogenes
SEQUENCE: 149
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                             366

SEQ ID NO: 150         moltype = DNA  length = 366
FEATURE                Location/Qualifiers
source                 1..366
                       mol_type = genomic DNA
                       organism = Listeria monocytogenes
SEQUENCE: 150
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagcttg gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                             366

SEQ ID NO: 151         moltype = DNA  length = 366
FEATURE                Location/Qualifiers
source                 1..366
                       mol_type = genomic DNA
                       organism = Listeria monocytogenes
SEQUENCE: 151
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                             366

SEQ ID NO: 152         moltype = DNA  length = 366
FEATURE                Location/Qualifiers
source                 1..366
                       mol_type = genomic DNA
                       organism = Listeria monocytogenes
SEQUENCE: 152
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                             366

SEQ ID NO: 153         moltype = DNA  length = 366
FEATURE                Location/Qualifiers
source                 1..366
                       mol_type = genomic DNA
                       organism = Listeria monocytogenes
```

-continued

```
SEQUENCE: 153
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                            366

SEQ ID NO: 154         moltype = DNA  length = 366
FEATURE                Location/Qualifiers
source                 1..366
                       mol_type = genomic DNA
                       organism = Listeria monocytogenes
SEQUENCE: 154
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                            366

SEQ ID NO: 155         moltype = DNA  length = 366
FEATURE                Location/Qualifiers
source                 1..366
                       mol_type = genomic DNA
                       organism = Listeria monocytogenes
SEQUENCE: 155
atggcacgta ttgcaggtgt ggacgttcca cgtgaaaaac gtattgttat ttccctgact  60
tacatttatg gtatcggtaa acaaacagct agcaaagttc ttgctgaagc tggtgtttct  120
gaagatactc gtactcgtga tttaactgaa gaagagctag gtaaaatccg cgaaatctta  180
gaccgcatta aagttgaagg tgaccttcgt cgtgaagtaa acttaaacat taaacgtcta  240
attgaaatcg gttcttaccg tggcatgcgt caccgtcgtg gacttccagt tcgcggacaa  300
aatacaaaaa ataatgcccg tactcgtaaa ggcccgtcca aaacagtatc aggcaaaaag  360
aaataa                                                            366

SEQ ID NO: 156         moltype = DNA  length = 366
FEATURE                Location/Qualifiers
source                 1..366
                       mol_type = genomic DNA
                       organism = Listeria monocytogenes
SEQUENCE: 156
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                            366

SEQ ID NO: 157         moltype = DNA  length = 366
FEATURE                Location/Qualifiers
source                 1..366
                       mol_type = genomic DNA
                       organism = Listeria monocytogenes
SEQUENCE: 157
atggcacgta ttgcaggtgt ggacgttcca cgtgaaaaac gtattgttat ttccctgact  60
tacatttatg gtatcggtaa acaaacagct agcaaagttc ttgctgaagc tggtgtttct  120
gaagatactc gtactcgtga tttaactgaa gaagagctag gtaaaatccg cgaaatctta  180
gaccgcatta aagttgaagg tgaccttcgt cgtgaagtaa acttaaacat taaacgtcta  240
attgaaatcg gttcttaccg tggcatgcgt caccgtcgtg gacttccagt tcgcggacaa  300
aatacaaaaa ataatgcccg tactcgtaaa ggcccgtcca aaacagtatc aggcaaaaag  360
aaataa                                                            366

SEQ ID NO: 158         moltype = DNA  length = 366
FEATURE                Location/Qualifiers
source                 1..366
                       mol_type = genomic DNA
                       organism = Listeria monocytogenes
SEQUENCE: 158
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                            366
```

```
SEQ ID NO: 159          moltype = DNA  length = 366
FEATURE                 Location/Qualifiers
source                  1..366
                        mol_type = genomic DNA
                        organism = Listeria monocytogenes
SEQUENCE: 159
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                              366

SEQ ID NO: 160          moltype = DNA  length = 366
FEATURE                 Location/Qualifiers
source                  1..366
                        mol_type = genomic DNA
                        organism = Listeria monocytogenes
SEQUENCE: 160
atggcacgta ttgcaggtgt ggacgttcca cgtgaaaaac gtattgttat ttccctgact  60
tacatttatg gtatcggtaa acaaacagct aaagaagttc ttgctgaagc tggcgtttct  120
gaagatactc gtactcgtga tttaactgaa gaagagctag gtaaaatccg tgaaatctta  180
gaccgtatta aagttgaagg tgaccttcgt cgtgaagtaa acttaaacat taaacgtcta  240
atcgaaatcg gttcttaccg tggcatgcgt caccgtcgtg gacttccagt tcgcggacaa  300
aatacaaaaa ataatgcccg tactcgtaaa ggcccgtcca aaacagtagc aggcaaaaag  360
aaataa                                                              366

SEQ ID NO: 161          moltype = DNA  length = 390
FEATURE                 Location/Qualifiers
source                  1..390
                        mol_type = genomic DNA
                        organism = Listeria monocytogenes
SEQUENCE: 161
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                  390

SEQ ID NO: 162          moltype = DNA  length = 390
FEATURE                 Location/Qualifiers
source                  1..390
                        mol_type = genomic DNA
                        organism = Listeria monocytogenes
SEQUENCE: 162
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                  390

SEQ ID NO: 163          moltype = DNA  length = 390
FEATURE                 Location/Qualifiers
source                  1..390
                        mol_type = genomic DNA
                        organism = Listeria monocytogenes
SEQUENCE: 163
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                  390

SEQ ID NO: 164          moltype = DNA  length = 390
FEATURE                 Location/Qualifiers
source                  1..390
                        mol_type = genomic DNA
                        organism = Listeria monocytogenes
SEQUENCE: 164
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
```

-continued

```
ttcgcagcgc aaatggcagc tgaaagtgca gcaaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                    390

SEQ ID NO: 165         moltype = DNA  length = 390
FEATURE                Location/Qualifiers
source                 1..390
                       mol_type = genomic DNA
                       organism = Listeria monocytogenes
SEQUENCE: 165
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                    390

SEQ ID NO: 166         moltype = DNA  length = 390
FEATURE                Location/Qualifiers
source                 1..390
                       mol_type = genomic DNA
                       organism = Listeria monocytogenes
SEQUENCE: 166
atggctcgta aaacaaatac tcgtaaacgc cgtgtgaaaa agaatatcga atccggtatt  60
gcacacattc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                    390

SEQ ID NO: 167         moltype = DNA  length = 390
FEATURE                Location/Qualifiers
source                 1..390
                       mol_type = genomic DNA
                       organism = Listeria monocytogenes
SEQUENCE: 167
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                    390

SEQ ID NO: 168         moltype = DNA  length = 390
FEATURE                Location/Qualifiers
source                 1..390
                       mol_type = genomic DNA
                       organism = Listeria monocytogenes
SEQUENCE: 168
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                    390

SEQ ID NO: 169         moltype = DNA  length = 390
FEATURE                Location/Qualifiers
source                 1..390
                       mol_type = genomic DNA
                       organism = Listeria monocytogenes
SEQUENCE: 169
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                    390
```

-continued

```
SEQ ID NO: 170         moltype = DNA  length = 390
FEATURE                Location/Qualifiers
source                 1..390
                       mol_type = genomic DNA
                       organism = Listeria monocytogenes
SEQUENCE: 170
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 171         moltype = DNA  length = 390
FEATURE                Location/Qualifiers
source                 1..390
                       mol_type = genomic DNA
                       organism = Listeria monocytogenes
SEQUENCE: 171
atggctcgta aaacaaatac tcgtaaacgc cgtgtgaaaa agaatatcga atctggtatt  60
gcacacattc gttctacatt taataatacg atcgtaatga ttactgacac acagggtaat  120
gctttagctt ggtcaagtgc aggttctcta ggatttaaag gttctcgtaa atctactcct  180
ttcgcagcgc aaatggcagc tgaaagtgca gctaagtcag cacaagaaca tggtttgaaa  240
acattagaag taacggttaa aggtcctggt tcaggtcgtg aagcggctat ccgtgcacta  300
caagcagctg gtcttgaagt aacagctatt agagatgtaa ctccagttcc acataacgga  360
tgtcgtcctc caaaacgtcg tcgcgtataa                                   390

SEQ ID NO: 172         moltype = DNA  length = 390
FEATURE                Location/Qualifiers
source                 1..390
                       mol_type = genomic DNA
                       organism = Listeria monocytogenes
SEQUENCE: 172
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 173         moltype = DNA  length = 390
FEATURE                Location/Qualifiers
source                 1..390
                       mol_type = genomic DNA
                       organism = Listeria monocytogenes
SEQUENCE: 173
atggctcgta aaacaaatac tcgtaaacgc cgtgtgaaaa agaatatcga atctggtatt  60
gcacacattc gttctacatt taataatacg atcgtaatga ttactgacac acagggtaat  120
gctttagctt ggtcaagtgc aggttctcta ggatttaaag gttctcgtaa atctactcct  180
ttcgcagcgc aaatggcagc tgaaagtgca gctaagtcag cacaagaaca tggtttgaaa  240
acattagaag taacggttaa aggtcctggt tcaggtcgtg aagcggctat ccgtgcacta  300
caagcagctg gtcttgaagt aacagctatt agagatgtaa ctccagttcc acataacgga  360
tgtcgtcctc caaaacgtcg tcgcgtataa                                   390

SEQ ID NO: 174         moltype = DNA  length = 390
FEATURE                Location/Qualifiers
source                 1..390
                       mol_type = genomic DNA
                       organism = Listeria monocytogenes
SEQUENCE: 174
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 175         moltype = DNA  length = 390
FEATURE                Location/Qualifiers
source                 1..390
                       mol_type = genomic DNA
                       organism = Listeria monocytogenes
SEQUENCE: 175
atggctcgta aaacaaatac tcgtaaacgc cgtgtgaaaa agaatatcga atctggtatt  60
gcacacatcc gttctacatt taataatacg atcgtaatga ttactgacac acatggtaat  120
```

```
gctttagctt ggtcaagtgc aggttcccta ggatttaaag gttctcgtaa atctactcct  180
ttcgcagcgc aaatggcagc tgaaagtgca gcaaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 176         moltype = DNA  length = 390
FEATURE                Location/Qualifiers
source                 1..390
                       mol_type = genomic DNA
                       organism = Listeria monocytogenes
SEQUENCE: 176
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 177         moltype = DNA  length = 390
FEATURE                Location/Qualifiers
source                 1..390
                       mol_type = genomic DNA
                       organism = Listeria monocytogenes
SEQUENCE: 177
atggctcgta aaacaaatac tcgtaaacgc cgtgtgaaaa agaatatcga atctggtatt  60
gcacacatcc gttctacatt taataatacg atcgtaatga ttactgacac acatggtaat  120
gctttagctt ggtcaagtgc aggttcccta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 178         moltype = DNA  length = 501
FEATURE                Location/Qualifiers
source                 1..501
                       mol_type = genomic DNA
                       organism = Listeria monocytogenes
SEQUENCE: 178
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                            501

SEQ ID NO: 179         moltype = DNA  length = 501
FEATURE                Location/Qualifiers
source                 1..501
                       mol_type = genomic DNA
                       organism = Listeria monocytogenes
SEQUENCE: 179
atgagtaaag ttcttgaagc taaacaaagt gcagtagaag aaattaaaac aaaattatca  60
gctagtgcgt ctacagtaat tgttgattac cgcggcttaa acgttggcga aatcactgac  120
ttacgtaaac aattgcgtga tgctggtatt gagtttaaag tttacaaaaa ctcactaact  180
cgccgtgctg ttgaagctaa cggttacgaa ggtttagaag gagctctaac tggtcctaac  240
gcaatcgcat tcagtaatga agacgtagtt gcgcctgcga aaattcttaa cgatttcgct  300
aaagatcacg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                            501

SEQ ID NO: 180         moltype = DNA  length = 501
FEATURE                Location/Qualifiers
source                 1..501
                       mol_type = genomic DNA
                       organism = Listeria monocytogenes
SEQUENCE: 180
atgagtaaag ttcttgaagc taaacaaagt gcagtagaag aaattaaaac aaaattatca  60
gctagtgcgt ctacagtaat tgttgattac cgcggcttaa acgttggcga aatcactgac  120
ttacgtaaac aattgcgtga tgctggtatt gagtttaaag tttacaaaaa ctcactaact  180
cgccgtgctg ttgaagctaa cggttacgaa ggtttagaag gagctctaac tggtcctaac  240
gcaatcgcat tcagtaatga agacgtagtt gcgcctgcga aaattcttaa cgatttcgct  300
aaagatcacg aagcactaga aatcaaagcc ggtgttattg aaggtaaagt tgcttctctt  360
gaagaaatta aagcacttgc aacacttcca tcacgcgaag gattgctatc tatgctttgc  420
```

-continued

```
aacgtacttc aagctccagt tcgcggtctt gctatcgcta ctaaagctgt tgctgaccaa  480
aaagaaggac aagaagcata a                                             501

SEQ ID NO: 181         moltype = DNA  length = 501
FEATURE                Location/Qualifiers
source                 1..501
                       mol_type = genomic DNA
                       organism = Listeria monocytogenes
SEQUENCE: 181
atgagtaaag ttcttgaagc taaacaaagt gcagtagaag aaattaaaac aaaattatca  60
gctagtgcgt ctacagtaat tgttgattac cgcggcttaa acgttggcga aatcactgac  120
ttacgtaaac aattgcgtga tgctggtatt gagtttaaag tttacaaaaa ctcactaact  180
cgccgtgctg ttgaagctaa cggttacgaa ggtttagaag gagctctaac tggtcctaac  240
gcaatcgcat tcagtaatga agacgtagtt gcgcctgcga aaattcttaa cgatttcgct  300
aaagatcacg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                             501

SEQ ID NO: 182         moltype = DNA  length = 501
FEATURE                Location/Qualifiers
source                 1..501
                       mol_type = genomic DNA
                       organism = Listeria monocytogenes
SEQUENCE: 182
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagctctaac tggtcctaac  240
gcaatcgcat tcagtaatga agacgtagtt gcgcctgcga aaatccttaa cgatttcgct  300
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                             501

SEQ ID NO: 183         moltype = DNA  length = 501
FEATURE                Location/Qualifiers
source                 1..501
                       mol_type = genomic DNA
                       organism = Listeria monocytogenes
SEQUENCE: 183
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                             501

SEQ ID NO: 184         moltype = DNA  length = 501
FEATURE                Location/Qualifiers
source                 1..501
                       mol_type = genomic DNA
                       organism = Listeria monocytogenes
SEQUENCE: 184
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                             501

SEQ ID NO: 185         moltype = DNA  length = 501
FEATURE                Location/Qualifiers
source                 1..501
                       mol_type = genomic DNA
                       organism = Listeria monocytogenes
SEQUENCE: 185
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
aaagatcatg aagcactaga aatcaaagcc ggtgttattg aaggtaaagt tgcttctctt  360
```

-continued

```
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                            501

SEQ ID NO: 186         moltype = DNA  length = 501
FEATURE                Location/Qualifiers
source                 1..501
                       mol_type = genomic DNA
                       organism = Listeria monocytogenes
SEQUENCE: 186
atgagtaaag ttcttgaagc taaacaaagt gcagtagaag aaattaaaac aaaattatca  60
gctagtgcgt ctacagtaat tgttgattac cgcggcttaa acgttggcga aatcactgac  120
ttacgtaaac aattgcgtga tgctggtatt gagtttaaag tttacaaaaa ctcactaact  180
cgccgtgctg ttgaagctaa cggttacgaa ggtttagaag gagctctaac tggtcctaac  240
gcaatcgcat tcagtaatga agacgtagtt gcgcctgcga aaattcttaa cgatttcgct  300
aaagatcacg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                            501

SEQ ID NO: 187         moltype = DNA  length = 501
FEATURE                Location/Qualifiers
source                 1..501
                       mol_type = genomic DNA
                       organism = Listeria monocytogenes
SEQUENCE: 187
atgagtaaag ttcttgaagc taaacaaagt gcagtagaag aaattaaagg taaattatca  60
gctagtgcgt ctacagtaat tgttgattac cgcggcttaa acgttggcga aatcactgaa  120
ttacgtaaac aattgcgtga cgctggtatt gaatttaaag tctacaaaaa ctcactaact  180
cgccgtgctg ttgaagctaa cggttacgaa ggtttagaag gagctctaac tggtcctaac  240
gcgatcgcat tcagtaatga agacgtagtt gcgcctgcga aaatccttaa cgatttcgct  300
aaagatcatg aagcactaga aatcaaagcg ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgatcaa  480
aaagaagaac aagaagcata a                                            501

SEQ ID NO: 188         moltype = DNA  length = 501
FEATURE                Location/Qualifiers
source                 1..501
                       mol_type = genomic DNA
                       organism = Listeria monocytogenes
SEQUENCE: 188
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                            501

SEQ ID NO: 189         moltype = DNA  length = 501
FEATURE                Location/Qualifiers
source                 1..501
                       mol_type = genomic DNA
                       organism = Listeria monocytogenes
SEQUENCE: 189
atgagtaaag ttcttgaagc taaacaaagt gcagtagaag aaattaaagg taaattatca  60
gctagtgcgt ctacagtaat tgttgattac cgcggcttaa acgttggcga aatcactgaa  120
ttacgtaaac aattgcgtga cgctggtatt gaatttaaag tctacaaaaa ctcactaact  180
cgccgtgctg ttgaagctaa cggttacgaa ggtttagaag gagctctaac tggtcctaac  240
gcgatcgcat tcagtaatga agacgtagtt gcgcctgcga aaatccttaa cgatttcgct  300
aaagatcatg aagcactaga aatcaaagcg ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgatcaa  480
aaagaagaac aagaagcata a                                            501

SEQ ID NO: 190         moltype = DNA  length = 501
FEATURE                Location/Qualifiers
source                 1..501
                       mol_type = genomic DNA
                       organism = Listeria monocytogenes
SEQUENCE: 190
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
```

```
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                           501

SEQ ID NO: 191         moltype = DNA  length = 501
FEATURE                Location/Qualifiers
source                 1..501
                       mol_type = genomic DNA
                       organism = Listeria monocytogenes
SEQUENCE: 191
atgagtaaag ttcttgaagc taaacaaagt gcagtagaag aaattaaaac aaaattatca  60
gctagtgcgt ctacagtaat tgttgattac cgcggcttaa acgttggcga aatcactgac  120
ttacgtaaac aattgcgtga tgctggtatt gagtttaaag tttacaaaaa ctcactaact  180
cgccgtgctg ttgaagctaa cggttacgaa ggtttagaag gagctctaac tggtcctaac  240
gcaatcgcat tcagtaatga agacgtagtt gcgcctgcga aaattcttaa cgatttcgct  300
aaagatcacg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                           501

SEQ ID NO: 192         moltype = DNA  length = 501
FEATURE                Location/Qualifiers
source                 1..501
                       mol_type = genomic DNA
                       organism = Listeria monocytogenes
SEQUENCE: 192
atgagtaaag ttcttgaagc taaacaaagt gcagtagaag aaattaaaac aaaattatca  60
gctagtgcgt ctacagtaat tgttgattac cgcggcttaa acgttggcga aatcactgaa  120
ttacgtaaac aattgcgtga tgctggtatt gagtttaaag tttacaaaaa ctcactaact  180
cgccgtgctg ttgaagctaa cggttatgaa ggtttagaag gagcactaac tggtcctaac  240
gcaatcgcat tcagtaatga agacgtagtt gcgcctgcga aaattcttaa cgatttcgct  300
aaagatcatg aagcactaga aatcaaagcc ggtgttattg aaggtaaagt tgcttctctt  360
gaagaaatta aagcacttgc aacacttcca tcacgcgaag gattgctatc tatgctttgc  420
aacgtacttc aagctccagt tcgcggtctt gctatcgcta ctaaagctgt tgctgaccaa  480
aaagaaggac aagaagcata a                                           501

SEQ ID NO: 193         moltype = DNA  length = 309
FEATURE                Location/Qualifiers
source                 1..309
                       mol_type = genomic DNA
                       organism = Listeria monocytogenes
SEQUENCE: 193
atgtacgcaa ttattgaaac aggtgggaaa caaatcaaag tagaagcagg ccaagagatc  60
tatgttgaga aattagcagg tgaagttgga gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                         309

SEQ ID NO: 194         moltype = DNA  length = 309
FEATURE                Location/Qualifiers
source                 1..309
                       mol_type = genomic DNA
                       organism = Listeria monocytogenes
SEQUENCE: 194
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                         309

SEQ ID NO: 195         moltype = DNA  length = 309
FEATURE                Location/Qualifiers
source                 1..309
                       mol_type = genomic DNA
                       organism = Listeria monocytogenes
SEQUENCE: 195
atgtacgcaa ttattgaaac aggtgggaaa caaatcaaag tagaagcagg ccaagagatc  60
tatgttgaga aattagcagg tgaagttgga gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                         309
```

-continued

```
SEQ ID NO: 196         moltype = DNA  length = 309
FEATURE                Location/Qualifiers
source                 1..309
                       mol_type = genomic DNA
                       organism = Listeria monocytogenes
SEQUENCE: 196
atgtacgcaa ttattgaaac aggtgggaaa caaatcaaag tagaagcagg ccaagagatc  60
tatgttgaga aattagcagg tgaagttgga gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 197         moltype = DNA  length = 309
FEATURE                Location/Qualifiers
source                 1..309
                       mol_type = genomic DNA
                       organism = Listeria monocytogenes
SEQUENCE: 197
atgtacgcaa ttattgaaac aggtgggaaa caaatcaaag tagaagcagg ccaagagatc  60
tatgttgaga aattagcagg tgaagttgga gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 198         moltype = DNA  length = 309
FEATURE                Location/Qualifiers
source                 1..309
                       mol_type = genomic DNA
                       organism = Listeria monocytogenes
SEQUENCE: 198
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 199         moltype = DNA  length = 309
FEATURE                Location/Qualifiers
source                 1..309
                       mol_type = genomic DNA
                       organism = Listeria monocytogenes
SEQUENCE: 199
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                          309

SEQ ID NO: 200         moltype = DNA  length = 309
FEATURE                Location/Qualifiers
source                 1..309
                       mol_type = genomic DNA
                       organism = Listeria monocytogenes
SEQUENCE: 200
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                          309

SEQ ID NO: 201         moltype = DNA  length = 309
FEATURE                Location/Qualifiers
source                 1..309
                       mol_type = genomic DNA
                       organism = Listeria monocytogenes
SEQUENCE: 201
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                          309
```

-continued

```
SEQ ID NO: 202          moltype = DNA  length = 309
FEATURE                 Location/Qualifiers
source                  1..309
                        mol_type = genomic DNA
                        organism = Listeria monocytogenes
SEQUENCE: 202
atgtacgcaa ttattgaaac aggtgggaaa caaatcaaag tagaagcagg ccaagagatc  60
tatgttgaga aattagcagg tgaagttgga gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 203          moltype = DNA  length = 309
FEATURE                 Location/Qualifiers
source                  1..309
                        mol_type = genomic DNA
                        organism = Listeria monocytogenes
SEQUENCE: 203
atgtacgcaa ttattgaaac aggtgggaaa caaatcaaag tagaagcagg ccaagaaatc  60
tatgttgaga aattagcagg tgaagttggt gatgttgtta cttttgacaa agttctattc  120
gtaggcggag attccgctaa agttggcgtt ccattcgtgg acggagcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 204          moltype = DNA  length = 309
FEATURE                 Location/Qualifiers
source                  1..309
                        mol_type = genomic DNA
                        organism = Listeria monocytogenes
SEQUENCE: 204
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                          309

SEQ ID NO: 205          moltype = DNA  length = 309
FEATURE                 Location/Qualifiers
source                  1..309
                        mol_type = genomic DNA
                        organism = Listeria monocytogenes
SEQUENCE: 205
atgtacgcaa ttattgaaac aggtgggaaa caaatcaaag tagaagcagg ccaagaaatc  60
tatgttgaga aattagcagg tgaagttggt gatgttgtta cttttgacaa agttctattc  120
gtaggcggag attccgctaa agttggcgtt ccattcgtgg acggagcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 206          moltype = DNA  length = 309
FEATURE                 Location/Qualifiers
source                  1..309
                        mol_type = genomic DNA
                        organism = Listeria monocytogenes
SEQUENCE: 206
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                          309

SEQ ID NO: 207          moltype = DNA  length = 309
FEATURE                 Location/Qualifiers
source                  1..309
                        mol_type = genomic DNA
                        organism = Listeria monocytogenes
SEQUENCE: 207
atgtacgcaa ttattgaaac aggtgggaaa caaatcaaag tagaagcagg ccaagagatc  60
tatgttgaga aattagcagg tgaagttgga gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgcaatc  300
aatgcttaa                                                          309

SEQ ID NO: 208          moltype = DNA  length = 309
```

```
FEATURE                Location/Qualifiers
source                 1..309
                       mol_type = genomic DNA
                       organism = Listeria monocytogenes
SEQUENCE: 208
atgtacgcaa ttattgaaac aggtgggaaa caaatcaaag tagaagcagg ccaagagatc  60
tatgttgaga aattagcagg tgaagttggt gatgttgtta cttttgacaa agttctattc  120
gtaggtggag attccgctaa agttggcgtt ccattcgtgg aaggcgcaac tgtaacagct  180
aaagttgaaa aacaaggccg tgcgaagaaa ttgacagttt ataaatataa accgaaaaag  240
aactaccaca aaaaacaagg tcatcgtcaa ccttacacaa aattaactat tgatgctatc  300
aatgcttaa                                                          309

SEQ ID NO: 209         moltype = DNA  length = 438
FEATURE                Location/Qualifiers
source                 1..438
                       mol_type = genomic DNA
                       organism = Listeria monocytogenes
SEQUENCE: 209
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 210         moltype = DNA  length = 438
FEATURE                Location/Qualifiers
source                 1..438
                       mol_type = genomic DNA
                       organism = Listeria monocytogenes
SEQUENCE: 210
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 211         moltype = DNA  length = 438
FEATURE                Location/Qualifiers
source                 1..438
                       mol_type = genomic DNA
                       organism = Listeria monocytogenes
SEQUENCE: 211
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 212         moltype = DNA  length = 438
FEATURE                Location/Qualifiers
source                 1..438
                       mol_type = genomic DNA
                       organism = Listeria monocytogenes
SEQUENCE: 212
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttgggcg tcaattattc  360
aaaaaattac acgtatatgg tggatctgag cacgaacacg cagctcaaca accagaagta  420
tacgaattac gcggttaa                                                438

SEQ ID NO: 213         moltype = DNA  length = 438
FEATURE                Location/Qualifiers
source                 1..438
                       mol_type = genomic DNA
                       organism = Listeria monocytogenes
```

```
SEQUENCE: 213
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 214         moltype = DNA  length = 438
FEATURE                Location/Qualifiers
source                 1..438
                       mol_type = genomic DNA
                       organism = Listeria monocytogenes
SEQUENCE: 214
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacatg cagctcaaca accagaagta  420
tacgaattac gcggttaa                                                438

SEQ ID NO: 215         moltype = DNA  length = 438
FEATURE                Location/Qualifiers
source                 1..438
                       mol_type = genomic DNA
                       organism = Listeria monocytogenes
SEQUENCE: 215
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggagctgag cacgaacacg cagctcaaca accagaagta  420
tacgaattac gcggttaa                                                438

SEQ ID NO: 216         moltype = DNA  length = 438
FEATURE                Location/Qualifiers
source                 1..438
                       mol_type = genomic DNA
                       organism = Listeria monocytogenes
SEQUENCE: 216
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacatg cagctcaaca accagaagta  420
tacgaattac gcggttaa                                                438

SEQ ID NO: 217         moltype = DNA  length = 438
FEATURE                Location/Qualifiers
source                 1..438
                       mol_type = genomic DNA
                       organism = Listeria monocytogenes
SEQUENCE: 217
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 218         moltype = DNA  length = 438
FEATURE                Location/Qualifiers
source                 1..438
                       mol_type = genomic DNA
                       organism = Listeria monocytogenes
SEQUENCE: 218
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
```

```
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttgggcg tcaattattc  360
aaaaaattac acgtatatgg tggatctgag cacgaacacg cagctcaaca accagaagta  420
tacgaattac gcggttaa                                                438

SEQ ID NO: 219         moltype = DNA  length = 438
FEATURE                Location/Qualifiers
source                 1..438
                       mol_type = genomic DNA
                       organism = Listeria monocytogenes
SEQUENCE: 219
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
actaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 220         moltype = DNA  length = 438
FEATURE                Location/Qualifiers
source                 1..438
                       mol_type = genomic DNA
                       organism = Listeria monocytogenes
SEQUENCE: 220
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggagctgag cacgaacacg cagctcaaca accagaagta  420
tacgaattac gcggttaa                                                438

SEQ ID NO: 221         moltype = DNA  length = 438
FEATURE                Location/Qualifiers
source                 1..438
                       mol_type = genomic DNA
                       organism = Listeria monocytogenes
SEQUENCE: 221
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
actaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacacg cagctcaaca accagaagta  420
tacgaattac gcggttaa                                                438

SEQ ID NO: 222         moltype = DNA  length = 438
FEATURE                Location/Qualifiers
source                 1..438
                       mol_type = genomic DNA
                       organism = Listeria monocytogenes
SEQUENCE: 222
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggatctgag cacgaacatg cagctcaaca accagaagta  420
tacgaattac gcggttaa                                                438

SEQ ID NO: 223         moltype = DNA  length = 438
FEATURE                Location/Qualifiers
source                 1..438
                       mol_type = genomic DNA
                       organism = Listeria monocytogenes
SEQUENCE: 223
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttgggcg tcaattattc  360
```

-continued

```
aaaaaattac acgtatatgg tggatctgag cacgaacacg cagctcaaca accagaagta  420
tacgaattac gcggttaa                                                438

SEQ ID NO: 224         moltype = DNA  length = 438
FEATURE                Location/Qualifiers
source                 1..438
                       mol_type = genomic DNA
                       organism = Listeria monocytogenes
SEQUENCE: 224
atgcgtacaa cttatatggc gaaacccggc gaagtagaac gtaaatggta cgttatcgac  60
gctactggtg tttctttagg acgtttatcc agtgaagttg cttcaattct tcgcggaaaa  120
aacaaaccac aatttactcc acatatcgac actggagact ttgtaatcat catcaacgct  180
ggtaagattg gtcttactgg taaaaaagct actgacaaaa tttactaccg tcactctcaa  240
tatccaggcg gtttgaaatc tcgtactgca ggcgaaatgc gtacaaacaa tcctgagaaa  300
ttattagaac tatctatcaa aggtatgctt ccaaaaaatt ctcttggacg tcaattattc  360
aaaaaattac acgtatatgg tggagctgag cacgaacacg cagctcaaca accagaagta  420
tacgaattac gcggttaa                                                438

SEQ ID NO: 225         moltype = DNA  length = 393
FEATURE                Location/Qualifiers
source                 1..393
                       mol_type = genomic DNA
                       organism = Listeria monocytogenes
SEQUENCE: 225
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                              393

SEQ ID NO: 226         moltype = DNA  length = 393
FEATURE                Location/Qualifiers
source                 1..393
                       mol_type = genomic DNA
                       organism = Listeria monocytogenes
SEQUENCE: 226
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
ttcgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                              393

SEQ ID NO: 227         moltype = DNA  length = 393
FEATURE                Location/Qualifiers
source                 1..393
                       mol_type = genomic DNA
                       organism = Listeria monocytogenes
SEQUENCE: 227
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                              393

SEQ ID NO: 228         moltype = DNA  length = 393
FEATURE                Location/Qualifiers
source                 1..393
                       mol_type = genomic DNA
                       organism = Listeria monocytogenes
SEQUENCE: 228
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                              393

SEQ ID NO: 229         moltype = DNA  length = 393
FEATURE                Location/Qualifiers
source                 1..393
                       mol_type = genomic DNA
                       organism = Listeria monocytogenes
```

```
SEQUENCE: 229
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                               393

SEQ ID NO: 230         moltype = DNA  length = 393
FEATURE                Location/Qualifiers
source                 1..393
                       mol_type = genomic DNA
                       organism = Listeria monocytogenes
SEQUENCE: 230
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg attgaagggc  360
gcacgtcgtg cacctcagtt ctcaaaacgt taa                               393

SEQ ID NO: 231         moltype = DNA  length = 393
FEATURE                Location/Qualifiers
source                 1..393
                       mol_type = genomic DNA
                       organism = Listeria monocytogenes
SEQUENCE: 231
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                               393

SEQ ID NO: 232         moltype = DNA  length = 393
FEATURE                Location/Qualifiers
source                 1..393
                       mol_type = genomic DNA
                       organism = Listeria monocytogenes
SEQUENCE: 232
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                               393

SEQ ID NO: 233         moltype = DNA  length = 393
FEATURE                Location/Qualifiers
source                 1..393
                       mol_type = genomic DNA
                       organism = Listeria monocytogenes
SEQUENCE: 233
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggcaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                               393

SEQ ID NO: 234         moltype = DNA  length = 393
FEATURE                Location/Qualifiers
source                 1..393
                       mol_type = genomic DNA
                       organism = Listeria monocytogenes
SEQUENCE: 234
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                               393
```

-continued

```
SEQ ID NO: 235         moltype = DNA  length = 393
FEATURE                Location/Qualifiers
source                 1..393
                       mol_type = genomic DNA
                       organism = Listeria monocytogenes
SEQUENCE: 235
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcgcggtggt ggttacactg gtcaagccgg tgctatccgt  240
catggtgtag ctcgtgcact actacaagtg gcacctgagt accgcccagc acttaaatct  300
gctggactac ttactcgtga ttcacgtatg aaagaacgta aaaaaccagg acttaaaggc  360
gcgcgtcgtg cacctcagtt ctcaaaacgt taa                               393

SEQ ID NO: 236         moltype = DNA  length = 393
FEATURE                Location/Qualifiers
source                 1..393
                       mol_type = genomic DNA
                       organism = Listeria monocytogenes
SEQUENCE: 236
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                               393

SEQ ID NO: 237         moltype = DNA  length = 393
FEATURE                Location/Qualifiers
source                 1..393
                       mol_type = genomic DNA
                       organism = Listeria monocytogenes
SEQUENCE: 237
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcgcggtggt ggttacactg gtcaagccgg tgctatccgt  240
catggtgtag ctcgtgcact actacaagtg gcacctgagt accgcccagc acttaaatct  300
gctggtctac ttactcgtga ttcacgtatg aaagaacgta aaaaaccagg acttaaaggc  360
gcgcgtcgtg cacctcagtt ctcaaaacgt taa                               393

SEQ ID NO: 238         moltype = DNA  length = 393
FEATURE                Location/Qualifiers
source                 1..393
                       mol_type = genomic DNA
                       organism = Listeria monocytogenes
SEQUENCE: 238
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                               393

SEQ ID NO: 239         moltype = DNA  length = 393
FEATURE                Location/Qualifiers
source                 1..393
                       mol_type = genomic DNA
                       organism = Listeria monocytogenes
SEQUENCE: 239
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                               393

SEQ ID NO: 240         moltype = DNA  length = 393
FEATURE                Location/Qualifiers
source                 1..393
                       mol_type = genomic DNA
                       organism = Listeria monocytogenes
SEQUENCE: 240
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
```

-continued

```
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                              393

SEQ ID NO: 241         moltype = DNA  length = 312
FEATURE                Location/Qualifiers
source                 1..312
                       mol_type = genomic DNA
                       organism = Listeria innocua
SEQUENCE: 241
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atactaaacc ttccaacatc aacccgcaag gcggaatctt gaatgttgaa  180
gcaccaatcc atgtttcaaa cgtaatgcta attgacccta aaactggcga acctactcgt  240
gtaggctacg aagttaaagg tgataaaaaa gtacgcgtag caaaaaaatc cggtgaagta  300
atagataaat aa                                                     312

SEQ ID NO: 242         moltype = DNA  length = 537
FEATURE                Location/Qualifiers
source                 1..537
                       mol_type = genomic DNA
                       organism = Listeria innocua
SEQUENCE: 242
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaagga  300
gacaaacttg ttcttaacgt agggtactct catccagtag agtttgttgc tcctaaaggc  360
gtagaaattg aagttcctgc aaacactcaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 243         moltype = DNA  length = 360
FEATURE                Location/Qualifiers
source                 1..360
                       mol_type = genomic DNA
                       organism = Listeria innocua
SEQUENCE: 243
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaag ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 244         moltype = DNA  length = 441
FEATURE                Location/Qualifiers
source                 1..441
                       mol_type = genomic DNA
                       organism = Listeria innocua
SEQUENCE: 244
atgaaactac atgaacttaa accttcagaa ggttctcgta aagaacgtaa tcgtgttggt  60
cgtggaacag gctctggtaa cggcaaaact tctggacgcg gtcataaagg acaaaaagct  120
cgttccggtg gtggcgtacg cctaggtttt gaaggtggac aacttccact tttccgtcgt  180
attccaaaac gtggattcac aaatatcaac cgtaaagaat ttgctatcgt taacttagat  240
gttttaaacc gctttgaaga tggtacagaa gtaacaccag aactttaat cgaaactgga  300
attattcgta acgaaaaatc cgggattaaa attttatctg atggaaatat cgagaaaaaa  360
cttactgtga aagcgaacaa attctctgca gctgccaaag aagctattga agcagccggc  420
ggaaaaactg aggtgatcta a                                           441

SEQ ID NO: 245         moltype = DNA  length = 390
FEATURE                Location/Qualifiers
source                 1..390
                       mol_type = genomic DNA
                       organism = Listeria innocua
SEQUENCE: 245
atggctcgta aacaaatac tcgtaaacgt cgtgtgaaaa agaatatcga atctggtatt  60
gcacacattc gttctacatt taataatacg atcgtaatga ttactgacac acatggtaat  120
gctttagctt ggtcaagtgc aggttctcta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                  390

SEQ ID NO: 246         moltype = DNA  length = 393
FEATURE                Location/Qualifiers
source                 1..393
```

```
                         mol_type = genomic DNA
                         organism = Listeria innocua
SEQUENCE: 246
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gcccctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                               393

SEQ ID NO: 247           moltype = DNA  length = 246
FEATURE                  Location/Qualifiers
source                   1..246
                         mol_type = genomic DNA
                         organism = Listeria innocua
SEQUENCE: 247
atgaaaactg gaattcatcc tgagtaccgt ccagtggtat ttgttgatac tagtactgat  60
ttcaaatttt tgtcaggttc tactaagagc tcaagcgaaa caattaaatg ggaagatggc  120
aacgagtatc cattacttcg tgtcgaaatc tcttctgatt cgcacccgtt ctatactggt  180
aaacaaaaac atgcgactgc agacggccgt gtggaccgct tcaacaaaaa atacggtctc  240
aaataa                                                             246

SEQ ID NO: 248           moltype = DNA  length = 273
FEATURE                  Location/Qualifiers
source                   1..273
                         mol_type = genomic DNA
                         organism = Listeria innocua
SEQUENCE: 248
atggcagtta aaattcgttt aaaacgtatg ggttctaaaa agaaaccttt ctaccgtatt  60
gtagtcgctg attctcgttt cccacgtgat ggccgttcaa tcgaaactat tggtacttat  120
aatccattac ttgatccggt tgaagtgaaa atcgacgaag aagcaacttt gaaatggatg  180
cataatggtg cgaaaccatc tgatacagtt cgcaatcttc ttagccgcga aggtatcatg  240
gaaaaattcc ataaccaaaa attaggtaaa taa                               273

SEQ ID NO: 249           moltype = DNA  length = 312
FEATURE                  Location/Qualifiers
source                   1..312
                         mol_type = genomic DNA
                         organism = Listeria innocua
SEQUENCE: 249
atgcatgtca aaaaaggtga taaagtaaaa gttattactg gtaaagataa aggcaaatcc  60
ggcaaagtgc tcgcagcatt tccgaaaaag gaccgcgtac ttatcgaagg aatcaatatg  120
gttaaaaaac atactaaacc ttccaacatc aacccgcaag gcggaatctt gaatgttgaa  180
gcaccaatcc atgtttcaaa cgtaatgcta attgacccta aaactggcga acctactcgt  240
gtaggatacg aagttaaagg tgataaaaaa gtacgcgtag caaaaaaatc cggtgaagta  300
atagataaat aa                                                      312

SEQ ID NO: 250           moltype = DNA  length = 537
FEATURE                  Location/Qualifiers
source                   1..537
                         mol_type = genomic DNA
                         organism = Listeria innocua
SEQUENCE: 250
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgtgcac ttcatggtac aactcgtgct attcttaata acatggttgt cggagtttcc  240
gagggttatg aaaagaaatt agaacttatc ggtgttggtt accgtgcgca aaaacaagga  300
gacaaacttg ttcttaacgt agggtactct catccagtag agtttgttgc tcctaaaggc  360
gtagaaattg aagttcctgc aaacactcaa gtgattgtta aaggatacaa caaagaacac  420
gttggcgagt tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 251           moltype = DNA  length = 360
FEATURE                  Location/Qualifiers
source                   1..360
                         mol_type = genomic DNA
                         organism = Listeria innocua
SEQUENCE: 251
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atccaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 252           moltype = DNA  length = 441
FEATURE                  Location/Qualifiers
```

```
source                1..441
                      mol_type = genomic DNA
                      organism = Listeria innocua
SEQUENCE: 252
atgaaactac atgaacttaa accttcagaa ggttctcgta aagaacgcaa tcgtgttggt  60
cgtggaacag gctctggtaa cggcaaaact tctggacgcg gtcataaagg acaaaaagct  120
cgttccggtg gtggcgtacg cctaggtttt gaaggtggac aacttccact tttccgtcgt  180
attccaaaac gtggattcac aaatatcaac cgtaaagaat ttgctatcgt aaacttagat  240
gttttaaacc gctttgaaga tggtacagaa gtaacaccag aacttttaat cgaaactgga  300
attattcgta acgaaaaatc cgggattaag attttatctg atggaaatat cgagaaaaaa  360
cttactgtga aagcgaacaa attctctgca gctgcaaaag aagctattga agcagctggc  420
ggaaaaactg aggtgatcta a                                            441

SEQ ID NO: 253        moltype = DNA  length = 390
FEATURE               Location/Qualifiers
source                1..390
                      mol_type = genomic DNA
                      organism = Listeria innocua
SEQUENCE: 253
atggctcgta aaacaaatac tcgtaaacgt cgtgtgaaaa agaatatcga atcaggtatt  60
gcacacattc gttctacatt taataatacg atcgtaatga ttactgacac acatggtaat  120
gctttagctt ggtcaagtgc aggttctcta ggatttaaag gttctcgtaa atctactcct  180
ttcgcagcgc aaatggcagc tgaaagtgca gcaaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 254        moltype = DNA  length = 393
FEATURE               Location/Qualifiers
source                1..393
                      mol_type = genomic DNA
                      organism = Listeria innocua
SEQUENCE: 254
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga cccacgtatg aaagaacgta aaaaatacgg acttaaaggc  360
gcgcgtcgtg cacctcagtt ctcaaaacgt taa                              393

SEQ ID NO: 255        moltype = DNA  length = 246
FEATURE               Location/Qualifiers
source                1..246
                      mol_type = genomic DNA
                      organism = Listeria innocua
SEQUENCE: 255
atgaaaactg gaattcatcc tgagtaccgt ccagtggtat ttgttgatac tagtactgat  60
ttcaaatttt tgtcaggttc tactaagagc tcaagcgaaa caattaaatg ggaagatggc  120
aacgagtatc cattacttcg tgtcgaaatc tcttctgatt cgcacccgtt ctatactggt  180
aaacaaaaac atgcgactgc agacggccgt gtggaccgct tcaacaaaaa atatggtctc  240
aaataa                                                             246

SEQ ID NO: 256        moltype = DNA  length = 273
FEATURE               Location/Qualifiers
source                1..273
                      mol_type = genomic DNA
                      organism = Listeria innocua
SEQUENCE: 256
atggcagtta aaattcgttt aaaacgtatg ggttctaaaa agaaaccttt ctaccgtatt  60
gtagtcgctg attctcgttt cccacgtgat ggccgttcaa tcgaaactat tggtacttat  120
aatccattac ttgatccggt tgaagtgaaa atcgacgaag aagcaacttt gaaatggatg  180
cataatggtg cgaaaccatc tgatacagtt cgcaatcttc ttagccgcga aggtatcatg  240
gaaaaattcc ataaccaaaa attaggtaaa taa                              273

SEQ ID NO: 257        moltype = DNA  length = 312
FEATURE               Location/Qualifiers
source                1..312
                      mol_type = genomic DNA
                      organism = Listeria ivanovii
SEQUENCE: 257
atgcatgtca aaaaaggtga taaagtaaaa gttattactg gtaaagataa aggcaaatcc  60
ggcaaagtgc tcgcagcatt tccgaaaaag gaccgcgtac ttattgaagg aattaatatg  120
gttaaaaaac atacaaaacc ttccaacatc aacccgcaag gcggaatctt gaatgttgaa  180
gcaccaatcc atgtttcaaa cgtaatgcta attgacccta aaacaggcga acctactcgt  240
gtaggctacg aagttaaagg cgataagaaa gtacgcgtag caaaaaaatc cggtgaagta  300
atagataaat aa                                                      312
```

```
SEQ ID NO: 258          moltype = DNA  length = 537
FEATURE                 Location/Qualifiers
source                  1..537
                        mol_type = genomic DNA
                        organism = Listeria ivanovii
SEQUENCE: 258
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatca atattgaagg caacgaaatt aacgtttctc gcccgactga taataaaaac  180
caccgcgcgc ttcatggtac aacccgtgct attttaaata acatggttgt cggagtttcc  240
gagggttatg aaaagaaatt agaacttatc ggtgttggtt accgtgcaca aaaacaaggc  300
gacaagcttg ttcttaacgt agggtactct catccagtag aatttgttgc tccgaaaggc  360
gtagaaattg aagttcctgc aaacacacaa gtgattgtta aaggatacaa caaagaacac  420
gttggagaat tagctgcaaa cattcgtgcc gtacgtccac cagagccata taaaggtaaa  480
ggtattcgtt acgaaggcga acatgtacgc cgtaaagaag gtaaaactgg taaataa     537

SEQ ID NO: 259          moltype = DNA  length = 360
FEATURE                 Location/Qualifiers
source                  1..360
                        mol_type = genomic DNA
                        organism = Listeria ivanovii
SEQUENCE: 259
gtgattacca aaatcgacaa aaataaagta cgtaaaaaaa gacatgctcg tgttcgttct  60
aagatttctg gaactgaaag tcgtccacgt ttaaacgtat tccgttcaaa caaaaacatt  120
tatgctcaaa ttattgatga tgtaaatggt gtgacacttg caagtgcgtc taatttagat  180
aaagatttcg gttctgctga atcaaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 260          moltype = DNA  length = 441
FEATURE                 Location/Qualifiers
source                  1..441
                        mol_type = genomic DNA
                        organism = Listeria ivanovii
SEQUENCE: 260
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttctggtg gtggcgtacg tttaggcttt gaaggtggac aacttccact tttccgtcgt  180
attccaaaac gtggattcac aaatatcaac cgtaaagaat ttgcaatcgt gaacttagat  240
gttttaaacc gctttgaaga tggtacagaa gtaacaccag aacttttaat tgaaactgga  300
ataattcgta acgaaaaatc tggaatcaag attttatcag atggtaaaat cgagaaaaaa  360
cttactgtga aagcgaacaa attctctgca gctgctaaag aagcaattga agcggctggc  420
ggaaaaactg aggtgatcta a                                            441

SEQ ID NO: 261          moltype = DNA  length = 390
FEATURE                 Location/Qualifiers
source                  1..390
                        mol_type = genomic DNA
                        organism = Listeria ivanovii
SEQUENCE: 261
atggctcgta aaacaaatac tcgtaaacgc cgtgtgaaaa agaatatcga atctggtatt  60
gcacacattc gttctacatt taataatacg atcgtaatga ttactgacac acatggtaat  120
gctttagctt ggtcaagtgc aggttctcta gggtttaaag gttctcgtaa atctactcct  180
ttcgcagcgc aaatggcagc tgaaagtgca gctaaatcag cacaagaaca tggtttaaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                   390

SEQ ID NO: 262          moltype = DNA  length = 393
FEATURE                 Location/Qualifiers
source                  1..393
                        mol_type = genomic DNA
                        organism = Listeria ivanovii
SEQUENCE: 262
gtggctcaag tacaatatta cggaactggt cgtcgtaaaa gctctgtagc tcgcgtacgt  60
ttagtaccag gcgacggcaa aatcgttatt aacaatagag actgggaaga ttacattcca  120
tttgcagctc ttcgtgaagt tatcaaacaa cctttagtag ctacagaaac tttaggtaat  180
tatgatgtac tagtaaacgt tcacggtggt ggttacactg gtcaagccgg tgctatccgt  240
catggtgtag ctcgtgcact attacaagtg gcacctgagt accgcccagc acttaaatcc  300
gctggtctac ttactcgtga ccctcgtatg aaagaacgta aaaaatacgg acttaaaggc  360
gcgcgtcgtg cacctcagtt ctcaaaacgt taa                               393

SEQ ID NO: 263          moltype = DNA  length = 246
FEATURE                 Location/Qualifiers
source                  1..246
                        mol_type = genomic DNA
                        organism = Listeria ivanovii
```

SEQUENCE: 263
atgaaaactg gaattcatcc tgagtaccgt caagtggtat ttgttgatac tagtactgat 60
ttcaaatttt tgtcaggttc tactaagagc tcaagcgaaa caattaaatg ggaagatggc 120
aacgagtatc cgttacttcg tgtcgaaatc tcttctgatt cgcatccgtt ctatactggt 180
aaacaaaaac atgctacagc agacggacgt gtggaccgct tcaacaaaaa atacggtctc 240
aaataa 246

SEQ ID NO: 264 moltype = DNA length = 273
FEATURE Location/Qualifiers
source 1..273
mol_type = genomic DNA
organism = Listeria ivanovii
SEQUENCE: 264
atggcagtta aaattcgttt aaaacgtatt ggttctaaaa agaaaccttt ctaccgtatt 60
gtagtagctg attctcgttt cccacgtgac ggccgttcaa tcgaaactat tggtacttat 120
aatccattac ttgatccggt tgaagtgaaa attgacgaag aagcaacttt gaaatggatg 180
cataatggtg cgaaaccatc tgatacagtt cgcaatcttc ttagccgcga aggtatcatg 240
gaaaaattcc ataaccaaaa attaggtaaa taa 273

SEQ ID NO: 265 moltype = DNA length = 312
FEATURE Location/Qualifiers
source 1..312
mol_type = genomic DNA
organism = Listeria ivanovii
SEQUENCE: 265
atgcatgtca aaaaaggtga taaagtaaaa gttattactg gtaaagataa aggtaaatcc 60
ggcaaagtgc tcgcagcatt tccgaaaaag gaccgcgtac ttattgaagg aattaatatg 120
gttaaaaaac atacaaaacc ttccaacatc aacccgcaag gcggaatctt gaatgttgaa 180
gcacccatcc atgtttcaaa cgtaatgcta attgacccta aaacaggcga acctactcgt 240
gtaggctacg aagttaaagg cgataaaaaa gtacgcgtag caaaaaaatc cggtgaagta 300
atagataaat aa 312

SEQ ID NO: 266 moltype = DNA length = 537
FEATURE Location/Qualifiers
source 1..537
mol_type = genomic DNA
organism = Listeria ivanovii
SEQUENCE: 266
atgtcccgta taggtaaaaa aactattgtg attcctgcag gtgtaacagt tacacttaat 60
ggatcaacag caacagttaa aggtcctaaa ggtgaacttg taaaagagtt caacccagaa 120
attactatta atattgaagg caacgaaatt aacgtttctc gcccgactga taataagaac 180
caccgtgcgc ttcatggtac aactcgtgct attttaaata acatggttgt cggagtttcc 240
gagggttatg aaaagaaatt agaacttatc ggtgttggtt accgtgcgca aaaacaaggc 300
gacaagcttg ttcttaacgt agggtactct catccagtag aatttgttgc tccgaaaggc 360
gtagaaattg aagttcctgc aaacacacaa gtgattgtta aaggatacaa caaagaacac 420
gttggagaat tagctgcaaa cattcgtgcc gtacgtccac cagaaccata taaaggtaaa 480
ggtattcgtt acgaaggcga acatgtacgc cgtaaagaag gtaaaactgg taaataa 537

SEQ ID NO: 267 moltype = DNA length = 360
FEATURE Location/Qualifiers
source 1..360
mol_type = genomic DNA
organism = Listeria ivanovii
SEQUENCE: 267
gtgattacca aaatcgacaa aaataaagta cgtaaaaaaa gacatgctcg tgttcgttct 60
aagatttccg gaactgaaag tcgtccacgt ttaaacgtat tccgttcaaa caaaaacatt 120
tatgctcaag taattgatga tgtaaatggt gtgacacttg caagtgcgtc taatttagat 180
aaagatttcg gttctgctga atcaaaagtt gatgcagcaa gcaaagttgg cgaactagtt 240
gctaaacgtg cttccgaaaa aggtattact tctgtcactt ttgaccgtgg aggatactta 300
tatcatggcc gcgtaaaagc tcttgctgaa gcagctcgcg aaaatggact agaattttaa 360

SEQ ID NO: 268 moltype = DNA length = 441
FEATURE Location/Qualifiers
source 1..441
mol_type = genomic DNA
organism = Listeria ivanovii
SEQUENCE: 268
atgaaactac atgaacttaa accttcagaa ggttctcgta aggaacgtaa tcgtgttggt 60
cgtggaacag gctctggtaa cggcaaaact tcaggacgcg gtcataaagg acaaaaagct 120
cgttctggtg gtggcgtacg tctaggcttt gaaggtggac aacttccact tttccgtcgt 180
attccaaaac gtggattcac aaatatcaac cgtaaagaat ttgcaatcgt gaacttagat 240
gttttaaacc gctttgaaga tggtacagaa gtaacaccag aacttttaat tgaaactggt 300
attattcgta acgaaaaatc cggaatcaag attttatcaa atggtaaaat cgagaaaaaa 360
cttactgtga aagcgaacaa attctctgca gctgctaaag atgcaattga agcggctggc 420
ggaaaaactg aggtgatcta a 441

SEQ ID NO: 269 moltype = DNA length = 390
FEATURE Location/Qualifiers
source 1..390

```
                         mol_type = genomic DNA
                         organism = Listeria ivanovii
SEQUENCE: 269
atggctcgta aaacaaatac tcgtaaacgc cgtgtgaaaa agaatatcga atctggtatt  60
gcacacattc gttctacatt taataatacg atcgtaatga ttactgacac acatggtaat  120
gctttagctt ggtcaagtgc aggttctcta ggatttaaag gttctcgtaa atctactcct  180
ttcgcagcgc aaatggcagc tgaaagtgca gctaaatcag cacaagaaca tggtttgaaa  240
acattagaag taactgttaa aggtcctggt tcaggtcgtg aagcggctat ccgtgcacta  300
caagcagctg gtcttgaagt aacagctatt aaagatgtaa ctccagttcc acataacgga  360
tgtcgtcctc caaaacgtcg tcgcgtataa                                  390

SEQ ID NO: 270           moltype = DNA  length = 393
FEATURE                  Location/Qualifiers
source                   1..393
                         mol_type = genomic DNA
                         organism = Listeria ivanovii
SEQUENCE: 270
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagctgg tgctatccgt  240
catggtgtag ctcgtgcact attacaagtg gcacctgagt accgcccagc acttaaatct  300
gctggtctac ttactcgtga ccctcgtatg aaagaacgta agaaatacgg acttaaaggc  360
gcgcgtcgtg cacctcagtt ctcaaaacgt taa                               393

SEQ ID NO: 271           moltype = DNA  length = 246
FEATURE                  Location/Qualifiers
source                   1..246
                         mol_type = genomic DNA
                         organism = Listeria ivanovii
SEQUENCE: 271
atgaaaactg gaattcatcc tgagtaccgt caagtggtat ttgttgatac tagtactgat  60
ttcaaatttt tgtcaggttc tactaagagc tcaagcgaaa caattaaatg ggaagatggc  120
aacgagtatc cgttacttcg tgtcgaaatc tcttctgatt cgcatccgtt ctatactggt  180
aaacaaaaac atgctacagc agacggacgt gtggaccgct tcaacaaaaa atacggtctc  240
aaataa                                                             246

SEQ ID NO: 272           moltype = DNA  length = 273
FEATURE                  Location/Qualifiers
source                   1..273
                         mol_type = genomic DNA
                         organism = Listeria ivanovii
SEQUENCE: 272
atggcagtta aaattcgttt aaaacgtatt ggttctaaaa agaaaccttt ctaccgtatt  60
gtagtagctg attctcgttt cccacgtgac ggccgttcaa tcgaaactat tggtacttat  120
aatccattac ttgatccggt tgaagtgaaa attgacgaag aagcaacttt gaaatggatg  180
cataatggtg cgaaaccatc tgatacagtt cgcaatcttc ttagccgcga aggtatcatg  240
gaaaaattcc ataaccaaaa attaggtaaa taa                               273

SEQ ID NO: 273           moltype = DNA  length = 312
FEATURE                  Location/Qualifiers
source                   1..312
                         mol_type = genomic DNA
                         organism = Listeria seeligeri
SEQUENCE: 273
atgcatgtca aaaaaggtga taaagtaaaa gttattactg gtaaagataa aggcaaatcc  60
ggcaaagtgc tcgcagcatt tccgaagaag gatcgcgtac ttattgaagg aattaatatg  120
gtcaaaaaac atacaaaacc ttccaacatc aacccgcaag gcggaatctt gaatgttgaa  180
gcaccaatcc atgtttcaaa cgtgatgcta attgacccta aaacaggcga acctactcgt  240
gtaggctacg aagttaaagg cgataaaaaa gtacgcgtag caaaaaaatc cggtgaagta  300
atagataaat aa                                                      312

SEQ ID NO: 274           moltype = DNA  length = 537
FEATURE                  Location/Qualifiers
source                   1..537
                         mol_type = genomic DNA
                         organism = Listeria seeligeri
SEQUENCE: 274
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaagg caacgaaatt aacgtttctc gcccgactga taataaaaac  180
caccgcgcgc ttcatggtac aactcgtgct attctaaata acatggttgt cggagtttcc  240
gagggttatg aaaagaaatt agaacttatc ggtgttggtt accgtgcgca aaaacaaggc  300
gacaagcttg ttcttaacgt agggtactct catccagtag aatttgttgc tccgaaaggc  360
gtagaaattg aagttcctgc aaacacacaa gtgattgtta aaggatacaa caaagaacac  420
gttggagaat tagctgcaaa cattcgtgcc gtacgtccac cagagccgta taaaggtaaa  480
ggtattcgtt acgaaggcga acatgtacgc cgtaaagaag gtaaaactgg taaataa     537
```

```
SEQ ID NO: 275         moltype = DNA  length = 360
FEATURE                Location/Qualifiers
source                 1..360
                       mol_type = genomic DNA
                       organism = Listeria seeligeri
SEQUENCE: 275
gtgattacca aaatcgacaa aaataaagta cgtaaaaaaa gacatgctcg tgttcgttct  60
aagatttccg gaactgaaag tcgtccacgt ttaaacgtat tccgttcaaa caaaaacatt  120
tatgctcaag taattgatga tgtaaatggt gtgacacttg caagtgcgtc taatttagat  180
aaagatttcg gttctgttga atcaaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 276         moltype = DNA  length = 441
FEATURE                Location/Qualifiers
source                 1..441
                       mol_type = genomic DNA
                       organism = Listeria seeligeri
SEQUENCE: 276
atgaaactac atgaacttaa gccttcagaa ggttctcgaa aagaacgtaa tcgtgttggt  60
cgtggaacag gctctggtaa cggcaaaact tcaggacgcg gtcataaagg acaaaaagct  120
cgttccggtg gtggcgtacg tttaggtttt gaaggtggac aacttccact tttccgtcgt  180
attccaaaac gtggattcac aaatatcaat cgtaaagaat ttgcaatcgt gaacttagat  240
gttttaaacc gctttgaaga cggtacagaa gtaacaccag aacttttaat tgaatctgga  300
attattcgta acgaaaaatc cggaatcaag attttatctg atggtaaaat cgagaaaaaa  360
cttactgtga aagcgaacaa attctctgca gctgcaaaag aagctattga agcggctggc  420
ggaaaaactg aggtgatcta a                                            441

SEQ ID NO: 277         moltype = DNA  length = 390
FEATURE                Location/Qualifiers
source                 1..390
                       mol_type = genomic DNA
                       organism = Listeria seeligeri
SEQUENCE: 277
atggctcgta aaacaaatac tcgtaaacgc cgtgtgaaaa agaatatcga atctggtatt  60
gcacacattc gttctacatt taataatacg atcgtaatga ttactgacac acagggtaat  120
gctttagctt ggtcaagtgc aggttctcta ggatttaaag gttctcgtaa atctactcct  180
ttcgcagcgc aaatggcagc tgaaagtgca gctaagtcag cacaagaaca tggtttgaaa  240
acattagaag taacggttaa aggtcctggt tcaggtcgtg aagcggctat ccgtgcacta  300
caagcagctg gtcttgaagt aacagctatt agagatgtaa ctccagttcc acataacgga  360
tgtcgtcctc caaaacgtcg tcgcgtataa                                   390

SEQ ID NO: 278         moltype = DNA  length = 393
FEATURE                Location/Qualifiers
source                 1..393
                       mol_type = genomic DNA
                       organism = Listeria seeligeri
SEQUENCE: 278
gtggctcaag tacaatatta cggaactggt cgtcgtaaaa gctctgtagc tcgcgtacgt  60
ttagtaccag gcgacggcaa aatcgttatt aacaatagag actgggaaga ttacatccca  120
tttgcagctc ttcgtgaagt tatcaaacaa cctttagtag ctacagaaac tttaggtaac  180
tatgatgtac tagtaaacgt tcacggtggt ggttacactg gtcaagccgg tgctatccgt  240
catggtgtag ctcgtgcact attacaagtg gctcctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                               393

SEQ ID NO: 279         moltype = DNA  length = 246
FEATURE                Location/Qualifiers
source                 1..246
                       mol_type = genomic DNA
                       organism = Listeria seeligeri
SEQUENCE: 279
atgaaaactg gaattcatcc tgagtaccgt caagtggtat ttgttgatac tagtactgat  60
ttcaaatttt tgtcaggttc tactaagagc tcaagcgaaa caattaaatg ggaagatggc  120
aacgagtatc cgttacttcg tgtcgaaatc tcttctgatt cgcatccgtt ctatactggt  180
aaacaaaaac atgctacagc agacggacgt gtggaccgct tcaacaaaaa atatggtctc  240
aaataa                                                             246

SEQ ID NO: 280         moltype = DNA  length = 273
FEATURE                Location/Qualifiers
source                 1..273
                       mol_type = genomic DNA
                       organism = Listeria seeligeri
SEQUENCE: 280
atggcagtta aaattcgttt aaaacgtatt ggttctaaaa agaaaccttt ctaccgtatt  60
gtagtagctg attctcgttt cccacgtgac ggccgttcaa tcgaaactat tggtacttat  120
aatccattgc ttgatccggt tgaagtgaaa attgacgaag aagcaacttt gaaatggatg  180
```

-continued

```
cataatggtg cgaaaccatc tgatacagtt cgcaatcttc ttagccgcga aggtatcatg  240
gaaaaattcc ataaccaaaa attaggtaaa taa                                273

SEQ ID NO: 281         moltype = DNA  length = 312
FEATURE                Location/Qualifiers
source                 1..312
                       mol_type = genomic DNA
                       organism = Listeria welshimeri
SEQUENCE: 281
atgcatgtca aaaaaggtga taaagtaaaa gttattactg gtaaagataa aggcaaatcc  60
ggcaaagtgc tcgcagcatt tccgaaaaag gatcgcgtac ttattgaagg aattaatatg  120
gtcaaaaaac atacaaaacc ttccaacatc aatccgcaag gcggaatctt gaatgttgaa  180
gcaccaatcc atgtttcaaa cgtaatgcta attgacccta aaacaggcga acctactcgt  240
gtaggctacg aagttaaagg cgataaaaaa gtacgcgtag caaaaaaatc cggtgaagta  300
atagataaat aa                                                       312

SEQ ID NO: 282         moltype = DNA  length = 537
FEATURE                Location/Qualifiers
source                 1..537
                       mol_type = genomic DNA
                       organism = Listeria welshimeri
SEQUENCE: 282
atgtcccgta taggtaaaaa aactattgtg attcctgcag gtgtaacagt tacacttaat  60
ggatcaacag caacagttaa aggtcctaaa ggtgaacttg taaaagagtt caacccagaa  120
attactatta atattgaggg caacgaaatt aacgtttctc gcccgactga taataaaaac  180
caccgcgcgc ttcatggtac aactcgtgct attctaaata acatggttgt cggagtttcc  240
gagggttatg aaaagaaatt agaacttatc ggtgttggtt accgtgcgca aaaacaaggc  300
gacaagcttg ttcttaacgt agggtactct catccagtag aatttgttgc tccgaaaggc  360
gtagaaattg aagttcctgc aaacacacaa gtgattgtta aaggatacaa caaagaacac  420
gttggagaat tagctgcaaa cattcgtgcc gtacgtccgc cagagccgta taaaggtaaa  480
ggtattcgtt acgaaggcga acatgtacgc cgtaaagaag gtaaaactgg taaataa      537

SEQ ID NO: 283         moltype = DNA  length = 360
FEATURE                Location/Qualifiers
source                 1..360
                       mol_type = genomic DNA
                       organism = Listeria welshimeri
SEQUENCE: 283
gtgattacca aaatcgacaa aaataaagta cgtaaaaaaa gacatgctcg tgttcgttct  60
aaaatttccg gaactgaaag tcgtccacgt ttaaacgtat tccgttcaaa caaaaacatt  120
tatgctcaag taattgatga tgtaaatggt gtgacacttg caagtgcgtc taatttagat  180
aaagatttcg gttctgctga atcaaaagtt gatgcagcaa gcaaagttgg cgaactagtt  240
gctaaacgtg cttccgaaaa aggtattact tctgtcactt ttgaccgtgg aggatactta  300
tatcatggcc gcgtaaaagc tcttgctgaa gcagctcgcg aaaatggact agaattttaa  360

SEQ ID NO: 284         moltype = DNA  length = 441
FEATURE                Location/Qualifiers
source                 1..441
                       mol_type = genomic DNA
                       organism = Listeria welshimeri
SEQUENCE: 284
atgaaactac atgaacttaa gccttcagaa ggttctcgta aagaacgtaa tcgtgttggt  60
cgtggaacag gctctggtaa cggcaaaact tcaggacgcg gtcataaagg acaaaaagct  120
cgttccggtg gtggcgtacg tttaggcttt gaaggtggac aacttccact tttccgtcgt  180
attccaaaac gtggattcac aaatatcaac cgtaaagaat ttgcaatcgt gaacttagat  240
gttttaaacc gctttgaaga cggtacagaa gtaacaccag aacttttaat tgaatctgga  300
attattcgta acgaaaaatc cggaatcaag attttatctg atggtaaaat cgagaaaaaa  360
cttactgtga aagcgaacaa attctctgca gctgcaaaag aagctattga agcggctggc  420
ggaaaaactg aggtgatcta a                                             441

SEQ ID NO: 285         moltype = DNA  length = 390
FEATURE                Location/Qualifiers
source                 1..390
                       mol_type = genomic DNA
                       organism = Listeria welshimeri
SEQUENCE: 285
atggctcgta aaacaaatac tcgtaaacgc cgtgtgaaaa agaatatcga atctggtatt  60
gcacacattc gttctacatt taataatacg atcgtaatga ttactgacac acatggtaat  120
gctttagctt ggtcaagtgc aggttctcta ggatttaaag gttctcgtaa atctactcct  180
ttcgcagcgc aaatggcggc tgaaagtgca gctaaatcag cacaagaaca tggtttgaaa  240
acattagaag taactgttaa aggtcctggt tcaggtcgtg aagcggctat ccgtgcacta  300
caagcagctg gtcttgaagt aacagctatt agagatgtaa ctccagttcc acataacgga  360
tgtcgtcctc caaaacgccg tcgcgtataa                                    390

SEQ ID NO: 286         moltype = DNA  length = 393
FEATURE                Location/Qualifiers
source                 1..393
                       mol_type = genomic DNA
                       organism = Listeria welshimeri
```

```
SEQUENCE: 286
gtggctcaag tacaatatta cggaactggt cgtcgtaaaa gctctgtagc tcgcgtacgt  60
ttagtaccag gcgacggcaa aatcgttatt aacaatagag actgggaaga ttatatccca  120
tttgcagctc ttcgtgaagt tatcaaacaa cctttagtag ctacagaaac tttaggtaac  180
tatgatgtac tagtaaacgt tcgcggtggt ggttacactg gtcaagccgg tgctatccgt  240
catggtgtag ctcgtgcact actacaagtg gcacctgagt accgcccagc acttaaatct  300
gctggcctac ttactcgtga ttcacgtatg aaagaacgta aaaaaccagg acttaaaggc  360
gcgcgtcgtg cacctcagtt ctcaaaacgt taa                                393

SEQ ID NO: 287          moltype = DNA  length = 246
FEATURE                 Location/Qualifiers
source                  1..246
                        mol_type = genomic DNA
                        organism = Listeria welshimeri
SEQUENCE: 287
atgaaaactg gaattcatcc tgagtaccgt caagtggtat ttgttgatac tagtactgat  60
ttcaaatttt tgtcaggttc tactaagagc tcaagcgaaa caattaaatg ggaagatggc  120
aacgagtatc cgttacttcg tgtcgaaatc tcttctgatt cgcatccgtt ctatactggt  180
aaacaaaaac atgctacagc agacggacgt gtggaccgct tcaacaaaaa atacggtctc  240
aaataa                                                              246

SEQ ID NO: 288          moltype = DNA  length = 273
FEATURE                 Location/Qualifiers
source                  1..273
                        mol_type = genomic DNA
                        organism = Listeria welshimeri
SEQUENCE: 288
atggcagtta aaattcgttt aaaacgtatt ggttctaaaa agaaaccttt ctaccgtatt  60
gtagtcgctg attctcgttt cccacgtgat ggccgttcaa tcgaaactat tggtacttat  120
aatccattac ttgatccggt tgaagtgaaa atcgacgaag aagcaacttt gaaatggatg  180
cataatggtg caaaaccatc tgatacagtt cgcaatcttc ttagccgcga aggtatcatg  240
gaaaaattcc ataaccaaaa attaggtaaa taa                                273

SEQ ID NO: 289          moltype = DNA  length = 321
FEATURE                 Location/Qualifiers
source                  1..321
                        mol_type = genomic DNA
                        organism = Listeria rocourtiae
SEQUENCE: 289
atgcatgtca aaaaaggtga taaagttcaa gttattactg gtaaagataa aggtaaatcc  60
ggcaaaatca tcgctgcttt tcctaagaaa gaccgcgtga ttgttgaagg acttaacatg  120
gttaaaaaac atacaaaacc atcaaacgtt aacccgcaag gtggaatttt aaatgttgaa  180
gcaccgattc acgtatctaa cgtaatgctt atcgatccta agactggtga accaactcgt  240
gtgaaccgtg aaatcaagga tggtaagaaa gtacgcgtag ctaaaaaatc cggtgaaatt  300
ataaaagacg caactaaata a                                             321

SEQ ID NO: 290          moltype = DNA  length = 537
FEATURE                 Location/Qualifiers
source                  1..537
                        mol_type = genomic DNA
                        organism = Listeria rocourtiae
SEQUENCE: 290
atgtcccgta taggtaaaaa gacaattgtt attccagctg gtgttactgt aacattggat  60
ggttcaacag caactgttaa gggtcctaaa ggtgagcttg taaaaacttt taaccctgat  120
atctcaatca atatcgaagg tagcgagatt aatgtgactc gtccttctga caataaaaca  180
caccgtgctc ttcatggtac aacacgtgct atcttaaata acatggttgt cggcgtatct  240
gaaggttacg aaaaaactct tgagcttatt ggtgtcggtt accgtgctgc aaaacaaggt  300
actacacttg ttttaaacgt tggttactct catccagtag aattcgaagc tcgtccaggc  360
gttgaagtgg aagtaccagc aaacacgaaa gttatcgttc gcggtattaa caaagaacac  420
gttggcgaat tggctgcaaa tatccgttcc gtacgtccgc cagagcctta taaaggtaaa  480
ggtatccgtt acgaaggcga atttgtacgt cgtaaagaag gtaagactgg taaataa     537

SEQ ID NO: 291          moltype = DNA  length = 360
FEATURE                 Location/Qualifiers
source                  1..360
                        mol_type = genomic DNA
                        organism = Listeria rocourtiae
SEQUENCE: 291
gtgattacca aaatcgacaa aaataaagtg cgtaaaaaaa gacatggtcg tgttcgttct  60
aagatttctg gaactgcagc tcgtccacgc ttgaacgtat tccgttcaaa caaaaacatt  120
tatgctcaac ttatcgatga tgttaacggt gtaacaatcg ctagcgcatc taacgtagat  180
aaagatttcc ctaaagcgga gtccaaagtt gacgctgcta caaaagtagg cgaaatcgtt  240
gcaaaacgcg ctgcagaaaa aggtgttaaa gctgttgtat ttgatcgcgg aggttactta  300
taccacggtc gtgtgcaagc tttggctgaa gctgctcgtg aaaatggatt ggaattttaa  360
```

```
SEQ ID NO: 292          moltype = DNA  length = 441
FEATURE                 Location/Qualifiers
source                  1..441
                        mol_type = genomic DNA
                        organism = Listeria rocourtiae
SEQUENCE: 292
atgaaacttc acgaacttaa acctgcagaa ggttctcgta aagagcgtaa tcgtgttggt  60
cgtggtatga gttctggtaa cggtaaaaca tcaggacgcg gtcacaaagg tcaaaaagca  120
cgttcaggtg gcggtgtacg cctaggtttc gaaggtggac aactaccatt gttccgtcgt  180
attccaaaac gtggttttac aaatattaac cgtaaagaat acgctgttgt gaacattgat  240
gttttaaatc gctttgaaga tggtacagaa gtaacacctg aattattaat tgaaacaggt  300
atcgtccgta atgcaaaatc tggaattaag attttgtcta acggcgcaat cgagaaaaaa  360
cttacggtga aagctaacaa attctcatca gctgctaaag aggctatcga ggctgctggt  420
ggacaaactg aggtgatcta a                                            441

SEQ ID NO: 293          moltype = DNA  length = 390
FEATURE                 Location/Qualifiers
source                  1..390
                        mol_type = genomic DNA
                        organism = Listeria rocourtiae
SEQUENCE: 293
atggctcgta aaactaatac tcgtaaacgt cgtgtgaaaa agaatatcga agctggtatt  60
gcacacattc gttctacatt caataataca atcgtaacga ttactgacat gcatggtaac  120
gcagtagcat ggtcaagtgc aggagcttta ggattcaaag gagctcgtaa atcgacacct  180
ttcgcagcgc aattagcggc agaaacgtgt gcaaaagctg cacaagagca tggtttaaaa  240
actttggaag taacagttaa aggaccaggt tcaggacgtg aagcagcaat tcgtgcgctt  300
caagcggcag gtcttgatgt aactgctatt aaagatgtga ctccagttcc tcataacgga  360
tgtcgtcctc caaaacgtcg tcgtgtctaa                                  390

SEQ ID NO: 294          moltype = DNA  length = 393
FEATURE                 Location/Qualifiers
source                  1..393
                        mol_type = genomic DNA
                        organism = Listeria rocourtiae
SEQUENCE: 294
gtggctcaag tacaatatta tggaacaggt cgtcgtaaaa gctcagtagc tcgtgtacgt  60
ttagtaccag gcgatggcaa agtagttatc aacggtagag attgggaaga ttacattcca  120
ttcgcggctc ttcgcgaagt tattaaacaa ccattagttg caactgaaac tctaggaaac  180
tatgatgttt tagtaaacgt aaacggtggt ggttatactg gtcaagctgg agcaatccgt  240
cacggaattt cacgtgcatt gctacaagtt gcaccggatt atcgttctcc attaaaacgt  300
gcaggtctat taactcgtga cccacgtatg aaagaacgta agaaaccagg acttaaaggc  360
gcgcgtcgtg cacctcagtt ctcaaaacgt taa                               393

SEQ ID NO: 295          moltype = DNA  length = 246
FEATURE                 Location/Qualifiers
source                  1..246
                        mol_type = genomic DNA
                        organism = Listeria rocourtiae
SEQUENCE: 295
atgaaagctg gaattcaccc ggaataccgt caagtggtat ttcttgatac tagtacagat  60
ttcaaatttc tttctggttc tactaagggc tcgaacgaaa ctattcaatg ggaagatggc  120
aacgagtatc cattactacg tgtcgaaatc agttctgatt ctcacccatt ctatactggt  180
aaacaaaaac atgcgacagc cgatggacgt gtcgatcgtt tcaacaagaa atacggcatc  240
aaataa                                                             246

SEQ ID NO: 296          moltype = DNA  length = 273
FEATURE                 Location/Qualifiers
source                  1..273
                        mol_type = genomic DNA
                        organism = Listeria rocourtiae
SEQUENCE: 296
atggcagtta aaattcgttt aaaacgtatg ggttctaaca agaaaccttt ctaccgtatt  60
caagttgcag attctcgttc tccacgtgat ggtcgttcaa tcgcaacagt gggtacatac  120
aatccactgt tgaacccagc agaagtgaaa atcgacgaag aagcagtttt aaaatggttg  180
cataatggcg cgaaaccatc tgacacagtt cgtaacttgt tgtcaaatga aggcattatg  240
gaaaaattcc acaattcaaa actaggtaag taa                               273

SEQ ID NO: 297          moltype = DNA  length = 312
FEATURE                 Location/Qualifiers
source                  1..312
                        mol_type = genomic DNA
                        organism = Listeria grayi
SEQUENCE: 297
atgcatatta aaaaaggtga taaagttcaa gttattactg gtaaagataa aggcaaatcc  60
ggtgcagtac tcgctgcatt tccaaagaaa gaccgtgtaa ttgttgaagg aatcaacatg  120
atcaaaaaac atgcgaaacc ttccaacgtg aatccacaag gtggaatctt aaacgttgaa  180
```

-continued

```
gcaccaattc acgtttctaa cgtaatgctt atcgatccta aatctggaga acccacacgc  240
gtgagttacc aagtgaagga tgacaagaaa gtgcgagttg ctaaaaaatc cggtgaagtt  300
ttagataaat aa                                                      312

SEQ ID NO: 298          moltype = DNA  length = 537
FEATURE                 Location/Qualifiers
source                  1..537
                        mol_type = genomic DNA
                        organism = Listeria grayi
SEQUENCE: 298
atgtcccgta ttggtaaaaa gacaattgtc attcctgaag gtgtaacagt tacacttgat  60
ggttcaactg ctacagtaaa aggccctaaa ggtcaacttg taaaagaatt taaccctgac  120
attaaaattg atatcgaagg caatgaaatc aacgtttctc gcccaagtga tcataaaaca  180
catcgttctc ttcacggaac gactcgtgcg atcttaaata acatggtcgt aggtgtttcc  240
gaaggttacg aaaaaacatt agaattgatc ggtgttggtt accgtgctca aaaacaagga  300
aacaaacttg ttcttaacgt aggttactct catccagtag aatttgaagc tccagaaggc  360
gttgaaattg atgttcctgc aaatacgaaa gtaattgtta aaggatacaa caaagaacac  420
gttggagaac tagctgctaa tattcgtgct actcgtcctc ctgaacctta taaaggtaaa  480
gggatccgtt acgaaggcga atatgtacgc cgcaaagaag gtaaaactgg taaataa     537

SEQ ID NO: 299          moltype = DNA  length = 360
FEATURE                 Location/Qualifiers
source                  1..360
                        mol_type = genomic DNA
                        organism = Listeria grayi
SEQUENCE: 299
gtgattacca aaatcgacaa aaataaagtc cgtaaaagaa gacatgcacg tgtccgttct  60
aagattactg gaacagaatc tcgtccacgc ttgaacgtat tccgttctaa caaaaacatt  120
tacgcgcaag ttatcgacga cgtaaatggc gtgacacttg caagtgcatc taatctagat  180
aaagaatttg gctctagcga atcgaaagtt gacgcagcta gcaaagttgg cgcattagtt  240
gcgaaacgtg ctgctgataa aggcattact tctgttactt ttgaccgtgg aggctattta  300
tatcatggcc gagtgaaagc tttggctgaa gctgctcgtg aaaatggttt agaattttaa  360

SEQ ID NO: 300          moltype = DNA  length = 441
FEATURE                 Location/Qualifiers
source                  1..441
                        mol_type = genomic DNA
                        organism = Listeria grayi
SEQUENCE: 300
atgaaactac acgaacttaa accttctgag ggatctcgta aggaacgcaa tcgtgttggt  60
cgtggtacag gctctggtaa cggtaaaact tccggtcgcg gacataaagg gcaaaaagct  120
cgttccggcg gtggtgtacg tttaggcttt gaaggtggac aacttccact tttccgtcgt  180
cttccaaaac gtgggttcac aaatatcaac cgcaaagaat atgcagttgt taatgttggg  240
actttaaacc gttttgaaga tggtacagaa gtaacaccag aattgttaat tgaaactggt  300
gtgatcagca atgcaaaatc tggtatcaaa gtattatcag aaggaaaaat tgagaagaaa  360
ttaactgtta aggctaacaa attctcagca gcggctaaag aagcaatcga agctgctggt  420
ggacaaactg aggtgatcta a                                            441

SEQ ID NO: 301          moltype = DNA  length = 390
FEATURE                 Location/Qualifiers
source                  1..390
                        mol_type = genomic DNA
                        organism = Listeria grayi
SEQUENCE: 301
atggctcgta aaacgaatac tcgtaaacgt cgtgtgaaaa agaatatcga agcaggtatt  60
gctcacatcc gttctacatt taacaatacg atcgtaatga tcactgatgt acatggtaat  120
gctttggcat ggtctagtgc aggtgcttta ggatttaaag gttctaaaaa atctactcct  180
ttcgcagctc aaatggcagc tgaaagtgca gctaaatcag ctcaagaaca tggcattaaa  240
actcttgaag taacagtaaa aggtcctggt gcaggtcgcg aggctgctat ccgtgcgctt  300
caagctgcag gtatcgaagt tactgctatt aaagatgtaa ctcctgttcc tcacaatggt  360
tgtcgccctc caaaacgtcg tcgtgtataa                                   390

SEQ ID NO: 302          moltype = DNA  length = 393
FEATURE                 Location/Qualifiers
source                  1..393
                        mol_type = genomic DNA
                        organism = Listeria grayi
SEQUENCE: 302
gtggctcaag tacaatatta cggaacaggt cgtcgtaaaa gctcagtagc tcgtgtacgt  60
ctagtaccag gcgacggcaa agttgttatc aataatagag actgggaaga ttacatccca  120
ttcgcagcac tacgcgaagt aatcaaacaa cctttagtag caacagatgc tttaggaaaa  180
tatgacgtat tagtaaacgt tcatggtgga ggctacactg gtcaagccgg tgctatccgt  240
cacggcgtgg cacgtgcact attacttgta tcacctgagt accgcccagc acttaaatct  300
gctggattgc taactcgtga ccctcgtatg aaagaacgta aaaaatacgg tcttaaagcg  360
gctcgtcgcg cacctcagtt ctcaaaacgt taa                              393
```

```
SEQ ID NO: 303          moltype = DNA  length = 246
FEATURE                 Location/Qualifiers
source                  1..246
                        mol_type = genomic DNA
                        organism = Listeria grayi
SEQUENCE: 303
atgaaaaaag aaattcatcc gaattatcga ccagttgtat ttgtagatac tactacagat  60
tttaaattct tgtctggttc tacaaaaaac tccagtgaaa caattacatg ggaagacgga  120
aacgaatatc cacttcttcg tgtggaaatt tcttctgact ctcatccatt ctacactggt  180
aaacaaaaac atgctgccgc tgatggacgt gttgaccgct tcaacaaaaa atacggcatc  240
aaataa                                                             246

SEQ ID NO: 304          moltype = DNA  length = 273
FEATURE                 Location/Qualifiers
source                  1..273
                        mol_type = genomic DNA
                        organism = Listeria grayi
SEQUENCE: 304
atggcagtta aaattcgttt aaaacgtatg ggttctaaaa agaaaccttt ttatcgtatc  60
gttgtagctg actctcgcta tccacgtgat ggccgttcga tcgaaactgt tggaacatac  120
aacccgttgt taaatccagc agaagtgaaa atcaatgaag agtctgtttt gaaatggatg  180
cataatggtg cgaaaccatc tgatacagtt cgtaacttat tcagtaacga aggtatcatg  240
gaaaaattcc acaaccaaaa attaggtaaa taa                              273

SEQ ID NO: 305          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 305
catggcggat gttcaggtaa                                              20

SEQ ID NO: 306          moltype = DNA  length = 20
FEATURE                 Location/Qualifiers
misc_feature            1..20
                        note = PCR prime
source                  1..20
                        mol_type = other DNA
                        organism = synthetic construct
SEQUENCE: 306
ctccttccag aataacgggt                                              20

SEQ ID NO: 307          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 307
agcagcacaa aacgtggtac                                              20

SEQ ID NO: 308          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 308
aaggaggact aacgaatgcc                                              20

SEQ ID NO: 309          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 309
tgcacgcaac ttacaaggca                                              20

SEQ ID NO: 310          moltype = DNA  length = 20
FEATURE                 Location/Qualifiers
misc_feature            1..20
                        note = PCR primer
```

```
source                  1..20
                        mol_type = other DNA
                        organism = synthetic construct
SEQUENCE: 310
cggacgcaat aaccaaggta                                                   20

SEQ ID NO: 311          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 311
aatgaacccg aacgatcacc                                                   20

SEQ ID NO: 312          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 312
tacaagcgca aaagccgttg                                                   20

SEQ ID NO: 313          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 313
gtgcagctaa ccgtgtgaat                                                   20

SEQ ID NO: 314          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 314
aggcggaact gaagttgcat                                                   20

SEQ ID NO: 315          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 315
acccgttatt ctggaaggag                                                   20

SEQ ID NO: 316          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 316
aaggcattac acccatggca                                                   20

SEQ ID NO: 317          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 317
ctcgtccatt gtctgcaact                                                   20
```

```
SEQ ID NO: 318          moltype = DNA  length = 22
FEATURE                 Location/Qualifiers
misc_feature            1..22
                        note = PCR primer
source                  1..22
                        mol_type = other DNA
                        organism = synthetic construct
SEQUENCE: 318
caaacgtaat gctamttgac cc                                          22

SEQ ID NO: 319          moltype = DNA  length = 21
FEATURE                 Location/Qualifiers
misc_feature            1..21
                        note = PCR primer
source                  1..21
                        mol_type = other DNA
                        organism = synthetic construct
SEQUENCE: 319
cgtggtaact atacgttggg t                                           21

SEQ ID NO: 320          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 320
gactggcgaa cgtgtaatca                                             20

SEQ ID NO: 321          moltype = DNA  length = 22
FEATURE                 Location/Qualifiers
misc_feature            1..22
                        note = PCR primer
source                  1..22
                        mol_type = other DNA
                        organism = synthetic construct
SEQUENCE: 321
tcctgcaaac acwcaagtga tt                                          22

SEQ ID NO: 322          moltype = DNA  length = 22
FEATURE                 Location/Qualifiers
misc_feature            1..22
                        note = PCR primer
source                  1..22
                        mol_type = other DNA
                        organism = synthetic construct
SEQUENCE: 322
ggagggacat attacatgcc tg                                          22

SEQ ID NO: 323          moltype = DNA  length = 18
FEATURE                 Location/Qualifiers
misc_feature            1..18
                        note = PCR primer
source                  1..18
                        mol_type = other DNA
                        organism = synthetic construct
SEQUENCE: 323
ttaatcggac gccctcaa                                               18

SEQ ID NO: 324          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 324
ctctaccaaa cgcgatgttc                                             20

SEQ ID NO: 325          moltype = DNA  length = 22
FEATURE                 Location/Qualifiers
misc_feature            1..22
                        note = PCR primer
source                  1..22
                        mol_type = other DNA
                        organism = synthetic construct
```

```
SEQUENCE: 325
ggaaacacag agctagacaa gg                                              22

SEQ ID NO: 326          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 326
cctgacacgc ggaagaatta                                                 20

SEQ ID NO: 327          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 327
aaggcccgtc caaaacagta                                                 20

SEQ ID NO: 328          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 328
cagcgatgat gccaagtatg                                                 20

SEQ ID NO: 329          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 329
gaagcagttt cacttggagc                                                 20

SEQ ID NO: 330          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 330
aactggctga ccttggctta                                                 20

SEQ ID NO: 331          moltype = DNA  length = 20
FEATURE                 Location/Qualifiers
misc_feature            1..20
                        note = PCR primer
source                  1..20
                        mol_type = other DNA
                        organism = synthetic construct
SEQUENCE: 331
cccctgtgat ggcgagtctt                                                 20

SEQ ID NO: 332          moltype = DNA  length = 25
FEATURE                 Location/Qualifiers
misc_feature            1..25
                        note = PCR primer
source                  1..25
                        mol_type = other DNA
                        organism = synthetic construct
SEQUENCE: 332
tcttctcgca taacatcgac ttgaa                                           25

SEQ ID NO: 333          moltype = DNA  length = 24
FEATURE                 Location/Qualifiers
misc_feature            1..24
                        note = PCR primer
```

```
source                 1..24
                       mol_type = other DNA
                       organism = synthetic construct
SEQUENCE: 333
tgaaggattt aagtgagtgc atgt                                        24

SEQ ID NO: 334         moltype = DNA  length = 21
FEATURE                Location/Qualifiers
misc_feature           1..21
                       note = PCR primer
source                 1..21
                       mol_type = other DNA
                       organism = synthetic construct
SEQUENCE: 334
cgcatcgctt gtttcatatc t                                           21

SEQ ID NO: 335         moltype = DNA  length = 22
FEATURE                Location/Qualifiers
misc_feature           1..22
                       note = PCR primer
source                 1..22
                       mol_type = other DNA
                       organism = synthetic construct
SEQUENCE: 335
ttcgggagct aatttgtttc aa                                          22

SEQ ID NO: 336         moltype = DNA  length = 22
FEATURE                Location/Qualifiers
misc_feature           1..22
                       note = PCR primer
source                 1..22
                       mol_type = other DNA
                       organism = synthetic construct
SEQUENCE: 336
aacgttttca gaactgaggt gc                                          22

SEQ ID NO: 337         moltype = DNA  length = 24
FEATURE                Location/Qualifiers
misc_feature           1..24
                       note = PCR primer
source                 1..24
                       mol_type = other DNA
                       organism = synthetic construct
SEQUENCE: 337
cacatatcga cactggagac tttg                                        24

SEQ ID NO: 338         moltype = DNA  length = 20
FEATURE                Location/Qualifiers
misc_feature           1..20
                       note = PCR primer
source                 1..20
                       mol_type = other DNA
                       organism = synthetic construct
SEQUENCE: 338
ctggaatcaa agtcgaccca                                             20

SEQ ID NO: 339         moltype = DNA  length = 22
FEATURE                Location/Qualifiers
misc_feature           1..22
                       note = PCR primer
source                 1..22
                       mol_type = other DNA
                       organism = synthetic construct
SEQUENCE: 339
gcagcagtta cgccaaattc tt                                          22

SEQ ID NO: 340         moltype = DNA  length = 30
FEATURE                Location/Qualifiers
misc_feature           1..30
                       note = PCR primer
source                 1..30
                       mol_type = other DNA
                       organism = synthetic construct
SEQUENCE: 340
tgttataata tytatactgt gtgtaaaagc                                  30
```

-continued

```
SEQ ID NO: 341          moltype = DNA  length = 24
FEATURE                 Location/Qualifiers
misc_feature            1..24
                        note = PCR primer
source                  1..24
                        mol_type = other DNA
                        organism = synthetic construct
SEQUENCE: 341
tgagaccgta ytttttgttg aagc                                          24
```